United States Patent
Hamberger et al.

(10) Patent No.: US 10,240,173 B2
(45) Date of Patent: Mar. 26, 2019

(54) BIOSYNTHESIS OF FORSKOLIN AND RELATED COMPOUNDS

(71) Applicants: University of Copenhagen, Copenhagen (DK); Danmarks Tekniske Universitet, Lyngby (DK); Evolva SA, Reinach (CH)

(72) Inventors: Björn Hamberger, Kastrup (DK); Birger Lindberg Møller, Brønshøj (DK); Eirini Pateraki, Vallensbeak Strand (DK); Johan Andersen-Ranberg, Copenhagen (DK); Niels Bjerg Jensen, Kastrup (DE)

(73) Assignees: University of Copenhagen, Copenhagen (DK); Danmarks Tekniske Universitet, Lyngby (DK); Evolva SA, Reinach (CH)

( * ) Notice: Subject to any disclaimer, the term of this patent is extended or adjusted under 35 U.S.C. 154(b) by 0 days.

(21) Appl. No.: 16/031,492

(22) Filed: Jul. 10, 2018

(65) Prior Publication Data

US 2019/0010527 A1    Jan. 10, 2019

Related U.S. Application Data

(62) Division of application No. 15/110,795, filed as application No. PCT/DK2015/050020 on Jan. 30, 2015, now Pat. No. 10,053,717.

(30) Foreign Application Priority Data

Jan. 31, 2014 (DK) .................................. 2014 00057
Jun. 23, 2014 (DK) .................................. 2014 70380
Sep. 3, 2014 (DK) .................................. 2014 70536

(51) Int. Cl.
*C12N 1/20* (2006.01)
*C12P 17/06* (2006.01)
*C12P 5/00* (2006.01)
*C12N 9/02* (2006.01)

(52) U.S. Cl.
CPC ............ *C12P 17/06* (2013.01); *C12N 9/0071* (2013.01); *C12P 5/007* (2013.01); *C12Y 114/14001* (2013.01)

(58) Field of Classification Search
CPC ...................... C12N 9/0071; C12Y 114/14001
USPC .......................................................... 435/190
See application file for complete search history.

(56) References Cited

U.S. PATENT DOCUMENTS 10,053,717 B2 * 8/2018 Hamberger .......... C12N 9/0071

* cited by examiner

*Primary Examiner* — Tekchand Saidha
(74) *Attorney, Agent, or Firm* — McDonnell Boehnen Hulbert & Berghoff LLP

(57) ABSTRACT

The invention described materials and methods for producing oxidized 13R-MO, such as forskolin. In particular, the invention describes P450s involved in oxidation of 13R-MO including CYP76AH8, CYP76AH11, CYP76AH15, CYP76AH17, CYP71D381 and CYP76AH9. Host organisms expressing one or more of these P450s are useful in the production of oxidized 13R-MO.

9 Claims, 12 Drawing Sheets
Specification includes a Sequence Listing.

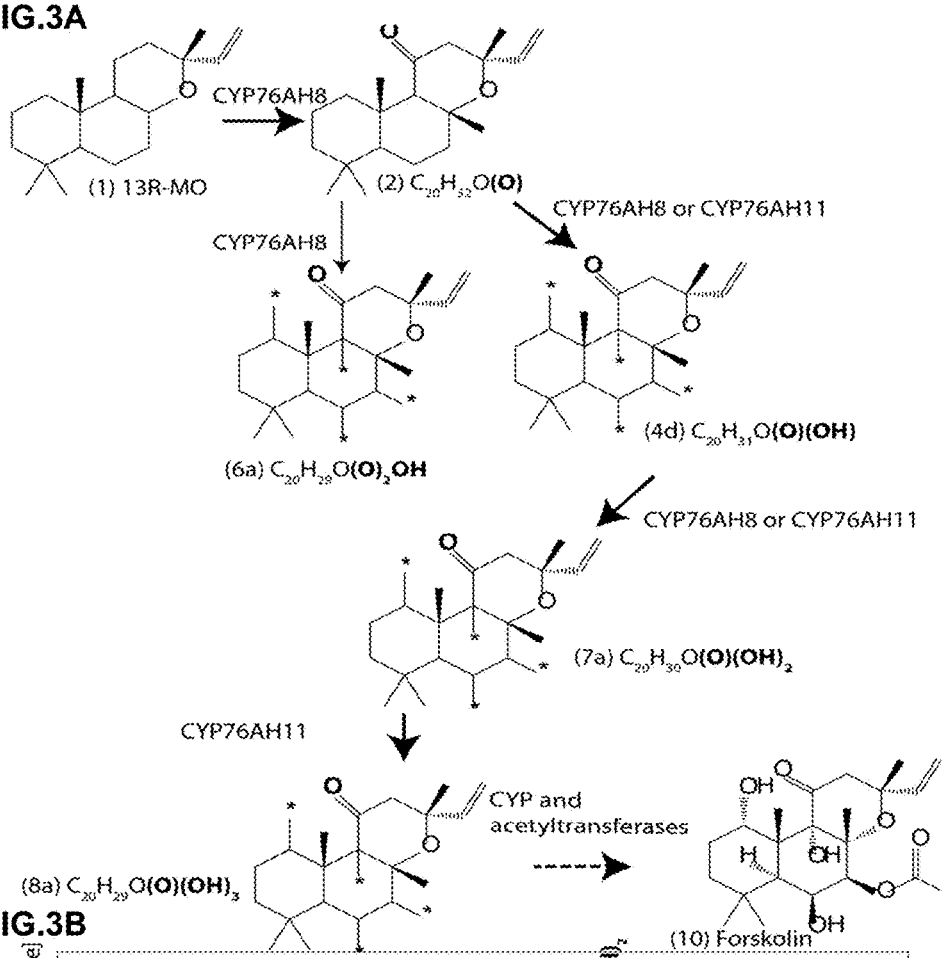
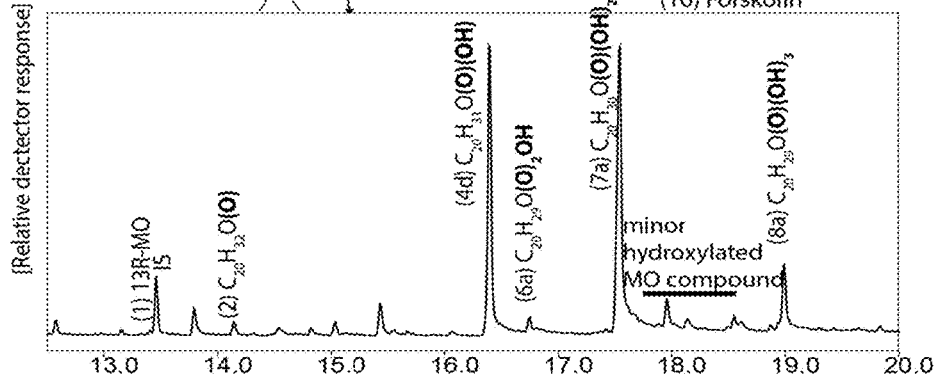

BIOSYNTHESIS OF FORSKOLIN AND RELATED COMPOUNDS

CROSS-REFERENCE TO RELATED APPLICATIONS

This application is a divisional of U.S. application Ser. No. 15/110,795, filed Jul. 11, 2016, now U.S. patent Ser. No. 10/053,717, issued on Aug. 21, 2018, which is a U.S. National Phase application under 35 U.S.C. § 371 of PCT/DK2015/050020, filed on Jan. 30, 2015, which claims priority from and the benefit of DK application No. 2014 00057, filed on Jan. 31, 2014, DK application No. 2014 70380, filed on Jun. 23, 2014, and DK application No. 2014 70536, filed on Sep. 3, 2014, the specifications of which are hereby incorporated by reference in their entireties.

FIELD OF INVENTION

The present invention relates to the field of biosynthesis of terpenoids. More specifically the invention relates to methods for biosynthesis of forskolin and related compounds, such as to biosynthesis of oxidised 13R-MO.

BACKGROUND OF INVENTION

Forskolin is a complex functionalised derivative of 13R-MO requiring region- and stereospecific oxidation of five carbon positions. Forskolin is a diterpene naturally produced by *Coleus forskohlii*. Both Forskolin and oxidized variants of forskolin have been suggested as useful in treatment in a number of clinical conditions. Forskolin has the ability to decrease the intraocular pressure therefore it is used today as an antiglaucoma agent (Wagh K, Patil P, Surana S, Wagh V. Forskolin: Upcoming antiglaucoma molecule, J Postgrad Med 2012, 58(3):199-202), in the form of eye drops. Moreover a water-soluble analogue of forskolin (NKH477) has been approved for commercial use in Japan for treatment of acute heart failure and heart surgery complications because of its vasodilatory effects when administered intravenously (Kikura M, Morita K, Sato S. Pharmacokinetics and a simulation model of colforsin daropate, new forskolin derivative inotropic vasodilator, in patients undergoing coronary artery bypass grafting. Pharmacol Res 2004, 49: 275-281). Forskolin also acts as bronchodilator so it could be used for asthma treatments (Yousif M H and Thulesius O. Forskolin reverses tachyphylaxis to the bronchodilator effects of salbutamol: an in-vitro study on isolated guinea-pig trachea. J Pharm Pharmacol, 1999. 51:181-186). Forskolin may help additionally to treat obesity by contributing to higher rates of body fat burning and promoting lean body mass formation (Godard M P, Johnson B A, Richmond S R. Body composition and hormonal adaptations associated with forskolin consumption in overweight and obese men. Obes Res 2005, 13:1335-1343)

SUMMARY OF INVENTION

Hitherto forskolin has been purified from *Coleus forskohlii* or produced chemically. Here novel methods for biosynthesis of forskolin and other oxidised 13R-MOs are presented. Oxidised 13R-MO may be valuable on its own account or as precursors for production of forskolin.

Thus, it is an aspect of the invention to provide methods of producing an oxidised 13R-manoyl oxide (13R-MO), said method comprising the steps of:

a) providing a host organism comprising
  I. A heterologous nucleic acid encoding an enzyme capable of catalysing hydroxylation of 13R-manoyl oxide (13R-MO) and/or an oxidised 13R-MO derivative at the 11 position, wherein said oxidised 13R-MO carries a —H at the 11-position; and/or catalysing oxidation of the hydroxyl group to form an oxo-group at the 11 position of 11-hydroxyl-13R-MO and/or an oxidised 11-hydroxyl-13R-MO;
  said host organism optionally comprising one or more of the following:
  II. A heterologous nucleic acid encoding an enzyme capable of catalysing hydroxylation of 13R-MO and/or oxidised 13R-MO at the 1 position, wherein said oxidised 13R-MO carries a —H at the 1-position;
  III. A heterologous nucleic acid encoding an enzyme capable of catalysing hydroxylation of 13R-MO and/or oxidised 13R-MO at the 6 position, wherein said oxidised 13R-MO carries a —H at the 6-position
  IV. A heterologous nucleic acid encoding an enzyme capable of catalysing hydroxylation of 13R-MO and/or oxidised 13R-MO at the 7 position, wherein said oxidised 13R-MO carries a —H at the 7-position
  V. A heterologous nucleic acid encoding an enzyme capable of catalysing hydroxylation of 13R-MO and/or oxidised 13R-MO at the 9 position, wherein said oxidised 13R-MO carries a —H at the 9-position
  VI. A heterologous nucleic acid encoding an enzyme capable of catalysing transfer of an acyl group to an —OH of a hydroxylated 13R-MO and/or an oxidised hydroxylated-13R-MO
b) Incubating said host organism in the presence of 13R-MO under conditions allowing growth of said host organism;
c) Optionally isolating oxidised 13R-MO from the host organism and/or from its surroundings.

If the host organism is a microorganism, then the oxidised 13R-MO may be isolated from the cultivation medium used for cultivation of the host organism.

Incubating the host organism in the presence of 13R-MO may for example be accomplished by the host organism being capable of producing 13R-MO or 13R-MO may be added to the host organism. In preferred embodiments the host organism is capable of producing 13R-MO.

It is also an aspect of the invention to provide host organisms comprising
  I. A heterologous nucleic acid encoding an enzyme capable of catalysing hydroxylation of 13R-manoyl oxide (13R-MO) and/or an oxidised 13R-MO derivative at the 11 position, wherein said oxidised 13R-MO carries a —H at the 11-position; and/or catalysing oxidation of the hydroxyl group to form an oxo-group at the 11 position of 11-hydroxyl-13R-MO and/or an oxidised 11-hydroxyl-13R-MO;
  said host organism optionally comprising one or more of the following:
  II. A heterologous nucleic acid encoding an enzyme capable of catalysing hydroxylation of 13R-MO and/or oxidised 13R-MO at the 1 position, wherein said oxidised 13R-MO carries a —H at the 1-position;
  III. A heterologous nucleic acid encoding an enzyme capable of catalysing hydroxylation of 13R-MO and/or oxidised 13R-MO at the 6 position, wherein said oxidised 13R-MO carries a —H at the 6-position;
  IV. A heterologous nucleic acid encoding an enzyme capable of catalysing hydroxylation of 13R-MO and/or oxidised 13R-MO at the 7 position, wherein said oxidised 13R-MO carries a —H at the 7-position;

V. A heterologous nucleic acid encoding an enzyme capable of catalysing hydroxylation of 13R-MO and/or oxidised 13R-MO at the 9 position, wherein said oxidised 13R-MO carries a —H at the 9-position VI. A heterologous nucleic acid encoding an enzyme capable of catalysing transfer of an acyl group to an —OH of a hydroxylated 13R-MO and/or an oxidised hydroxylated-13R-MO.

It is also an aspect of the invention to provide enzymes capable of

I. catalysing hydroxylation of 13R-manoyl oxide (13R-MO) and/or an oxidised 13R-MO at the 11 position, wherein said oxidised 13R-MO carries a —H at the 11-position; and/or II. catalysing oxidation of the hydroxyl group at the 11 position of 11-hydroxyl-13R-manoyl oxide and/or an oxidised 11-hydroxyl-13R-MO.

It is also an aspect of the invention to provide enzymes capable of catalysing hydroxylation of 11-keto-13R-manoyl oxide (13R-MO) and/or an oxidised 11-keto-13R-MO derivative at one or more of the positions 1, 6, 7 and/or 9.

It is also an aspect of the invention to provide enzymes capable of catalysing hydroxylation of 13R-manoyl oxide (13R-MO) and/or an oxidised 13R-MO at one or more of the positions 1, 6, 7 and/or 9.

DESCRIPTION OF DRAWINGS

FIG. 3A shows selected observed oxidation reactions of 13R-MO en route to forskolin. CYP76AH8 and CYP76AH11 effectively catalyse the first four reactions going via compound (2), 4d, 7a and 8a. Also compound 6a is produced* indicates possible position of —OH group(s). With respect to compound 6a * indicates possible position of =O or —OH group.

FIG. 3B shows GC-MS analysis of extracts from assays with *Nicotiana benthamiana* plants producing 13R-MO and expressing CYP76AH8 of SEQ ID NO:1 and CYP76AH11 of SEQ ID NO:2. (2) keto-13R-MO (8,13-epoxy-labd-14-ene-11-one), (6a) hydroxy-di-keto-13R-MO and (4d) keto-hydroxy-13R-MO, (4) keto-dihydroxy-13R-MO and (5) keto-trihydroxy-13R-MO are detected. A GC-MS trace with relative detector response and retention time in minutes

DETAILED DESCRIPTION OF THE INVENTION

Methods of Preparing Oxidised 13R-MO

Figure 1A:
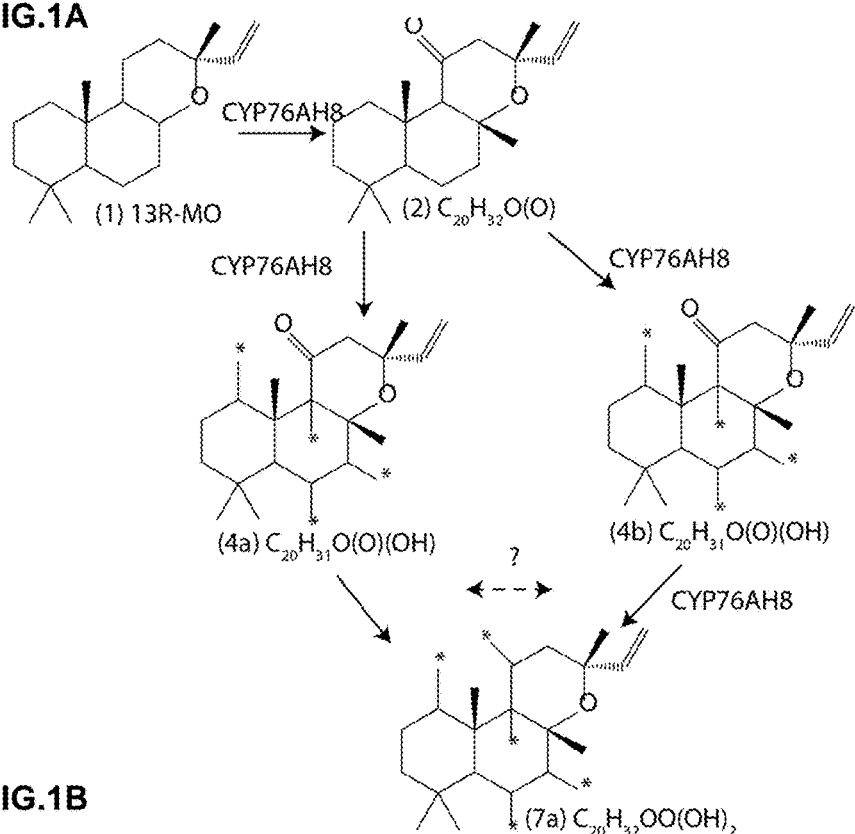
FIG. 1A shows a scheme of the full oxidation of (1) 13R-MO to (2) keto-13R-MO (8,13-epoxy-labd-14-ene-11-one), (4a) keto-hydroxy-13R-MO and (4b) keto-hydroxy-13R-MO and (7a) keto-dihydroxy-13R-MO by *Coleus forskohlii* CYP76AH8. * indicates possible position of —OH group(s).

It is one aspect of the present invention to provide biosynthetic methods for preparing oxidised 13R-MO. The methods of the invention generally comprise the steps of:

1) Providing a host organism comprising one or more of the following:
   I. A heterologous nucleic acid encoding an enzyme capable of catalysing hydroxylation of 13R-manoyl oxide (13R-MO) and/or an oxidised 13R-MO derivative at the 11 position, wherein said oxidised 13R-MO carries a —H at the 11-position; and/or catalysing oxidation of the hydroxyl group to form an oxo-group at the 11 position of 11-hydroxyl-13R-MO and/or an oxidised 11-hydroxyl-13R-MO;
   II. A heterologous nucleic acid encoding an enzyme capable of catalysing hydroxylation of 13R-MO and/or oxidised 13R-MO at the 1 position, wherein said oxidised 13R-MO carries a —H at the 1-position;
   III. A heterologous nucleic acid encoding an enzyme capable of catalysing hydroxylation of 13R-MO and/or oxidised 13R-MO at the 6 position, wherein said oxidised 13R-MO carries a —H at the 6-position
   IV. A heterologous nucleic acid encoding an enzyme capable of catalysing hydroxylation of 13R-MO and/or oxidised 13R-MO at the 7 position, wherein said oxidised 13R-MO carries a —H at the 7-position
   V. A heterologous nucleic acid encoding an enzyme capable of catalysing hydroxylation of 13R-MO and/or oxidised 13R-MO at the 9 position, wherein said oxidised 13R-MO carries a —H at the 9-position
   VI. A heterologous nucleic acid encoding an enzyme capable of catalysing transfer of an acyl group to an —OH of a hydroxylated 13R-MO and/or an oxidised hydroxylated-13R-MO
2) Incubating said host organism in the presence of 13R-MO under conditions allowing growth of said host organism
3) Optionally isolating oxidised 13R-MO from the host organism.

The structure of 13R-MO is provided herein below in the section "Oxidised 13R-MO.

The oxidised 13R-MO may be any of the oxidised 13R-MO described herein below in the section "Oxidised 13R-MO".

The term "oxidised 11-hydroxyl-13R-MO" as used herein refers to 11-hydroxyl-13R-MO further substituted at one or more of the positions 1, 6, 7 and 9 with a moiety selected from the group consisting of =O, —OH and OR, wherein R preferably is acyl.

The term "oxidised hydroxylated-13R-MO" as used herein refers to 13R-MO, which is substituted with hydroxyl on at least one of the positions 1, 6, 7 and 9, and which further is substituted at one or more of the others positions 1, 6, 9 and 11 with a moiety selected from the group consisting of =O, —OH and OR, wherein R preferably is acyl.

The term "oxidised 11-keto-13R-MO" as used herein refers to 13R-MO, which is substituted with oxo at the 11 position and which further is substituted at one or more of the positions 1, 6, 9 and 11 with a moiety selected from the group consisting of =O, —OH and OR, wherein R preferably is acyl.

The heterologous nucleic acid I. may for example be a heterologous encoding any of the enzymes described in the section "I. Enzyme catalysing hydroxylation of 13R-MO at the 11 position" herein below. The heterologous nucleic acid II. may for example be a heterologous encoding any of the enzymes described in the section "II. Enzyme catalysing hydroxylation of 13R-MO at the 1 position" herein below. The heterologous nucleic acid III. may for example be a heterologous encoding any of the enzymes described in the section "III. Enzyme catalysing hydroxylation of 13R-MO at the 6 position" herein below. The heterologous nucleic acid IV. may for example be a heterologous encoding any of the enzymes described in the section "IV. Enzyme catalysing hydroxylation of 13R-MO at the 7 position" herein below. The heterologous nucleic acid V. may for example be a heterologous encoding any of the enzymes described in the section "V. Enzyme catalysing hydroxylation of 13R-MO at the 9 position" herein below. The heterologous nucleic acid VI. may for example be a heterologous encoding any of the enzymes described in the section "VI. Enzyme catalysing transfer of an acyl group" herein below.

The host organism may comprise one of more of the heterologous nucleic acids I., II., III., IV., V. and VI, such as at least 2, for example at least 3, such as at least 4, for example at least 5, such as all of heterologous nucleic acids I., II., III., IV., V. and VI.

Incubating said host organism in the presence of 13R-MO may be obtained in several manners. For example, 13R-MO may be added to the host organism. If the host organism is a microorganism, then 13R-MO may be added to the cultivation medium of said microorganism. If the host organism is a plant, then 13R-MO may be added to the growing soil of the plant or it may be introduced into the plant by infiltration. Thus, if the heterologous nucleic(s) are introduced into the plant by infiltration, then 13R-MO may be co-infiltrated together with the heterologous nucleic acid(s).

It is also comprised within the invention that the host organism is capable of producing 13R-MO. In such embodiments incubating said host organism in the presence of 13R-MO simply requires cultivating said host organism.

In one embodiment of the invention the host organism comprises one or more heterologous nucleic acids encoding enzymes involved in the production of 13R-MO. Thus, in preferred embodiments of the invention the host organism comprises in addition to the heterologous nucleic acids I., II., III., IV., V. and/or VI at least one of the following heterologous nucleic acids:

IX. A heterologous nucleic acid encoding TPS2, such as any of the TPS2 described herein below in the section "IX. TPS2"
X. A heterologous nucleic acid encoding TPS3, such as any of the TPS3 described herein below in the section "X. TPS3", and/or
XI. A heterologous nucleic acid encoding TPS4, such as any of the TPS4 described herein below in the section "XI. TPS4"

Such host organisms are in general capable of producing 13R-MO and thus, no 13R-MO needs to be added to such host organisms. In such embodiments it is preferable that the host organism is incubated in the presence of GGPP. Many host organisms are capable of producing GGPP, and thus incubation in the presence of GGPP may be simply require cultivation of the host organism.

The host organism according to the invention may also comprise one or more additional heterologous nucleic acids, in addition to the heterologous nucleic acids described herein.

The methods of the invention may also be performed in vitro. Thus, the method of producing an oxidised 13R-MO may comprise the steps of i. providing a host organism comprising one or more of the heterologous nucleic acids I., II., III., IV., V. and VI, and preferably comprising at least the heterologous nucleic acid I., b) preparing an extract of said host organism;

c) providing 13R-MO d) incubating said extract with 13R-MO thereby producing oxidised 13R-MO.

The method of producing an oxidised 13R-MO may also comprise the steps of a) providing a host organism comprising one or more of the heterologous nucleic acids I., II., III., IV., V., VI, IX, X and XI, preferably comprising at least the heterologous nucleic acid I., IX and X, b) preparing an extract of said host organism;

d) incubating said extract in the presence of GGPP thereby producing oxidised 13R-MO.

The host organism may be any of the host organisms described herein below in the section "Host organism".

I. Enzyme Catalysing Hydroxylation of 13R-MO at the 11 Position

The host organisms to be used with the present invention comprise one or more heterologous nucleic acids. Thus, the host organism may comprise a heterologous nucleic acid encoding an enzyme capable of a) catalysing hydroxylation of 13R-manoyl oxide (13R-MO) and/or an oxidised 13R-MO derivative at the 11 position, wherein said oxidised 13R-MO carries a —H at the 11-position; and/or b) catalysing oxidation of the hydroxyl group at the 11 position of 11-hydroxyl-13R-MO and/or an oxidised 11-hydroxyl-13R-MO to form an oxo-group.

Said enzyme may for example be any of the enzymes described herein in this section and may also be referred to herein as "enzyme I". It is in particular preferred that the host organism comprises a heterologous nucleic acid encoding said enzyme, in embodiments of the invention, wherein the oxidised 13R-MO to be produced is substituted at the 11 position with a moiety selected from the group consisting of =O, —OH and OR, wherein R preferably is acyl, and in particular in embodiments of the invention, wherein the oxidised 13R-MO to be produced is substituted at the 11 position with oxo (=O).

The enzyme I may be an enzyme having one or two functions. In particular it is preferred that the enzyme I is capable of catalysing the following reaction Ia:

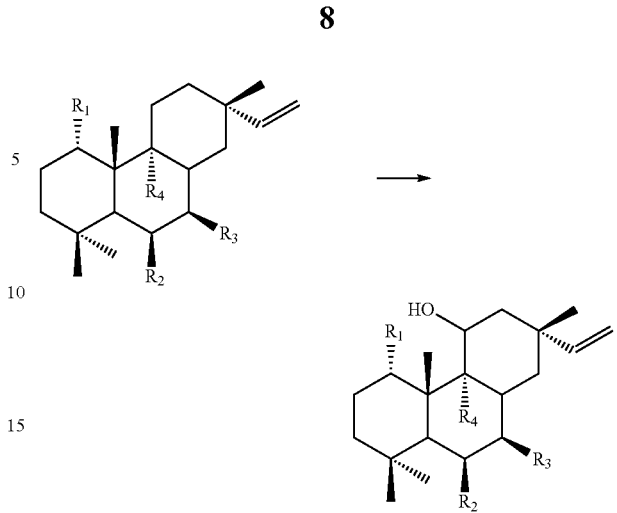

and/or the reaction Id:

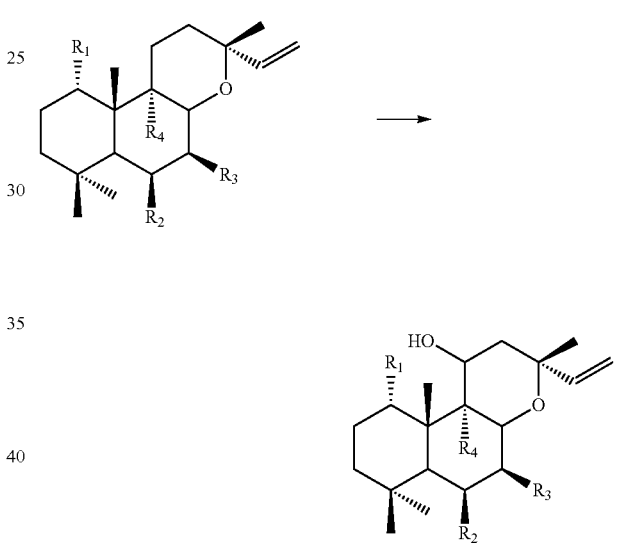

wherein $R_1$, $R_2$, $R_3$ and $R_4$ individually are selected from the group consisting of —H, —OH and —OR, wherein R preferably is acyl. Acyl is as defined in the section "Oxidised 13R-MO" herein below.

In particular, at least one of $R_1$, $R_2$, $R_3$ and $R_4$ is —H, for example at least two of $R_1$, $R_2$, $R_3$ and $R_4$ is —H, for example at least three of $R_1$, $R_2$, $R_3$ and $R_4$ is —H. In one embodiment all of $R_1$, $R_2$, $R_3$ and $R_4$ is —H.

It is also preferred that the enzyme I is capable of catalysing the following reaction Ib:

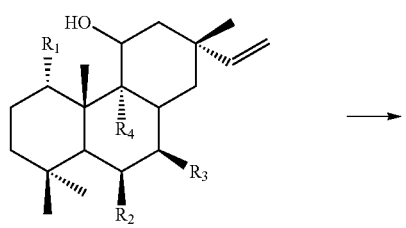

-continued

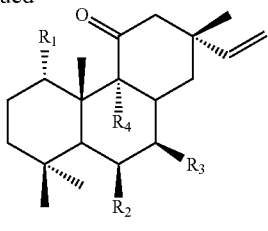

and/or reaction Ie:

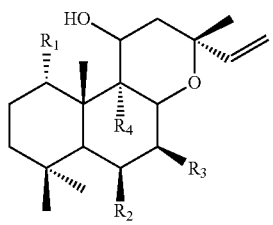

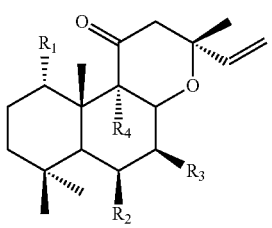

wherein $R_1$, $R_2$, $R_3$ and $R_4$ individually are selected from the group consisting of —H, —OH and —OR, wherein R preferably is acyl. Acyl is as defined in the section "Oxidised 13R-MO" herein below.

In particular, at least one of $R_1$, $R_2$, $R_3$ and $R_4$ is —H, for example at least two of $R_1$, $R_2$, $R_3$ and $R_4$ is —H, for example at least three of $R_1$, $R_2$, $R_3$ and $R_4$ is —H. In one embodiment all of $R_1$, $R_2$, $R_3$ and $R_4$ is —H.

It is even more preferred that enzyme I is capable of catalysing both of reactions Ia and Ib outlined above. It is very preferred that enzyme I is capable of catalysing both of reactions Id and Ie outlined above.

It is also possible that enzyme I is capable of catalysing the reaction Ic:

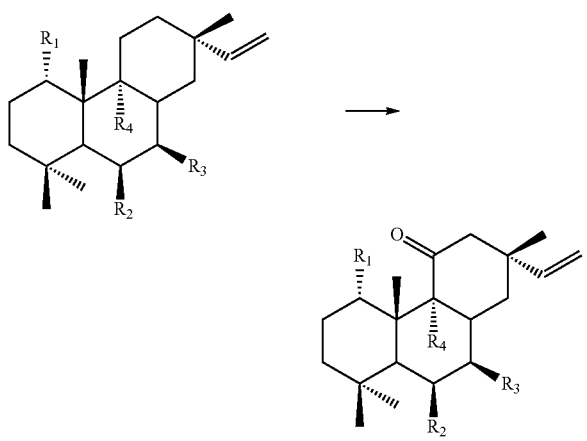

and/or the reaction If:

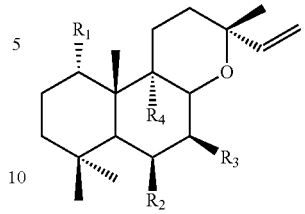

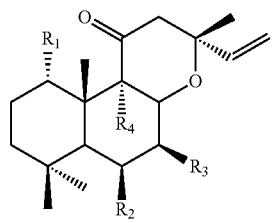

In particular, at least one of $R_1$, $R_2$, $R_3$ and $R_4$ is —H, for example at least two of $R_1$, $R_2$, $R_3$ and $R_4$ is —H, for example at least three of $R_1$, $R_2$, $R_3$ and $R_4$ is —H. In one embodiment all of $R_1$, $R_2$, $R_3$ and $R_4$ is —H.

Enzyme I may be any useful enzyme with above mentioned activities, in particular enzyme I may be a CYP450. Enzyme I may be derived from any suitable source, but in a preferred embodiment enzyme I is an enzyme from *Coleus forskohlii*. Thus enzyme I may be a CYP450 from *Coleus forskohlii*.

In a preferred embodiment of the invention, enzyme I is CYP76AH8, preferably enzyme I is CYP76AH8 of SEQ ID NO:1 or a functional homologue thereof sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith. The sequence identity is preferably calculated as described herein below in the section "Sequence identity". A functional homologue of CYP76AH8 is a polypeptide also capable of catalysing reactions Ia, Ib, Id and/or Ie described above.

In another embodiment of the invention, enzyme I is CYP76AH17, preferably enzyme I may be CYP76AH17 of SEQ ID NO:10 or a functional homologue thereof sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith. The sequence identity is preferably calculated as described herein below in the section "Sequence identity". A functional homologue of CYP76AH17 is a polypeptide also capable of catalysing reactions Ia, Ib, Id and/or Ie described above.

In another embodiment of the invention, enzyme I is CYP76AH15, preferably enzyme I may be CYP76AH15 of SEQ ID NO:11 or a functional homologue thereof sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith. The sequence identity is preferably calculated as described herein below in the section "Sequence identity". A functional homologue of CYP76AH15 is a polypeptide also capable of catalysing reactions Ia, Ib, Id and/or Ie described above.

In embodiments of the invention, wherein enzyme I catalyses reaction Ia and/or Id, then enzyme I may be CYP76AH11, preferably enzyme I may be CYP76AH11 of SEQ ID NO:2 or a functional homologue thereof sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith. The sequence identity is preferably calculated as described herein below in the section "Sequence identity". A functional homologue of CYP76AH11 may be a polypeptide capable of catalysing reaction Ia and/or Id described above.

II. Enzyme Catalysing Hydroxylation of 13R-MO at the 1 Position

The host organisms to be used with the present invention comprise one or more heterologous nucleic acids. Thus, the host organism may comprise a heterologous nucleic acid encoding an enzyme capable of catalysing hydroxylation of 13R-MO and/or oxidised 13R-MO at the 1 position, wherein said oxidised 13R-MO carries a —H at the 1-position. For example, said enzyme may be capable of catalysing hydroxylation of oxidised 11-keto-13R-MO at the 1 position.

Said enzyme may for example be any of the enzymes described herein in this section and may also be referred to herein as "enzyme II". It is in particular preferred that the host organism comprises a heterologous nucleic acid encoding said enzyme, in embodiments of the invention, wherein the oxidised 13R-MO to be produced is substituted at least at the 1 position with a moiety selected from the group consisting of —OH and OR, wherein R preferably is acyl.

It is preferred that the enzyme II is capable of catalysing the following reaction IIa:

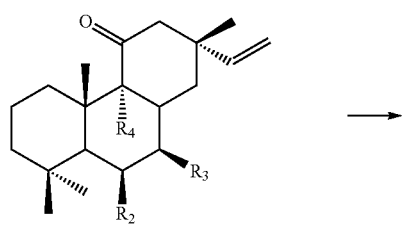

and/or the reaction IIc:

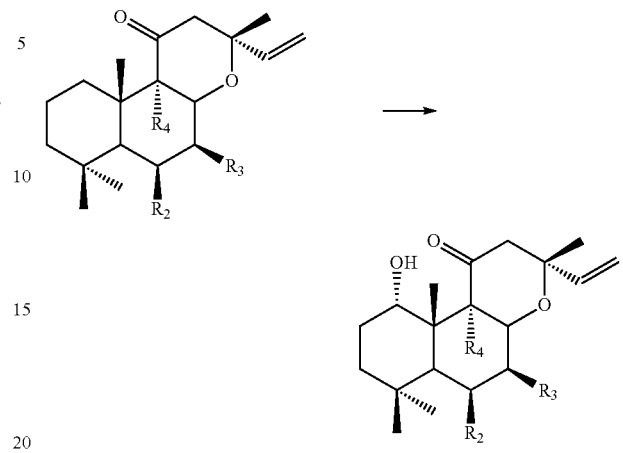

wherein $R_2$, $R_3$ and $R_4$ individually are selected from the group consisting of —H, —OH and —OR, wherein R preferably is acyl. Acyl is as defined in the section "Oxidised 13R-MO" herein below.

In particular, at least one of $R_2$, $R_3$ and $R_4$ is —H, for example at least two of $R_2$, $R_3$ and $R_4$ is —H, for example all of $R_2$, $R_3$ and $R_4$ is —H.

In one preferred embodiment enzyme II is capable of catalysing reaction IIa, wherein $R_2$ and $R_3$ is —OH and $R_4$ is —H.

It is also preferred that enzyme II is capable of catalysing the following reaction IIb:

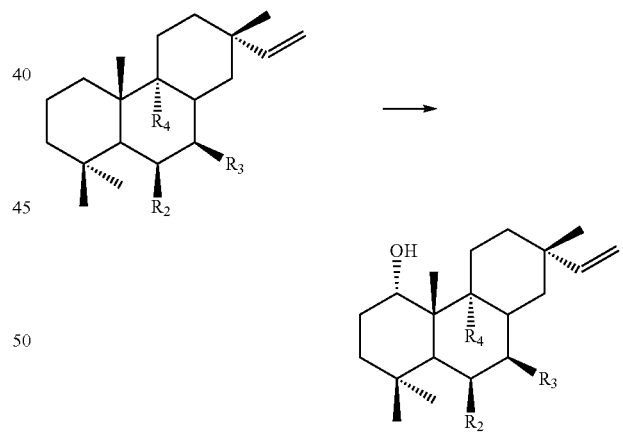

and/or the reaction IId:

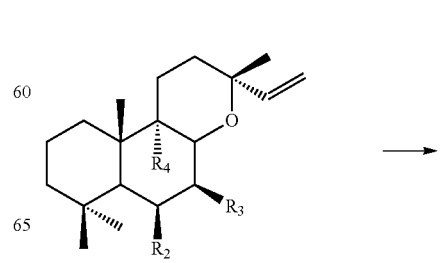

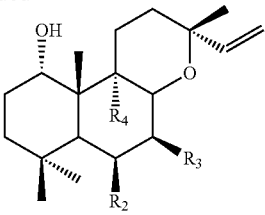

wherein $R_2$, $R_3$ and $R_4$ individually are selected from the group consisting of —H, —OH and —OR, wherein R preferably is acyl. acyl is as defined in the section "Oxidised 13R-MO" herein below.

In particular, at least one of $R_2$, $R_3$ and $R_4$ is —H, for example at least two of $R_2$, $R_3$ and $R_4$ is —H, for example all of $R_2$, $R_3$ and $R_4$ is —H.

Thus, enzyme II may be capable of catalysing reaction IIa or reaction IIb or both of reactions IIa and IIb outlined above. Enzyme II may also be capable of catalysing reaction IIc or reaction IId or both of reactions IIc and IId outlined above. It is also comprised within the invention that said enzyme in addition to being able to catalyse reactions IIa and/or IIb outlined above also may be able to catalyse other reactions, e.g. reactions IIIa, IIIb, IIIc, IIId, IVa, IVb, IVc, IVd, Va, Vb, Vc or Vd outlined below.

Enzyme II may be any useful enzyme with above mentioned activities, in particular enzyme II may be a CYP450. Enzyme II may be derived from any suitable source, but in a preferred embodiment enzyme II is an enzyme from *Coleus forskohlii*. Thus enzyme II may be a CYP450 from *Coleus forskohlii*.

In one embodiment of the invention, enzyme II is selected from the group consisting of CYP76AH11, CYP71D381 and CYP76AH9. Thus enzyme II may be selected from the group consisting CYP76AH11 of SEQ ID NO:2, CYP71D381 of SEQ ID NO:3, CYP76AH9 of SEQ ID NO:4 and functional homologues of any of the aforementioned sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith.

In particular, in embodiments of the invention wherein enzyme II is capable of catalysing reaction IIa and/or IIc, then enzyme II may be CYP76AH11, such as CYP76AH11 of SEQ ID NO:2 or a functional homologue thereof sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith. Thus, enzyme II may be CYP76AH11 of SEQ ID NO:2 or a functional homologue thereof in embodiments of the invention, wherein enzyme II is capable of catalysing any of reactions IIa, IIb, IIc and/or IId, wherein $R_2$ and $R_3$ is —OH and $R_4$ is —H.

In embodiments of the invention wherein enzyme II is capable of catalysing reaction IIb or IId, then enzyme II may in particular be CYP71D381 or CYP76AH9, such as CYP71D381 of SEQ ID NO:3, CYP76AH9 of SEQ ID NO:4 or a functional homologue of any of the aforementioned sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith.

The sequence identity is preferably calculated as described herein below in the section "Sequence identity". A functional homologue of CYP76AH11, CYP71D381 and CYP76AH9 may be capable of catalysing reactions IIa, IIb, IIc and/or IId described above.

In another embodiment of the invention, enzyme II is selected from the group consisting of CYP76AH8 of SEQ ID NO:1, CYP76AH15 of SEQ ID NO:11, CYP76AH17 of SEQ ID NO:10 or a functional homologue of any of the aforementioned sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith. The sequence identity is preferably calculated as described herein below in the section "Sequence identity". A functional homologue of CYP76AH8, CYP76AH15 or CYP76AH17 may be a polypeptide also capable of catalysing reactions IIc and/or IId described above.

III. Enzyme Catalysing Hydroxylation of 13R-MO at the 6 Position

The host organisms to be used with the present invention comprise one or more heterologous nucleic acids. Thus, the host organism may comprise a heterologous nucleic acid encoding an enzyme capable of catalysing hydroxylation of 13R-MO and/or oxidised 13R-MO at the 6 position, wherein said oxidised 13R-MO carries a —H at the 6-position. For example, said enzyme may be capable of catalysing hydroxylation of oxidised 11-keto-13R-MO at the 6 position.

Said enzyme may for example be any of the enzymes described herein in this section and may also be referred to herein as "enzyme III". It is in particular preferred that the host organism comprises a heterologous nucleic acid encoding said enzyme, in embodiments of the invention, wherein the oxidised 13R-MO to be produced is substituted at least at the 6 position with a moiety selected from the group consisting of —OH and OR, wherein R preferably is acyl.

It is preferred that the enzyme III is capable of catalysing the following reaction IIIa:

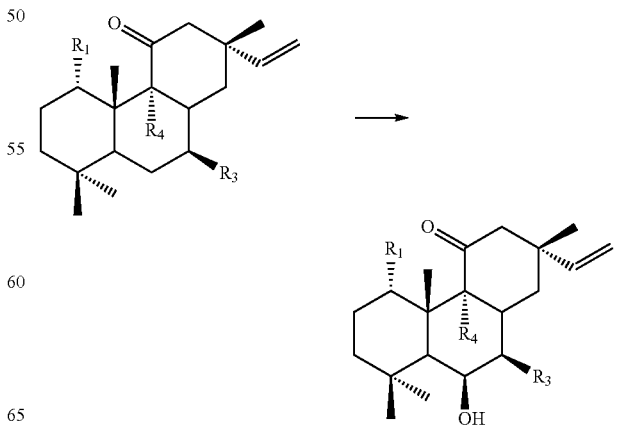

and/or the reaction IIIc:

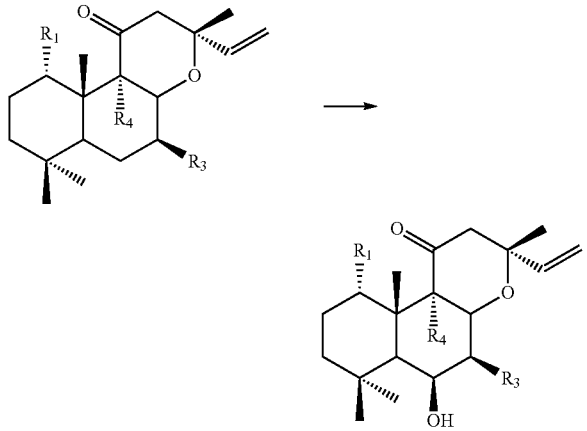

wherein $R_1$, $R_3$ and $R_4$ individually are selected from the group consisting of —H, —OH and —OR, wherein R preferably is acyl. Acyl is as defined in the section "Oxidised 13R-MO" herein below.

In particular, at least one of $R_1$, $R_3$ and $R_4$ is —H, for example at least two of $R_1$, $R_3$ and $R_4$ is —H, for example all of $R_1$, $R_3$ and $R_4$ is —H.

It is also preferred that enzyme III is capable of catalysing the following reaction IIIb:

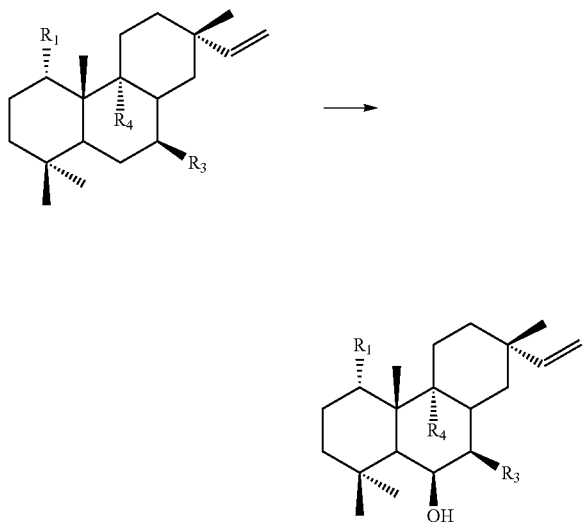

and/or the reaction IIId

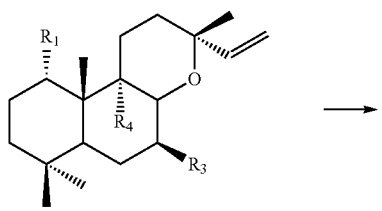

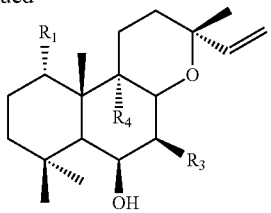

wherein $R_1$, $R_3$ and $R_4$ individually are selected from the group consisting of —H, —OH and —OR, wherein R preferably is acyl. acyl is as defined in the section "Oxidised 13R-MO" herein below.

In particular, at least one of $R_1$, $R_3$ and $R_4$ is —H, for example at least two of $R_1$, $R_3$ and $R_4$ is —H, for example all of $R_1$, $R_3$ and $R_4$ is —H.

In one preferred embodiment enzyme III is capable of catalysing reaction IIIa and/or IIIc, wherein all of $R_1$, $R_3$ and $R_4$ are —H.

Thus, enzyme III may be capable of catalysing reaction IIIa or reaction IIIb or both of reactions IIIa and IIIb outlined above. Enzyme III may also be capable of catalysing reactions IIIc or reaction IIId or both of reactions IIIc and IIId outlined above. It is also comprised within the invention that said enzyme in addition to being able to catalyse reactions IIIa, IIIb, IIIc and/or IIId outlined above also may be able to catalyse other reactions, e.g. reactions IIa, IIb, IIc, IId, IVa, IVb, IVc, IVd, Va, Vb, Vc or Vd outlined herein.

Enzyme III may be any useful enzyme with above mentioned activities, in particular enzyme III may be a CYP450. Enzyme III may be derived from any suitable source, but in a preferred embodiment enzyme III is an enzyme from *Coleus forskohlii*. Thus enzyme III may be a CYP450 from *Coleus forskohlii*.

In one embodiment of the invention, enzyme III is selected from the group consisting of CYP76AH11, CYP71D381 and CYP76AH9. Thus enzyme III may be selected from the group consisting CYP76AH11 of SEQ ID NO:2, CYP71D381 of SEQ ID NO:3, CYP76AH9 of SEQ ID NO:4 and functional homologues of any of the aforementioned sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith.

In particular, in embodiments of the invention wherein enzyme III is capable of catalysing reaction IIIa and/or IIIc, then enzyme III may be CYP76AH11, such as CYP76AH11 of SEQ ID NO:2 or a functional homologue thereof sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith.

In embodiments of the invention wherein enzyme III is capable of catalysing reaction IIIb and/or IIId, then enzyme III may in particular be CYP71D381 or CYP76AH9, such as CYP71D381 of SEQ ID NO:3, CYP76AH9 of SEQ ID NO:4 or a functional homologue of any of the aforementioned sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith.

The sequence identity is preferably calculated as described herein below in the section "Sequence identity". A functional homologue of CYP76AH11, CYP71D381 and CYP76AH9 may be capable of catalysing reactions IIIa, IIIb, IIIc and/or IIId described above.

In another embodiment of the invention, enzyme III is selected from the group consisting of CYP76AH8 of SEQ ID NO:1, CYP76AH15 of SEQ ID NO:11, CYP76AH17 of SEQ ID NO:10 or a functional homologue of any of the aforementioned sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith. The sequence identity is preferably calculated as described herein below in the section "Sequence identity". A functional homologue of CYP76AH8, CYP76AH15 or CYP76AH17 may be a polypeptide also capable of catalysing reactions IIIc and/or IIId described above.

IV. Enzyme Catalysing Hydroxylation of 13R-MO at the 7 Position

The host organisms to be used with the present invention comprise one or more heterologous nucleic acids. Thus, the host organism may comprise a heterologous nucleic acid encoding an enzyme capable of catalysing hydroxylation of 13R-MO and/or oxidised 13R-MO at the 7 position, wherein said oxidised 13R-MO carries a —H at the 7-position. For example, said enzyme may be capable of catalysing hydroxylation of oxidised 11-keto-13R-MO at the 7 position.

Said enzyme may for example be any of the enzymes described herein in this section and may also be referred to herein as "enzyme IV". It is in particular preferred that the host organism comprises a heterologous nucleic acid encoding said enzyme, in embodiments of the invention, wherein the oxidised 13R-MO to be produced is substituted at least at the 7 position with a moiety selected from the group consisting of —OH and OR, wherein R preferably is acyl.

It is preferred that the enzyme IV is capable of catalysing the following reaction IVa:

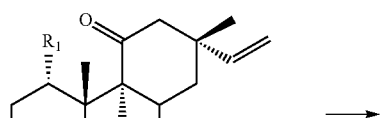
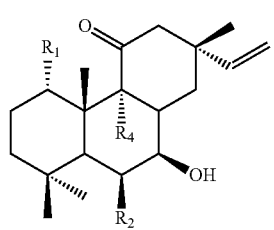

and/or reaction IVc:

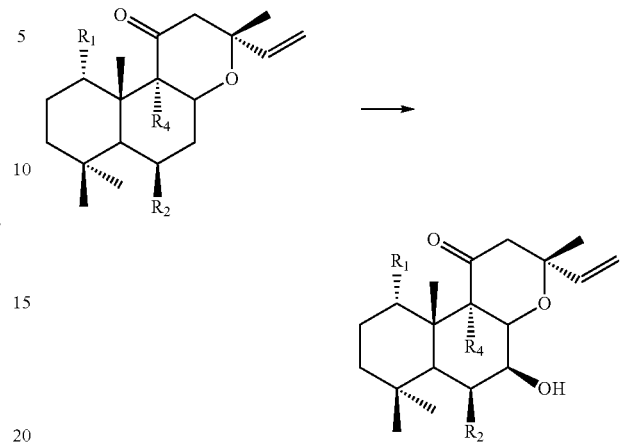
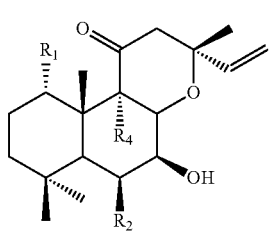

wherein $R_1$, $R_2$ and $R_4$ individually are selected from the group consisting of —H, —OH and —OR, wherein R preferably is acyl. acyl is as defined in the section "Oxidised 13R-MO" herein below.

In particular, at least one of $R_1$, $R_2$ and $R_4$ is —H, for example at least two of $R_1$, $R_2$ and $R_4$ is —H, for example all of $R_1$, $R_2$ and $R_4$ is —H.

In one preferred embodiment enzyme IV is capable of catalysing reaction Iva and/or IVc, wherein $R_1$ and $R_4$ are —H and $R_2$ is —OH.

It is also preferred that enzyme IV is capable of catalysing the following reaction IVb:

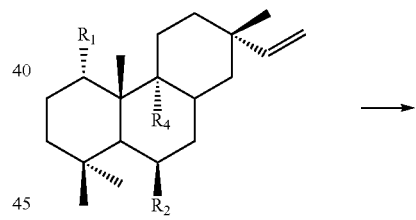
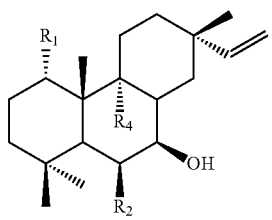

and/or reaction IVd:

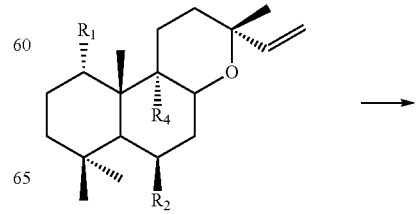
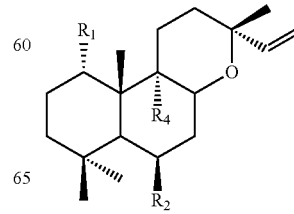

-continued

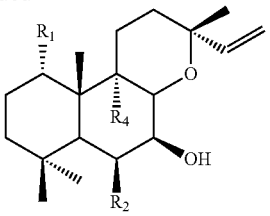

wherein $R_1$, $R_2$ and $R_4$ individually are selected from the group consisting of —H, —OH and —OR, wherein R preferably is acyl. acyl is as defined in the section "Oxidised 13R-MO" herein below.

In particular, at least one of $R_1$, $R_2$ and $R_4$ is —H, for example at least two of $R_1$, $R_2$ and $R_4$ is —H, for example all of $R_1$, $R_2$ and $R_4$ is —H.

Thus, enzyme IV may be capable of catalysing reaction IVa or reaction IVb or both of reactions IVa and IVb outlined above. Enzyme IV may also be capable of catalysing reaction IVc or reaction IVd or both of reactions IVc and IVd outlined above. It is also comprised within the invention that said enzyme in addition to being able to catalyse reactions Iva, IVb, IVc and/or IVd outlined above also may be able to catalyse other reactions, e.g. reactions Ia, Ib, Id, Ie, IIa, IIb, IIc, IId, Va, Vb, Vc or Vd outlined herein.

Enzyme IV may be any useful enzyme with above mentioned activities, in particular enzyme IV may be a CYP450. Enzyme IV may be derived from any suitable source, but in a preferred embodiment enzyme III is an enzyme from *Coleus forskohlii*. Thus enzyme IV may be a CYP450 from *Coleus forskohlii*.

In one embodiment of the invention, enzyme IV is selected from the group consisting of CYP76AH11, CYP71D381 and CYP76AH9. Thus enzyme IV may be selected from the group consisting CYP76AH11 of SEQ ID NO:2, CYP71D381 of SEQ ID NO:3, CYP76AH9 of SEQ ID NO:4 and functional homologues of any of the aforementioned sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith.

In particular, in embodiments of the invention wherein enzyme IV is capable of catalysing reaction IVa and/or IVc, then enzyme IV may be CYP76AH11, such as CYP76AH11 of SEQ ID NO:2 or a functional homologue thereof sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith. Thus, enzyme IV may be CYP76AH11 of SEQ ID NO:2 or a functional homologue thereof in embodiments of the invention, wherein enzyme IV is capable of catalysing reaction Iva and/or IVc, wherein $R_1$ and $R_4$ are —H and $R_2$ is —OH.

In embodiments of the invention wherein enzyme IV is capable of catalysing reaction IVb and/or IVd, then enzyme IV may in particular be CYP71D381 or CYP76AH9, such as CYP71D381 of SEQ ID NO:3, CYP76AH9 of SEQ ID NO:4 or a functional homologue of any of the aforementioned sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith.

The sequence identity is preferably calculated as described herein below in the section "Sequence identity". A functional homologue of CYP76AH11, CYP71D381 and CYP76AH9 may be capable of catalysing reactions Iva, IVb, IVc and/or IVd described above.

In another embodiment of the invention, enzyme IV is selected from the group consisting of CYP76AH8 of SEQ ID NO:1, CYP76AH15 of SEQ ID NO:11, CYP76AH17 of SEQ ID NO:10 or a functional homologue of any of the aforementioned sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith. The sequence identity is preferably calculated as described herein below in the section "Sequence identity". A functional homologue of CYP76AH8, CYP76AH15 or CYP76AH17 may be a polypeptide also capable of catalysing reactions IVc and/or IVd described above.

V. Enzyme Catalysing Hydroxylation of 13R-MO at the 9 Position

The host organisms to be used with the present invention comprise one or more heterologous nucleic acids. Thus, the host organism may comprise a heterologous nucleic acid encoding an enzyme capable of catalysing hydroxylation of 13R-MO and/or oxidised 13R-MO at the 9 position, wherein said oxidised 13R-MO carries a —H at the 9-position. For example, said enzyme may be capable of catalysing hydroxylation of oxidised 11-keto-13R-MO at the 9 position.

Said enzyme may for example be any of the enzymes described herein in this section and may also be referred to herein as "enzyme V". It is in particular preferred that the host organism comprises a heterologous nucleic acid encoding said enzyme, in embodiments of the invention, wherein the oxidised 13R-MO to be produced is substituted at least at the 9 position with a moiety selected from the group consisting of —OH and OR, wherein R preferably is acyl.

It is preferred that the enzyme V is capable of catalysing the following reaction Va:

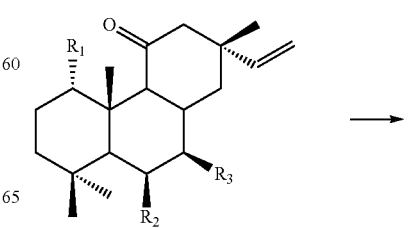

-continued

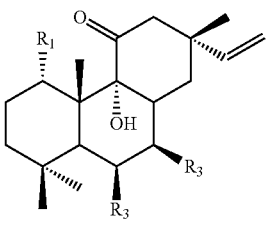

and/or the reaction Vc:

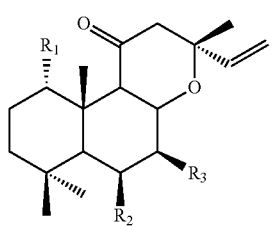

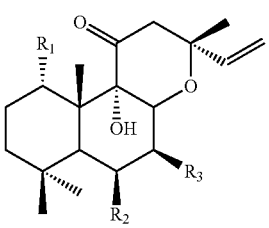

wherein $R_1$, $R_2$ and $R_3$ individually are selected from the group consisting of —H, —OH and —OR, wherein R preferably is acyl. acyl is as defined in the section "Oxidised 13R-MO" herein below.

In particular, at least one of $R_1$, $R_2$ and $R_3$ is —H, for example at least two of $R_1$, $R_2$ and $R_3$ is —H, for example all of $R_1$, $R_2$ and $R_3$ is —H.

It is also preferred that enzyme V is capable of catalysing the following reaction Vb:

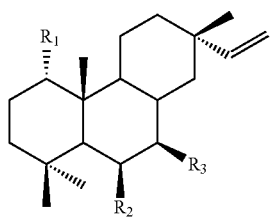

and/or the reaction Vd

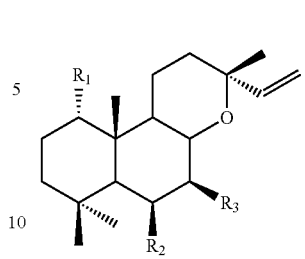

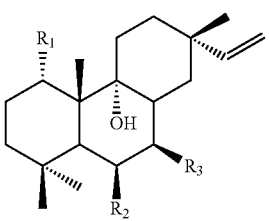

wherein $R_1$, $R_2$ and $R_3$ individually are selected from the group consisting of —H, —OH and —OR, wherein R preferably is acyl. acyl is as defined in the section "Oxidised 13R-MO" herein below.

In particular, at least one of $R_1$, $R_2$ and $R_3$ is —H, for example at least two of $R_1$, $R_2$ and $R_3$ is —H, for example all of $R_1$, $R_2$ and $R_3$ is —H.

Thus, enzyme V may be capable of catalysing reaction Va or reaction Vb or both of reactions Va and Vb outlined above. Enzyme V may also be capable of catalysing reaction Vc or reaction Vd or both of reactions Vc and Vd outlined above It is also comprised within the invention that said enzyme in addition to being able to catalyse reactions Va, Vb, Vc and/or Vd outlined above also may be able to catalyse other reactions, e.g. reactions Ia, Ib, Id, Ie, IIa, IIb, IIc, IId, IVa, IVb, IVc or IVd outlined herein.

Enzyme V may be any useful enzyme with above mentioned activities, in particular enzyme V may be a CYP450. Enzyme V may be derived from any suitable source, but in a preferred embodiment enzyme III is an enzyme from *Coleus forskohlii*. Thus enzyme V may be a CYP450 from *Coleus forskohlii*.

In one embodiment of the invention, enzyme V is selected from the group consisting of CYP76AH11, CYP71D381 and CYP76AH9. Thus enzyme V may be selected from the group consisting CYP76AH11 of SEQ ID NO:2, CYP71D381 of SEQ ID NO:3, CYP76AH9 of SEQ ID NO:4 and functional homologues of any of the aforementioned sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith.

In particular, in embodiments of the invention wherein enzyme V is capable of catalysing reactions Va and/or Vc, then enzyme V may be CYP76AH11, such as CYP76AH11 of SEQ ID NO:2 or a functional homologue thereof sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith.

In embodiments of the invention wherein enzyme V is capable of catalysing reaction Vb and/or Vd, then enzyme V may in particular be CYP71D381 or CYP76AH9, such as CYP71D381 of SEQ ID NO:3, CYP76AH9 of SEQ ID NO:4 or a functional homologue of any of the aforementioned sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith.

The sequence identity is preferably calculated as described herein below in the section "Sequence identity". A functional homologue of CYP76AH11, CYP71D381 and CYP76AH9 may be capable of catalysing reactions Vc and/or Vd described above.

In another embodiment of the invention, enzyme V is selected from the group consisting of CYP76AH8 of SEQ ID NO:1, CYP76AH15 of SEQ ID NO:11, CYP76AH17 of SEQ ID NO:10 or a functional homologue of any of the aforementioned sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith. The sequence identity is preferably calculated as described herein below in the section "Sequence identity". A functional homologue of CYP76AH8, CYP76AH15 or CYP76AH17 may be a polypeptide also capable of catalysing reactions Vc and/or Vd described above.

VI. Enzyme Catalysing Transfer of an Acyl Group

The host organisms to be used with the present invention comprise one or more heterologous nucleic acids. Thus, the host organism may comprise a heterologous nucleic acid encoding an enzyme capable of catalysing transfer of an acyl group to an —OH of a hydroxylated 13R-MO and/or an oxidised hydroxylated-13R-MO.

Said enzyme may for example be any of the enzymes described herein in this section and may also be referred to herein as "enzyme VI". It is in particular preferred that the host organism comprises a heterologous nucleic acid encoding said enzyme, in embodiments of the invention, wherein the oxidised 13R-MO to be produced is substituted at one of the positions 1, 6, 7, 9 or 11 with —OR, wherein R preferably is acyl.

The enzyme VI may for example be capable of catalysing the following reaction VIa:

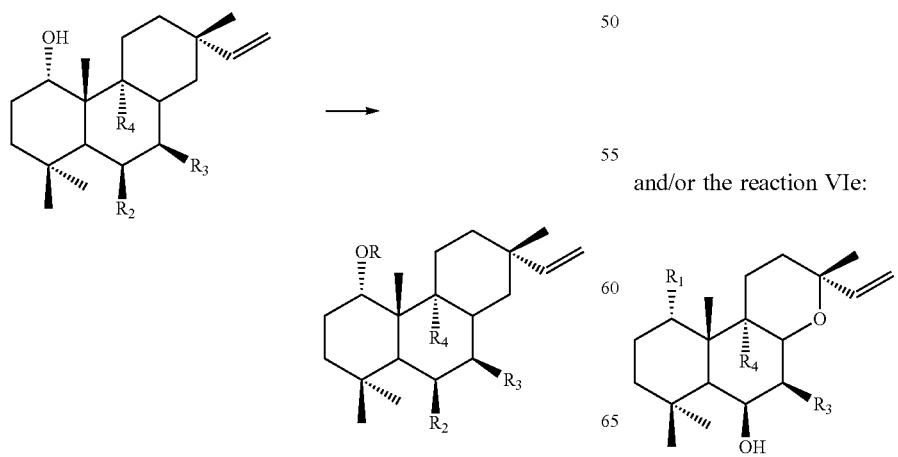

and/or the reaction VId:

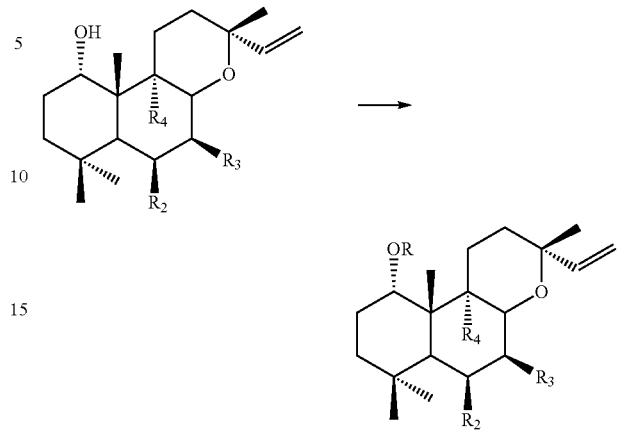

wherein R is acyl, more preferably R is acetyl and $R_2$, $R_3$ and $R_4$ individually are selected from the group consisting of —H, —OH and —OX, wherein X preferably is acyl. acyl is as defined in the section "Oxidised 13R-MO" herein below.

In particular, at least one of $R_2$, $R_3$ and $R_4$ is —H or —OH, for example at least two of $R_2$, $R_3$ and $R_4$ is —H or —OH, for example all of $R_2$, $R_3$ and $R_4$ is —H or —OH.

The enzyme VI may for example be capable of catalysing the following reaction VIb:

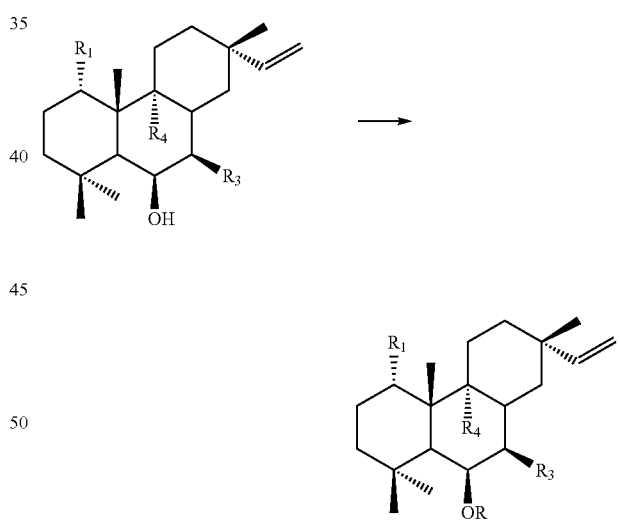

and/or the reaction VIe:

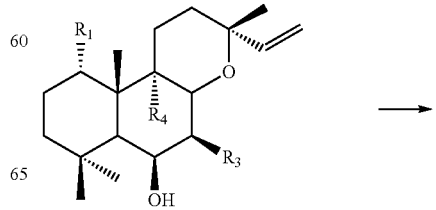

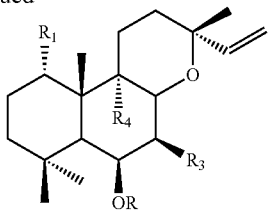

wherein R is acyl, more preferably R is acetyl and $R_1$, $R_3$ and $R_4$ individually are selected from the group consisting of —H, —OH and —OX, wherein X preferably is acyl. acyl is as defined in the section "Oxidised 13R-MO" herein below.

In particular, at least one of $R_1$, $R_3$ and $R_4$ is —H or —OH, for example at least two of $R_1$, $R_3$ and $R_4$ is —H or —OH, for example all of $R_1$, $R_3$ and $R_4$ is —H or —OH.

The enzyme VI may for example be capable of catalysing the following reaction VIc:

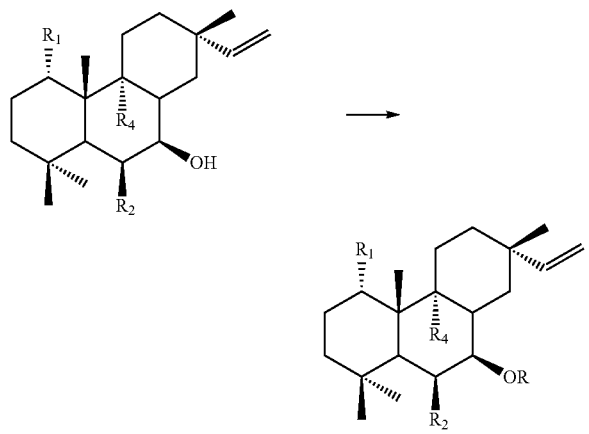

and/or the reaction VIf:

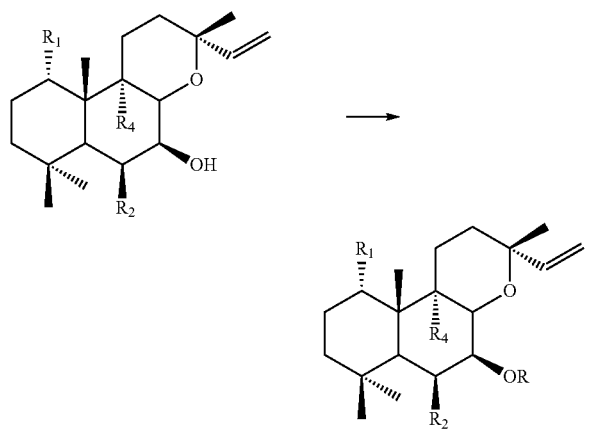

wherein R is acyl, more preferably R is acetyl and $R_1$, $R_2$ and $R_4$ individually are selected from the group consisting of —H, —OH and —OX, wherein X preferably is acyl. acyl is as defined in the section "Oxidised 13R-MO" herein below.

In particular, at least one of $R_1$, $R_2$ and $R_4$ is —H or —OH, for example at least two of $R_1$, $R_2$ and $R_4$ is —H or —OH, for example all of $R_1$, $R_2$ and $R_4$ is —H or —OH.

The enzyme VI may be capable of catalysing one or more of the reactions VIa, VIb, VIc, VId, VIe and VIf outlined above.

Enzyme VI may be any useful enzyme with above mentioned activities, in particular enzyme I may be an acyl transferase. Enzyme VI may be derived from any suitable source, but in a preferred embodiment enzyme VI is an enzyme from *Coleus forskohlii*. Thus enzyme VI may be a acyl transferase from *Coleus forskohlii*.

VII. Enzyme Catalysing Hydroxylation of 13R-MO at the 2 Position

The host organisms to be used with the present invention comprise one or more heterologous nucleic acids. Thus, the host organism may comprise a heterologous nucleic acid encoding an enzyme capable of catalysing hydroxylation of 13R-MO and/or oxidised 13R-MO at the 2 position, wherein said oxidised 13R-MO carries a —H at the 2-position.

Said enzyme may for example be any of the enzymes described herein in this section and may also be referred to herein as "enzyme VII". It is in particular preferred that the host organism comprises a heterologous nucleic acid encoding said enzyme, in embodiments of the invention, wherein the oxidised 13R-MO to be produced is substituted at least at the 2 position with —OH.

It is preferred that the enzyme VII is capable of catalysing the following reaction VII:

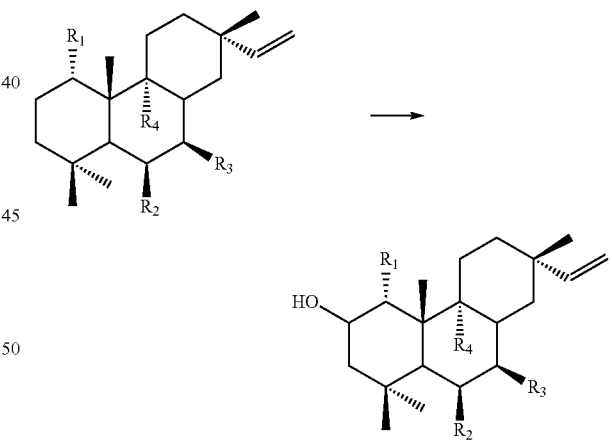

and/or reaction VIIb

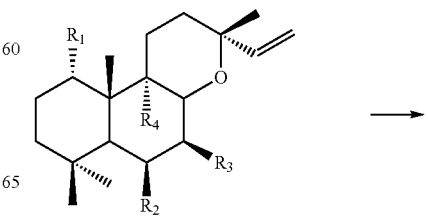

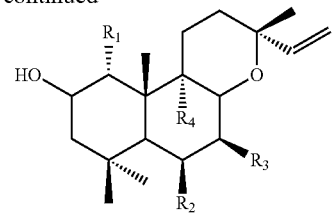

wherein $R_1$, $R_2$, $R_3$ and $R_4$ individually are selected from the group consisting of —H, —OH and —OR, wherein R preferably is acyl. Acyl is as defined in the section "Oxidised 13R-MO" herein below.

In particular, at least one of $R_1$, $R_2$, $R_3$ and $R_4$ is for example at least two of $R_1$, $R_2$, $R_3$ and $R_4$ are —H, for example all of $R_1$, $R_2$, $R_3$ and $R_4$ are —H.

Enzyme VII may be any useful enzyme with above mentioned activities, in particular enzyme VII may be a CYP450. Enzyme VII may be derived from any suitable source, but in a preferred embodiment enzyme VII is an enzyme from *Coleus forskohlii*. Thus enzyme VII may be a CYP450 from *Coleus forskohlii*.

In one embodiment of the invention, enzyme VII may be CYP71D381, such as CYP71D381 of SEQ ID NO:3 or a functional homologue of any of the aforementioned sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith.

The sequence identity is preferably calculated as described herein below in the section "Sequence identity". A functional homologue of CYP71D381 may be capable of catalysing reaction VII and/or reaction VIIb described above.

VIII. Enzyme Catalysing Hydroxylation of 13R-MO at the Methyl on the 10 Position The host organisms to be used with the present invention comprise one or more heterologous nucleic acids. Thus, the host organism may comprise a heterologous nucleic acid encoding an enzyme capable of catalysing hydroxylation of 13R-MO and/or oxidised 13R-MO on the methyl group at the 10 position, wherein said oxidised 13R-MO carries a —$CH_3$ at the 10-position.

Said enzyme may for example be any of the enzymes described herein in this section and may also be referred to herein as "enzyme VIII". It is in particular preferred that the host organism comprises a heterologous nucleic acid encoding said enzyme, in embodiments of the invention, wherein the oxidised 13R-MO to be produced is substituted with —OH at least on the methyl at the 10 position.

It is preferred that the enzyme VIII is capable of catalysing the following reaction VIII:

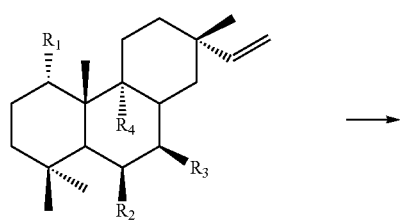

and/or reaction VIIIb

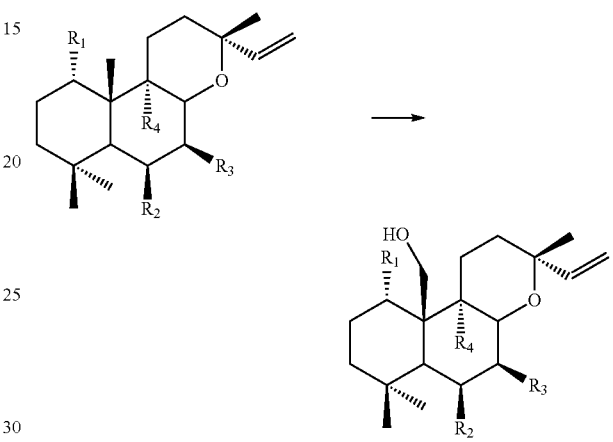

wherein $R_1$, $R_2$, $R_3$ and $R_4$ individually are selected from the group consisting of —H, —OH and —OR, wherein R preferably is acyl. Acyl is as defined in the section "Oxidised 13R-MO" herein below.

In particular, at least one of $R_1$, $R_2$, $R_3$ and $R_4$ is —H, for example at least two of $R_1$, $R_2$, $R_3$ and $R_4$ are —H, for example all of $R_1$, $R_2$, $R_3$ and $R_4$ are —H.

Enzyme VIII may be any useful enzyme with above mentioned activities, in particular enzyme VIII may be a CYP450. Enzyme VIII may be derived from any suitable source, but in a preferred embodiment enzyme VIII is an enzyme from *Coleus forskohlii*. Thus enzyme VIII may be a CYP450 from *Coleus forskohlii*.

In one embodiment of the invention, enzyme VIII may be CYP71D381, such as CYP71D381 of SEQ ID NO:3 or a functional homologue of any of the aforementioned sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith.

The sequence identity is preferably calculated as described herein below in the section "Sequence identity". A functional homologue of CYP71D381 may be capable of catalysing reaction VIII described above.

IX. TPS2

In addition to the heterologous nucleic acids I, II, III, IV, V and/or VI, the host organism may comprise a heterologous nucleic acid encoding TPS2. It is preferred that in embodiments of the invention where the host organism comprises a nucleic acid encoding TPS2, then the host organism also comprises a heterologous nucleic acid encoding either TPS3 or TPS4.

Said TPS2 may for example be any of the enzymes described herein in this section and may also be referred to herein as "enzyme IX".

Preferably said TPS2 is an enzyme capable of catalysing the reaction IX:

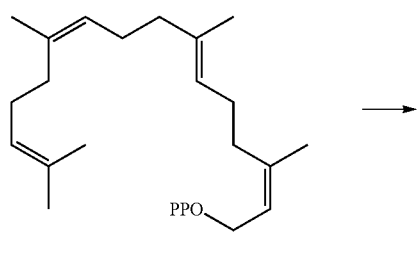

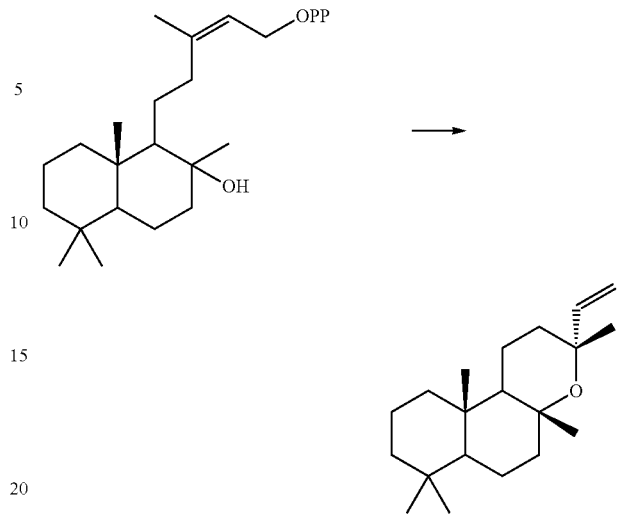

wherein —OPP refers to diphosphate.

In particular, it is preferred that said TPS2 is TPS2 of *Coleus forskohlii*. In particular, said enzyme IX may be a polypeptide of SEQ ID NO:7 or a functional homologue thereof sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith.

The sequence identity is preferably calculated as described herein below in the section "Sequence identity". A functional homologue of a TPS2 is a polypeptide, which is also capable of catalysing reaction IX described above.

X. TPS3

In addition to the heterologous nucleic acids I, II, III, IV, V and/or VI, the host organism may comprise a heterologous nucleic acid encoding TPS3. It is preferred that in embodiments of the invention where the host organism comprises a nucleic acid encoding TPS3, then the host organism also comprises a heterologous nucleic acid encoding TPS2.

Said TPS3 may for example be any of the enzymes described herein in this section and may also be referred to herein as "enzyme X".

Preferably said TPS3 is an enzyme capable of catalysing the reaction X:

In particular, it is preferred that said TPS3 is TPS3 of *Coleus forskohlii*. In particular, said enzyme X may be a polypeptide of SEQ ID NO:8 or a functional homologue thereof sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith.

The sequence identity is preferably calculated as described herein below in the section "Sequence identity". A functional homologue of a TPS3 is a polypeptide, which is also capable of catalysing reaction X described above.

XI. TPS4

In addition to the heterologous nucleic acids I, II, III, IV, V and/or VI, the host organism may comprise a heterologous nucleic acid encoding TPS4. It is preferred that in embodiments of the invention where the host organism comprises a nucleic acid encoding TPS4, then the host organism also comprises a heterologous nucleic acid encoding TPS2.

Said TPS4 may for example be any of the enzymes described herein in this section and may also be referred to herein as "enzyme XI".

Preferably said TPS4 is an enzyme capable of catalysing the reaction XI:

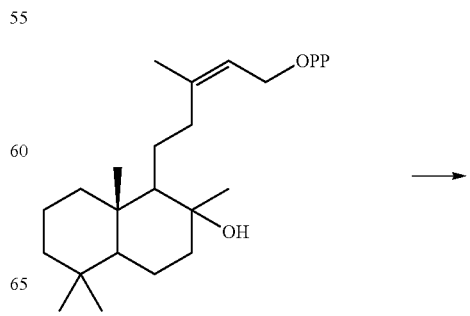

-continued

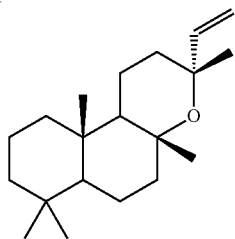

In particular, it is preferred that said TPS4 is TPS4 of *Coleus forskohlii*. In particular, said enzyme XI may be a polypeptide of SEQ ID NO:9 or a functional homologue thereof sharing at least 70%, such as at least 80%, for example at least 75%, such as at least 80%, such as at least 85%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity therewith.

The sequence identity is preferably calculated as described herein below in the section "Sequence identity". A functional homologue of a TPS4 is a polypeptide, which is also capable of catalysing reaction XI described above.

Sequence Identity

A high level of sequence identity indicates likelihood that the first sequence is derived from the second sequence. Amino acid sequence identity requires identical amino acid sequences between two aligned sequences. Thus, a candidate sequence sharing 80% amino acid identity with a reference sequence, requires that, following alignment, 80% of the amino acids in the candidate sequence are identical to the corresponding amino acids in the reference sequence. Identity according to the present invention is determined by aid of computer analysis, such as, without limitations, the ClustalW computer alignment program (Higgins D., Thompson J., Gibson T., Thompson J. D., Higgins D. G., Gibson T. J., 1994. CLUSTAL W: improving the sensitivity of progressive multiple sequence alignment through sequence weighting, position-specific gap penalties and weight matrix choice. Nucleic Acids Res. 22:4673-4680), and the default parameters suggested therein. The ClustalW software is available from as a ClustalW WWW Service at the European Bioinformatics Institute http://www.ebi.ac.uk/clustalw. Using this program with its default settings, the mature (bioactive) part of a query and a reference polypeptide are aligned. The number of fully conserved residues are counted and divided by the length of the reference polypeptide.

The ClustalW algorithm may similarly be used to align nucleotide sequences. Sequence identities may be calculated in a similar way as indicated for amino acid sequences. In one important embodiment, the cell of the present invention comprises a nucleic acid sequence coding, as define herein.

Heterologous Nucleic Acid

The term "heterologous nucleic acid" as used herein refers to a nucleic acid sequence, which has been introduced into the host organism, wherein said host does not endogenously comprise said nucleic acid. For example, said heterologous nucleic acid may be introduced into the host organism by recombinant methods. Thus, the genome of the host organism has been augmented by at least one incorporated heterologous nucleic acid sequence. It will be appreciated that typically the genome of a recombinant host described herein is augmented through the stable introduction of one or more heterologous nucleic acids encoding one or more enzymes.

Suitable host organisms include microorganisms, plant cells, and plants, and may for example be any of the host organisms described herein below in the section "Host organism".

In general the heterologous nucleic acid encoding a polypeptide (also referred to as "coding sequence" in the following) is operably linked in sense orientation to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned at further distance, for example as much as about 5,000 nucleotides upstream of the translation initiation site, or about 2,000 nucleotides upstream of the transcription start site.

The choice of regulatory regions to be included depends upon several factors, including the type of host organism. It is a routine matter for one of skill in the art to modulate the expression of a coding sequence by appropriately selecting and positioning regulatory regions relative to the coding sequence. It will be understood that more than one regulatory region may be present, e.g., introns, enhancers, upstream activation regions, transcription terminators, and inducible elements.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host organisms obtained, using appropriate codon bias tables for that host (e.g., microorganism).

Nucleic acids may also be optimized to a GC-content preferable to a particular host, and/or to reduce the number of repeat sequences. As isolated nucleic acids, these modified sequences can exist as purified molecules and can be incorporated into a vector or a virus for use in constructing modules for recombinant nucleic acid constructs.

A non-limiting example of a heterologous nucleic acid encoding CYP76AH8 is provided herein as SEQ ID NO:5. Thus, the heterologous nucleic acid encoding enzyme I may comprise or consist of SEQ ID NO:5 or a sequence sharing at least 70%, such as at least 80%, for example at least 90%, such as at least 95% sequence identity therewith. Said heterologous nucleic acid is particularly useful in embodiments of the invention where the host is a yeast cell, such as S. cerevisiae.

A non-limiting example of a heterologous nucleic acid encoding CYP76AH11 is provided herein as SEQ ID NO:6. Thus, the heterologous nucleic acid encoding enzyme II, enzyme III or enzyme may comprise or consist of SEQ ID NO:6 or a sequence sharing at least 70%, such as at least 80%, for example at least 90%, such as at least 95% sequence identity therewith. Said heterologous nucleic acid is particularly useful in embodiments of the invention where the host is a yeast cell, such as S. cerevisiae.

Oxidised 13R-MO

The present invention relates to methods for producing forskolin and related compounds. In particular, the invention relates to methods for producing oxidised 13R-MO.

The term "oxidised 13R-MO" as used herein refers to 13R-manoyl-oxide (13R-MO) substituted at one or more positions with a moiety selected from the group consisting of =O, —OH and OR, wherein R preferably is acyl.

The term "substituted with a moiety" as used herein in relation to chemical compounds refers to hydrogen group(s) being substituted with said moiety.

The term "acyl" as used herein denoted a substituent of the formula —(C=O)-alkyl. "Alkyl" as used herein refers to a saturated, straight or branched hydrocarbon chain. The hydrocarbon chain preferably contains of from one to eighteen carbon atoms ($C_{1-18}$-alkyl), more preferred of from one to six carbon atoms ($C_{1-8}$-alkyl), including methyl, ethyl, propyl, isopropyl, butyl, isobutyl, secondary butyl, tertiary butyl, pentyl, isopentyl, neopentyl, tertiary pentyl, hexyl and isohexyl. In a preferred embodiment alkyl represents a $C_{1-3}$-alkyl group, which may in particular include methyl, ethyl, propyl or isopropyl. In another preferred embodiment of this invention alkyl represents methyl.

The term "oxo" as used herein refers to a "=O" substituent.

The term "keto-" as used herein is used as a prefix to indicate possession of a carbonyl (C=O) group.

The term "hydroxyl" as used herein refers to a "—OH" substituent.

The structure of 13R-manoyl-oxide (13R-MO) is provided below. The structure also provides the numbering of the carbon atoms of the ring structure used herein.

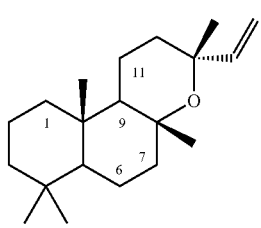 [SMILES: C=C[C@@]1(C)CCC2[C@@]3(C)CCCC(C)(C)C3CC[C@@]2(C)O1]

Preferably, the oxidised 13R-MO according to the present invention, is 13R-MO substituted at one or more of the positions 1, 6, 7, 9 and/or 11 with a moiety selected from the group consisting of =O, —OH and OR, wherein R preferably is acyl.

In another embodiment of the invention the oxidised 13R-MO is 13R-MO substituted at the 2 position with —OH. In yet another embodiment of the invention the oxidised 13R-MO is 13R-MO substituted on the methyl at the 10 position with —OH. Thus, the substituent on the 1 position may be —CH$_2$—OH.

Thus, for example the oxidised 13R-MO may be a compound of formula III:

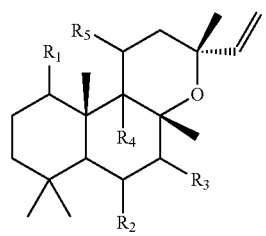

wherein $R_1$, $R_2$, $R_3$, $R_4$ and $R_5$ individually are selected from the group consisting of, —H=O, —OH and —OR, wherein R preferably is acyl, more preferably R is —(C=O)—CH$_3$.

For example, $R_1$ may be selected from the group consisting of —OH, —H and =O.

For example $R_2$ may be selected from the group consisting of —OH and —O-acyl, for example $R_2$ may be selected from the group consisting of —OH and —O—(C=O)—CH$_3$.

For example $R_3$ may be selected from the group consisting of —OH and —O-acyl, for example $R_3$ may be selected from the group consisting of —OH and —O—(C=O)—CH$_3$.

For example $R_4$ may be selected from the group consisting of —H and —OH.

For example $R_5$ may be selected from the group consisting of =O and —O-acyl, for example $R_5$ may be selected from the group consisting of =O and —O—(C=O)—CH$_3$.

In particular, the oxidised 13R-MO may be 13R-MO, which is substituted at the 11 position with =O. In addition, to said substitution, the oxidised 13R-MO may be substituted at one or more of the positions 1, 6, 7 and 9 with a moiety selected from the group consisting of =O, —OH and OR, preferably with a moiety selected from the group consisting of =O, —OH and —OR. R may be acyl, wherein acyl is as defined above.

Thus, in one embodiment of the invention said oxidised 13R-MO is a compound of the formula I

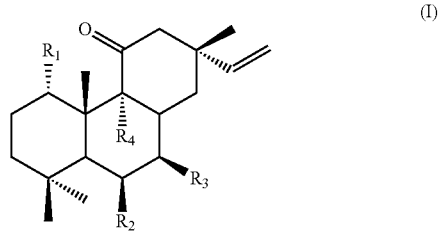

wherein $R_1$, $R_2$, $R_3$ and $R_4$ individually are selected from the group consisting of —H, —OH and —OR, wherein R preferably is acyl, wherein acyl is as defined above. It is preferred that at least one of $R_1$, $R_2$, $R_3$ and $R_4$ is —OH or —OR, more preferably at least two of $R_1$, $R_2$, $R_3$ and $R_4$ is —OH or —OR, for example at least three of least one of $R_1$, $R_2$, $R_3$ and $R_4$ is —OH or —OR, for example all of $R_1$, $R_2$, $R_3$ and $R_4$ is —OH or —OR.

$R_1$ may be selected from the group consisting of —H, —OH and —OR, wherein R is as defined above. Preferably, $R_1$ is selected from the group consisting of —H and —OH, in particular $R_1$ may be —OH.

$R_2$ may be selected from the group consisting of —H, —OH and —OR, wherein R is as defined above. Preferably, $R_2$ is selected from the group consisting of —OR and —OH, wherein R is as defined above. For example $R_2$ may be selected from the group consisting of —O—(C=O)—$CH_3$ (acetyl), —O—(C=O)—$CH_2$—$CH_3$, —O—(C=O)—$CH_2$—$CH_2$—$CH_3$ and —OH. In particular, $R_2$ may be —OH.

$R_3$ may be selected from the group consisting of —H, —OH and —OR, wherein R is as defined above. Preferably, $R_3$ is selected from the group consisting of —OR and —OH, wherein R is as defined above. For example $R_3$ may be selected from the group consisting of —O—(C=O)—$CH_3$ (acetyl), —O—(C=O)—$CH_2$—$CH_3$, —O—(C=O)—$CH_2$—$CH_2$—$CH_3$ and —OH. In particular, $R_3$ may be acetyl.

$R_4$ may be selected from the group consisting of —H, —OH and —OR, wherein R is as defined above. Preferably, $R_4$ is selected from the group consisting of —H and —OH, in particular $R_4$ may be —OH.

It is also comprised within the invention that the oxidised 13R-MO is not substituted at the 11 position. Thus, the oxidised 13R-MO may be a compound of the formula (II)

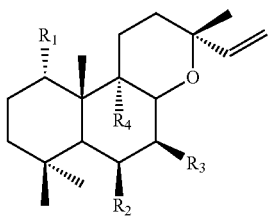

wherein each of $R_1$, $R_2$, $R_3$ and $R_4$ may be as indicated herein above in relation to compounds of formula I.

Figure 8:
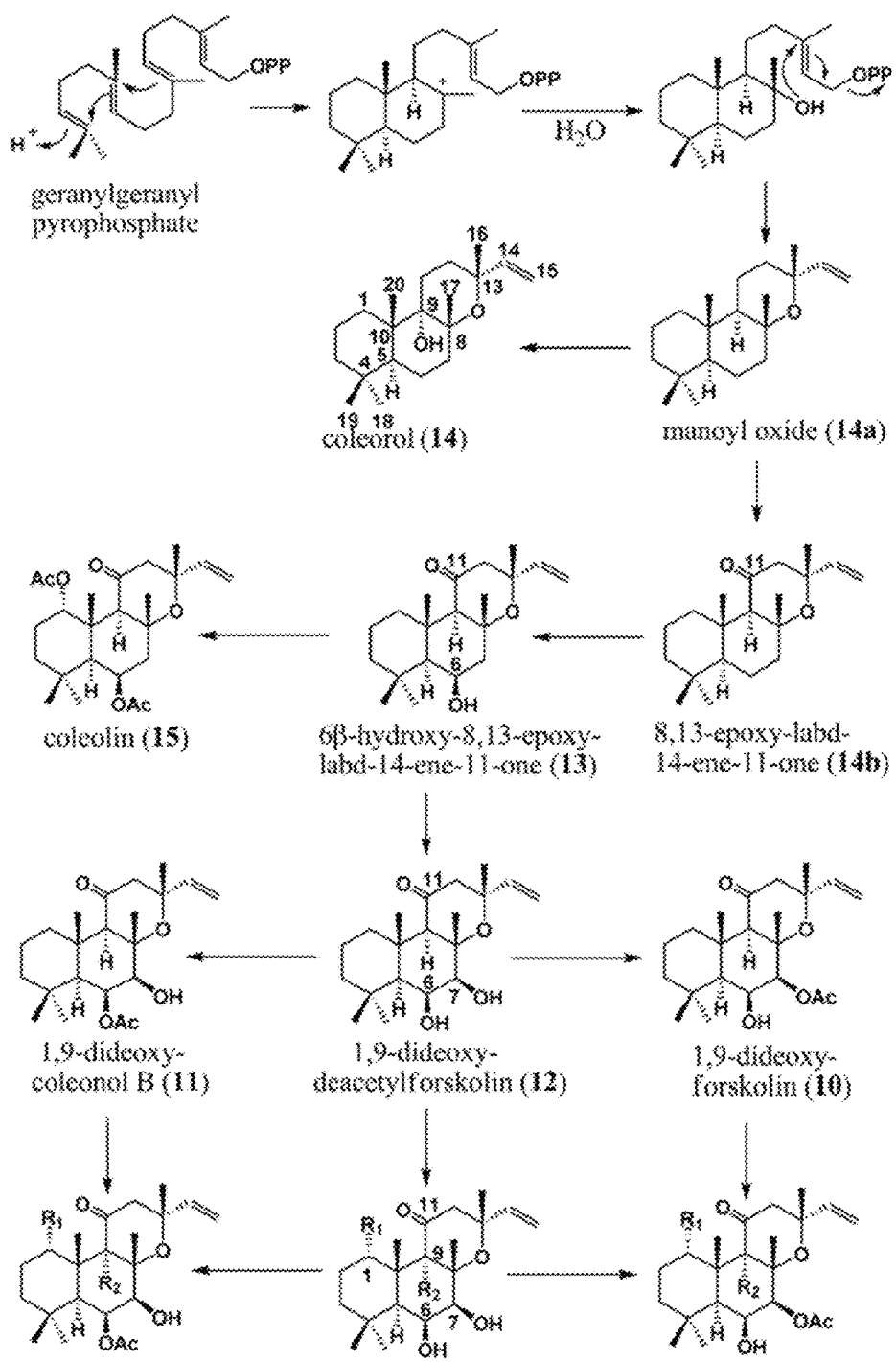
FIG. 8 shows a proposed biosynthetic route to forskolin in *C. forskohlii* proposed by Asada et al., Phytochemistry 79 (2012) 141-146.
Figure 8:
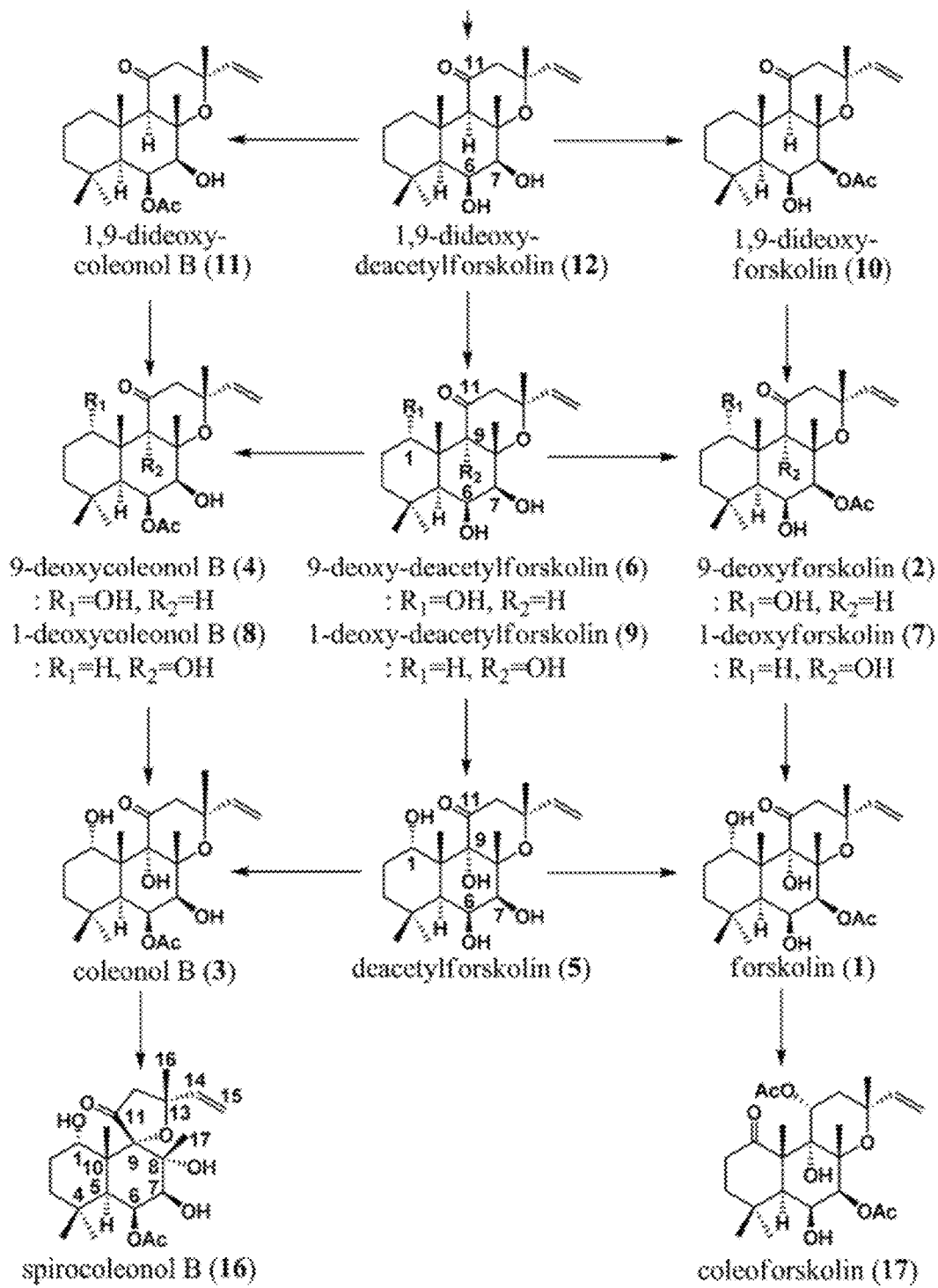

For example, the oxidised 13R-MO may be selected from the group consisting of compounds 1, 2, 3, 4, 5, 6, 7, 8, 9, 10, 11, 12, 13, 14b and 15 shown in FIG. 8.

Figure 7:
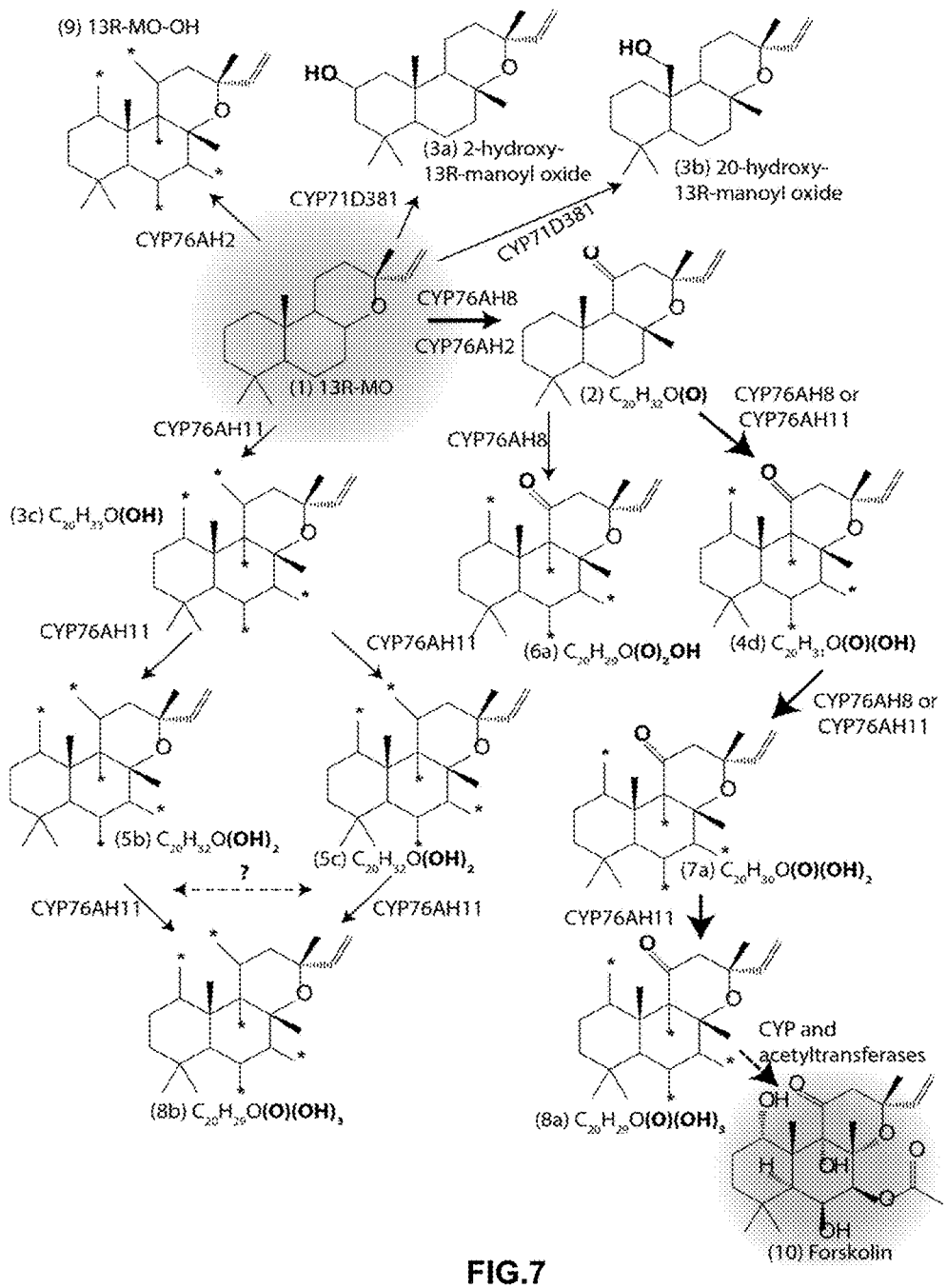
FIG. 7 shows selected observed oxidation reactions of 13R-MO en route to forskolin and other pharmacological relevant 13R-MO derived compounds. CYP76AH8 and CYP76AH11 effectively catalyse the first four reactions, towards forskolin. CYP71D381, CYP76AH9 and CYP76AH11 catalyse hydroxylation reactions of 13R-MO towards other 13R-MO derived compounds with potential pharmacological relevance. With respect to compound 6a * indicates possible position of =O or —OH group(s). With respect to all other compounds * indicates possible position of —OH group(s).

The oxidised 13R-MO may also be any of the oxidised 13R-MO shown in FIG. 7, such as compounds 2, 3a, 3b, 4, 5, 6, 7a, 7b, 8, 9, 10 or 11 of FIG. 7.

Figure 6:
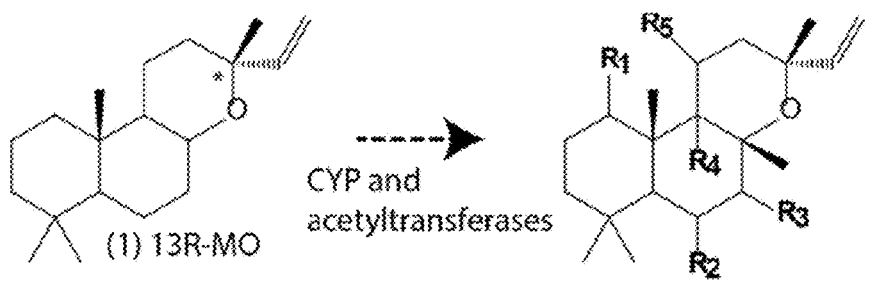
FIG. 6 shows 13R-manoyl-oxide and oxidised 13R-manoyl-oxides found in *C. forskohlii* and that have pharmaceutical properties.

In particular, the oxidised 13R-MO may be selected from the group consisting of forskolin, iso-forskolin, forskolin B, forskolin D, 9-deoxyforskolin, 1,9-dideoxyforskolin and coleoforskolin. The structures of these compounds are provided in FIG. 6.

In a preferred embodiment of the invention, the invention relates to methods for producing forskolin. The term "forskolin" as used herein refers to a compound of the formula

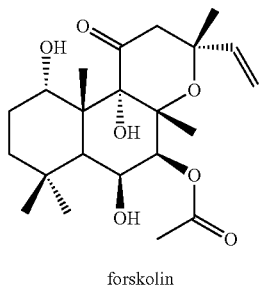

forskolin

Host Organism

The host organism to be used with the methods of the invention, may be any suitable host organism containing one or more of the heterologous nucleic acids I., II., III., IV., V. and/or VI. described herein above.

Suitable host organisms include microorganisms, plant cells, and plants.

The microorganism can be any microorganism suitable for expression of heterologous nucleic acids. In one embodiment the host organism of the invention is a eukaryotic cell. In another embodiment the host organism is a prokaryotic cell.

In a preferred embodiment, the host organism is a fungal cell such as a yeast or filamentous fungus. In particular the host organism may be a yeast cell.

In a further embodiment the yeast cell is selected from the group consisting of *Saccharomyces cerevisiae, Schizosaccharomyces pombe, Yarrowia lipolytica, Candida glabrata, Ashbya gossypii, Cyberlindnera jadinii,* and *Candida albicans*.

In general, yeasts and fungi are excellent microorganism to be used with the present invention. They offer a desired ease of genetic manipulation and rapid growth to high cell densities on inexpensive media. For instance yeasts grow on a wide range of carbon sources and are not restricted to glucose. Thus, the microorganism to be used with the present invention may be selected from the group of yeasts described below:

*Arxula adeninivorans* (Blastobotrys adeninivorans) is a dimorphic yeast (it grows as a budding yeast like the baker's yeast up to a temperature of 42° C., above this threshold it grows in a filamentous form) with unusual biochemical characteristics. It can grow on a wide range of substrates and can assimilate nitrate. It has successfully been applied to the generation of strains that can produce natural plastics or the development of a biosensor for estrogens in environmental samples.

*Candida boidinii* is a methylotrophic yeast (it can grow on methanol). Like other methylotrophic species such as *Hansenula polymorpha* and *Pichia pastoris*, it provides an excellent platform for the production of heterologous proteins. Yields in a multigram range of a secreted foreign protein have been reported. A computational method, IPRO, recently predicted mutations that experimentally switched the cofactor specificity of *Candida boidinii* xylose reductase from NADPH to NADH. Details on how to download the software implemented in Python and experimental testing of predictions are outlined in the following paper.

*Hansenula polymorpha* (*Pichia angusta*) is another methylotrophic yeast (see *Candida boidinii*). It can furthermore grow on a wide range of other substrates; it is thermo-tolerant and can assimilate nitrate (see also *Kluyveromyces lactis*). It has been applied to the production of hepatitis B vaccines, insulin and interferon alpha-2a for the treatment of hepatitis C, furthermore to a range of technical enzymes.

*Kluyveromyces lactis* is a yeast regularly applied to the production of kefir. It can grow on several sugars, most importantly on lactose which is present in milk and whey. It has successfully been applied among others to the production of chymosin (an enzyme that is usually present in the stomach of calves) for the production of cheese. Production takes place in fermenters on a 40,000 L scale.

*Pichia pastoris* is a methylotrophic yeast (see *Candida boidinii* and *Hansenula polymorpha*). It provides an efficient platform for the production of foreign proteins. Platform elements are available as a kit and it is worldwide used in academia for the production of proteins. Strains have been engineered that can produce complex human N-glycan (yeast glycans are similar but not identical to those found in humans).

*Saccharomyces cerevisiae* is the traditional baker's yeast known for its use in brewing and baking and for the production of alcohol. As protein factory it has successfully been applied to the production of technical enzymes and of pharmaceuticals like insulin and hepatitis B vaccines. Also it has been useful for production of terpenoids.

*Yarrowia lipolytica* is a dimorphic yeast (see *Arxula adeninivorans*) that can grow on a wide range of substrates. It has a high potential for industrial applications but there are no recombinant products commercially available yet.

In another embodiment the host organism is a microalgae such as *Chlorella* and *Prototheca*.

In another embodiment of the invention the host organism is a filamentous fungus, for example *Aspergillus*.

In further yet another embodiment the host organism is a plant cell. The host organism may be a cell of a higher plant, but the host organism may also be cells from organisms not belonging to higher plants for example cells from the moss *Physcomitrella patens*.

In another embodiment the host organism is a mammalian cell, such as a human, feline, porcine, simian, canine, murine, rat, mouse or rabbit cell.

As mentioned, the host organism can also be a prokaryotic cell such as a bacterial cell. If the host organism is a prokaryotic cell the cell may be selected from, but not limited to *E. coli, Corynebacterium, Bacillus, Pseudomonas* and *Streptomyces* cells.

The host organism may also be a plant.

A plant or plant cell can be transformed by having a heterologous nucleic acid integrated into its genome, i.e., it can be stably transformed. Stably transformed cells typically retain the introduced nucleic acid with each cell division. A plant or plant cell can also be transiently transformed such that the recombinant gene is not integrated into its genome. Transiently transformed cells typically lose all or some portion of the introduced nucleic acid with each cell division such that the introduced nucleic acid cannot be detected in daughter cells after a certain number of cell divisions. Both transiently transformed and stably transformed transgenic plants and plant cells can be useful in the methods described herein.

Plant cells comprising a heterologous nucleic acid used in methods described herein can constitute part or all of a whole plant. Such plants can be grown in a manner suitable for the species under consideration, either in a growth chamber, a greenhouse, or in a field. Plants may also be progeny of an initial plant comprising a heterologous nucleic acid provided the progeny inherits the heterologous nucleic acid. Seeds produced by a transgenic plant can be grown and then selfed (or outcrossed and selfed) to obtain seeds homozygous for the nucleic acid construct.

The plants to be used with the invention can be grown in suspension culture, or tissue or organ culture. For the purposes of this invention, solid and/or liquid tissue culture techniques can be used. When using solid medium, plant cells can be placed directly onto the medium or can be placed onto a filter that is then placed in contact with the medium. When using liquid medium, transgenic plant cells can be placed onto a flotation device, e.g., a porous membrane that contacts the liquid medium.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation, U.S. Pat. Nos. 5,538,880; 5,204,253; 6,329,571; and 6,013,863. If a cell or cultured tissue is used as the recipient tissue for transformation, plants can be regenerated from transformed cultures if desired, by techniques known to those skilled in the art.

The plant comprising a heterologous nucleic acid to be used with the present invention may for example be selected from: corn (*Zea. mays*), canola (*Brassica napus, Brassica rapa* ssp.), alfalfa (*Medicago sativa*), rice (*Oryza sativa*), rye (*Secale cerale*), sorghum (*Sorghum bicolor, Sorghum vulgare*), sunflower (*Helianthus annuas*), wheat (*Tritium aestivum* and other species), Triticale, Rye (*Secale*) soybean (*Glycine max*), tobacco (*Nicotiana tabacum*), potato (*Solanum tuberosum*), peanuts (*Arachis hypogaea*), cotton (*Gossypium hirsutum*), sweet potato (*Impomoea batatus*), cassava (*Manihot esculenta*), coffee (*Cofea* spp.), coconut (*Cocos nucifera*), pineapple (*Anana comosus*), citrus (*Citrus* spp.) cocoa (*Theobroma cacao*), tea (*Camellia senensis*), banana (*Musa* spp.), avacado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Primus amygdalus*), apple (*Malus* spp), Pear (*Pyrus* spp), plum and cherry tree (*Prunus* spp), *Ribes* (currant etc.), *Vitis*, Jerusalem artichoke (*Helianthemum* spp), non-cereal grasses (Grass family), sugar and fodder beets (*Beta vulgaris*), chicory, oats, barley, vegetables, and ornamentals.

For example, plants of the present invention are crop plants (for example, cereals and pulses, maize, wheat, potatoes, tapioca, rice, *sorghum*, millet, cassava, barley, pea, sugar beets, sugar cane, soybean, oilseed rape, sunflower and other root, tuber or seed crops. Other important plants maybe fruit trees, crop trees, forest trees or plants grown for their use as spices or pharmaceutical products (*Mentha* spp, clove, *Artemesia* spp, *Thymus* spp, *Lavendula* spp, *Allium* spp., *Hypericum, Catharanthus* spp, *Vinca* spp, *Papaver* spp., *Digitalis* spp, *Rawolfia* spp., *Vanilla* spp., *Petrusilium* spp., *Eucalyptus*, tea tree, *Picea* spp, *Pinus* spp, *Abies* spp, *Juniperus* spp.

Horticultural plants which may be used with the present invention may include lettuce, endive, and vegetable brassicas including cabbage, broccoli, and cauliflower, carrots, and carnations and geraniums.

The plant may also be selected from the group consisting of tobacco, cucurbits, carrot, strawberry, sunflower, tomato, pepper and *Chrysanthemum*.

The plant may also be a grain plants for example oil-seed plants or leguminous plants. Seeds of interest include grain seeds, such as corn, wheat, barley, *sorghum*, rye, etc. Oil-seed plants include cotton soybean, safflower, sunflower, *Brassica*, maize, alfalfa, palm, coconut, etc. Leguminous plants include beans and peas. Beans include guar, locust bean, fenugreek, soybean, garden beans, cowpea, mung bean, lima bean, fava bean, lentils, chickpea.

In a further embodiment of the invention said plant is selected from the following group: maize, rice, wheat, sugar beet, sugar cane, tobacco, oil seed rape, potato and soybean. Thus, the plant may for example be rice.

In one embodiment the plant is tobacco.

The whole genome of *Arabidopsis thaliana* plant has been sequenced (The *Arabidopsis* Genome Initiative (2000). "Analysis of the genome sequence of the flowering plant *Arabidopsis thaliana*". Nature 408 (6814): 796-815. doi: 10.1038/35048692. PMID 11130711). Consequently, very detailed knowledge is available for this plant and it may therefore be a useful plant to work with.

Accordingly, one plant, which may be used with the present invention is an *Arabidopsis* and in particular an *Arabidopsis thaliana*.

It may be preferred that the plant is not *Coleus forskohlii*.

In one embodiment of the invention, the host organism may comprise at least the following heterologous nucleic acids:
a) a heterologous nucleic acid encoding CYP76AH8 of SEQ ID NO:1, CYP76AH15 of SEQ ID NO:11, CYP76AH17 of SEQ ID NO:10 or a functional homologue of any of the aforementioned sharing at least 70%, such as at least 80%, such as at least 85%, such as at least 90%, such as at least 95%, such as at least 98%, such as at least 99% sequence identity therewith.

In one embodiment of the invention, the host organism may comprise at least the following heterologous nucleic acids:
a) a heterologous nucleic acid encoding CYP76AH11 of SEQ ID NO:2 or a functional homologue thereof sharing at least 70%, such as at least 80%, such as at least 85%, such as at least 90%, such as at least 95%, such as at least 98%, such as at least 99% sequence identity therewith.

In one embodiment of the invention, the host organism may comprise at least the following heterologous nucleic acids:
a) a heterologous nucleic acid encoding CYP76AH8 of SEQ ID NO:1, CYP76AH15 of SEQ ID NO:11, CYP76AH17 of SEQ ID NO:10 or a functional homologue of any of the aforementioned sharing at least 70%, such as at least 80%, such as at least 85%, such as at least 90%, such as at least 95%, such as at least 98%, such as at least 99% sequence identity therewith; and
b) a heterologous nucleic acid encoding CYP76AH11 of SEQ ID NO:2 or a functional homologue thereof sharing at least 70%, such as at least 80%, such as at least 85%, such as at least 90%, such as at least 95%, such as at least 98%, such as at least 99% sequence identity therewith.

In one embodiment of the invention, the host organism may comprise at least the following heterologous nucleic acids:
a) a heterologous nucleic acid encoding CYP76AH8 of SEQ ID NO:1, CYP76AH15 of SEQ ID NO:11, CYP76AH17 of SEQ ID NO:10 or a functional homologue of any of the aforementioned sharing at least 70%, such as at least 80%, such as at least 85%, such as at least 90%, such as at least 95%, such as at least 98%, such as at least 99% sequence identity therewith; and
b) a heterologous nucleic acid encoding CYP76AH11 of SEQ ID NO:2 or a functional homologue thereof sharing at least 70%, such as at least 80%, such as at least 85%, such as at least 90%, such as at least 95%, such as at least 98%, such as at least 99% sequence identity therewith; and
c) a heterologous nucleic acid encoding TPS2 of SEQ ID NO:7 or a functional homologue thereof sharing at least 70%, such as at least 80%, such as at least 85%, such as at least 90%, such as at least 95%, such as at least 98%, such as at least 99% sequence identity therewith; and
d) a heterologous nucleic acid encoding TPS3 of SEQ ID NO:8, TPS4 of SEQ ID NO:9 or a functional homologue of any of the aforementioned sharing at least 70%, such as at least 80%, such as at least 85%, such as at least 90%, such as at least 95%, such as at least 98%, such as at least 99% sequence identity therewith.

SEQUENCE LISTING

```
amino acid sequence of CfCYP76AH8
                                                    SEQ ID NO: 1
METITLLLALFFIALTYFISSRRRRNLPPGPFPLPIIGNMLQLGSKPHQSFAQLSKKYGPL

MSIHLGSLYTVIVSSPEMAKEILQKHGQVFSGRTIAQAVHACDHDKISMGFLPVANTW

RDMRKICKEQMFSHHSLEASEELRHQKLQQLLDYAQKCCEAGRAVDIREASFITTLNL

MSATMFSTQATEFDSEATKEFKEIIEGVATIVGVANFADYFPILKPFDLQGIKRRADGYF

GRLLKLIEGYLNERLESRRLNPDAPRKKDFLETLVDIIEANEYKLTTEHLTHLMLDLFVG

GSETNTTSLEWIMSELVINPDKMAKVKEELKSVVGDEKLVNESDMPRLPYLQAVIKEV

LRIHPPGPLLLPRKAESDQVVNGYLIPKGTQILFNAWAMGRDPTIWKDPESFEPERFL
```

-continued

NQSIDFKGQDFELIPFGSRRICPGMPLANRILHMTTATLVHNFDWKLEEGTADADHK

GELFGLAVRRATPLRIIPLKP amino acid sequence of CfCYP76AH11
SEQ ID NO: 2

MELVQVIAVVAVVVVLWSQLKRKGRKLPPGPSPLPIVGNIFQLSGKNINESFAKLSKIY

GPVMSLRLGSLLTVIISSPEMAKEVLTSKDFANRPLTEAAHAHGHSKFSVGFVPVSDP

KWKQMRRVCQEEMFASRILENSQQRRHQKLQELIDHVQESRDAGRAVTIRDPVFATT

LNIMSLTLFSADATEFSSSATAELRDIMAGVVSVLGAANLADFFPILKYFDPQGMRRKA

DLHYGRLIDHIKSRMDKRSELKKANPNHPKHDDFLEKIIDITIQRNYDLTINEITHLLVDL

YLAGSESTVMTIEWTMAELMLRPESLAKLKAELRSVMGERKMIQESDDISRLPYLNGA

IKEALRLHPPGPLLFARKSEIDVELSGYFIPKGTQILVNEWGMGRDPSVWPNPECFQP

ERFLDKNIDYKGQDPQLIPFGAGRRICPGIPIAHRVVHSVVAALVHNFDWEFAPGGSQ

CNNEFFTGAALVREVPLKLIPLNPPSI amino acid sequence of CfCYP71D381
SEQ ID NO: 3

MEFDFPSALIFPAVSLLLLLWLTKTRKPKSDLDRIPGPRRLPLIGNLHHLISLTPPPRLFR

EMAAKYGPLMRLQLGGVPFLIVSSVDVAKHVVKTNDVPFANRPPMHAARAITYNYTDI

GFAPYGEYWRNLRKICTLELLSARRVRSFRHIREEENAGVAKWIASKEGSPANLSERV

YLSSFDITSRASIGKATEEKQTLTSSIKDAMKLGGFNVADLYPSSKLLLLITGLNFRIQRV

FRKTDRILDDLLSQHRSTSATTERPEDLVDVLLKYQKEETEVHLNNDKIKAVIMDMFLA

GGETSATAVDWAMAEMIRNPTTLKKAQEEVRRVFDGKGYVDEEEFHELKYLKLVIKE

MLRMHPPLPFLVPRMNSERCEINGYEIPANTRLLINAWAIGRPKYWNDAEKFIPERFE

NSSIDFKGNNLEYIPFGAGRRMCPGMTFGLASVEFTLAMLLYHFDWKMPQGIKLDMT

ESFGASLKRKHDLLMIPTLKRPLRLAP amino acid sequence of CfCYP76AH9
SEQ ID NO: 4

MDFFTLLAALFLITLTFFLFFKSESKRRGGANLPPGPYPLPIVGNIFQLGKKPHQSLAQL

AKIHGPLMSLHFGSVYTVIVTSPEMAKEIFVKNDQAFLNRTVVEAVHAHDHDKISMAF

MDVGTEWRTLRRICKEQMFSTQSLETSQGLRQEKLQQLHDFVQRCCDSGRVVDIRE

ASFVTTLNLMSATLFSIQATEFDSNATEEFREIMEGVASIVGDPNFADYFPILKRFDPQ

GVKRKAELYFGKMLVLVEDLLQKRQEERRRSPSYAKKDDLLERLVDVLNEKNEYKLT

TKHITHLLLDLFVGGSETTTTSVEWIMSELLINPEKLAKLKEELKTVVGEKKQVQESDIP

QLPYFEAVLKEVFRLHPPGPLLLPRKAECDVQVGSYTIPKETQILVNAWAIGRDPAIWP

NPEAFEPERFLSQKMDYKGQDFELIPFGSRRICPGLSFANRMLPMTVATLIHNFDWK

LEVEANAEDVHKGEMFGIAVRRAVPLRAYPIQP

DNA sequence encoding CfCYP76AH8
SEQ ID NO: 5

ATGGAAACCATCACCTTGTTGTTGGCCTTGTTTTTCATTGCTTTGACCTACTTCATC

TCCTCCAGAAGAAGAAGAAATTTGCCACCAGGTCCATTTCCATTGCCAATTATTGG

TAACATGTTGCAATTGGGTTCCAAGCCACATCAATCTTTTGCTCAATTGTCCAAAAA

GTACGGTCCATTGATGTCCATTCATTTGGGTTCCTTGTACACCGTTATAGTCTCTT

CACCAGAAATGGCCAAAGAAATCTTGCAAAAACACGGTCAAGTTTTCTCCGGTAG

AACTATTGCTCAAGCTGTTCATGCTTGTGATCACGATAAGATTTCTATGGGTTTTTT

GCCAGTTGCCAACACTTGGAGAGATATGAGAAAGATCTGCAAAGAACAAATGTTC

TCCCACCATTCTTTGGAAGCTAGTGAAGAATTGAGACACCAAAAGTTGCAACAATT

-continued

```
ATTAGACTACGCTCAAAAGTGTTGCGAAGCTGGTAGAGCTGTTGATATTAGAGAA
GCCTCTTTCATTACCACCTTGAACTTGATGTCTGCTACTATGTTTTCTACCCAAGCT
ACCGAATTTGATTCCGAAGCTACAAAAGAATTCAAAGAAATTATCGAAGGTGTCGC
CACTATAGTTGGTGTTGCTAATTTTGCTGATTACTTCCCAATCTTGAAGCCATTTGA
CTTGCAAGGTATTAAGAGAAGAGCTGATGGTTACTTCGGTAGATTATTGAAGTTGA
TCGAAGGTTACTTGAACGAAAGATTGGAATCTAGAAGATTGAACCCAGATGCTCCA
AGAAAGAAGGATTTCTTGGAAACCTTGGTTGATATCATCGAAGCCAACGAATACAA
GTTGACTACTGAACATTTGACCCACTTGATGTTGGATTTGTTTGTTGGTGGTTCTG
AAACTAACACCACATCCTTGGAATGGATCATGTCTGAATTGGTTATCAACCCAGAT
AAGATGGCCAAGGTCAAAGAAGAATTGAAGTCTGTTGTTGGTGACGAAAAGTTGG
TTAACGAATCTGATATGCCAAGATTGCCATACTTGCAAGCCGTTATCAAAGAAGTT
TTGAGAATTCATCCACCTGGTCCTTTGTTGTTGCCAAGAAAAGCTGAATCTGATCA
AGTTGTTAACGGTTATTTGATCCCAAAGGGTACTCAAATTTTGTTCAATGCTTGGG
CTATGGGTAGAGATCCAACTATTTGGAAAGATCCAGAATCCTTCGAACCAGAAAGA
TTCTTGAATCAATCCATCGACTTCAAGGGTCAAGACTTCGAATTGATTCCATTTGG
TTCTGGTAGAAGAATCTGTCCAGGTATGCCATTGGCTAATAGAATCTTGCATATGA
CTACCGCCACTTTGGTTCATAATTTCGATTGGAAATTGGAAGAAGGTACTGCTGAC
GCTGATCATAAGGGTGAATTATTTGGTTTGGCTGTTAGAAGAGCTACCCCATTGAG
AATCATTCCATTGAAACCATAA
```

DNA encoding CYP76AH11
SEQ ID NO: 6

```
ATGGAATTGGTCCAAGTTATCGCTGTTGTTGCAGTTGTTGTTGTTTTGTGGTCCCA
ATTGAAAAGAAAGGGTAGAAAATTGCCACCAGGTCCATCTCCATTGCCAATAGTTG
GTAATATCTTCCAATTGTCCGGTAAGAACATCAACGAATCTTTCGCTAAGTTGTCC
AAAATCTACGGTCCAGTTATGTCTTTGAGATTGGGTTCTTTGTTGACCGTCATTATC
TCTTCACCAGAAATGGCCAAAGAAGTCTTGACTTCTAAGGATTTTGCTAACAGACC
ATTGACTGAAGCTGCTCATGCTCATGGTCATTCTAAATTTTCTGTTGGTTTCGTTCC
AGTCTCTGATCCAAAATGGAAACAAATGAGAAGAGTCTGCCAAGAAGAAATGTTC
GCCTCTAGAATTTTGGAAAACTCCCAACAAAGAAGACACCAAAAGTTGCAAGAATT
GATCGACCACGTTCAAGAATCTAGAGATGCTGGTAGAGCTGTTACTATTAGAGATC
CAGTTTTCGCTACCACCTTGAACATTATGTCCTTGACTTTGTTTTCTGCCGATGCTA
CTGAATTCTCTTCTTCTGCTACTGCTGAATTGAGAGATATTATGGCTGGTGTTGTTT
CTGTTTTGGGTGCTGCTAATTTGGCTGATTTCTTCCCAATCTTGAAATACTTCGATC
CACAAGGTATGAGAAGAAAGGCTGACTTGCATTACGGTAGATTGATTGACCATATC
AAGTCCAGAATGGACAAGAGATCTGAATTGAAGAAGGCTAATCCAAACCATCCAA
AGCACGATGATTTCTTGGAAAAGATCATCGACATCACCATTCAAAGAAACTACGAC
TTGACCATTAACGAAATCACCCATTTGTTGGTCGACTTGTATTTGGCTGGTTCTGA
ATCTACTGTTATGACCATTGAATGGACCATGGCCGAATTGATGTTAAGACCAGAAT
CATTGGCTAAATTGAAGGCAGAATTGAGATCCGTTATGGGTGAAAGAAAGATGAT
CCAAGAATCCGACGACATTTCTAGATTGCCATACTTAAACGGTGCTATCAAAGAAG
CCTTAAGATTGCATCCACCTGGTCCTTTGTTGTTTGCTAGAAAGTCTGAAATCGAT
```

```
GTTGAATTGTCTGGTTACTTCATCCCAAAGGGTACTCAAATCTTGGTTAATGAATG

GGGTATGGGTAGAGATCCTTCTGTTTGGCCTAATCCAGAATGTTTTCAACCAGAAA

GATTTTTGGATAAGAACATTGACTACAAGGGTCAAGACCCACAATTGATTCCATTT

GGTGCAGGTAGAAGAATTTGTCCAGGTATTCCAATTGCCCATAGAGTTGTTCATTC

AGTTGTTGCTGCTTTGGTTCATAACTTCGATTGGGAATTTGCTCCTGGTGGTTCTC

AATGTAACAACGAATTTTTCACTGGTGCTGCCTTGGTTAGAGAAGTTCCATTGAAG

TTGATTCCTTTGAACCCACCATCCATCTGA
```

SEQ ID NO:7 is the protein sequence of TPS2 from *Coleus forskohlii*, which is described in Pateraki et al., 2014, Plant Physiology, March 2014, Vol. 164, pp. 1222-1236. The sequence has the GenBank accession number KF444507.

SEQ ID NO:8 is the protein sequence of TPS3 from *Coleus forskohlii*, which is described in Pateraki et al., 2014, Plant Physiology, March 2014, Vol. 164, pp. 1222-1236. The sequence has the GenBank accession number KF444508.

SEQ ID NO:9 is the protein sequence of TPS4 from *Coleus forskohlii*, which is described in Pateraki et al., 2014, Plant Physiology, March 2014, Vol. 164, pp. 1222-1236. The sequence has the GenBank accession number KF444509.

```
AH17(aa):
                                                         SEQ ID NO: 10
MESMNALVVGLLLIALTILFSLRRRRNLAPGPYPFPIIGNMLQLGTKPHQSFAQLSKKY

GPLMSIHLGSLYTVIVSSPEMAKEILQKHGQVFSGRTIAQAVHACDHDKISMGFLPVSN

TWRDMRKICKEQMFSHHSLEGSQGLRQQKLLQLLDYAQKCCETGRAVDIREASFITT

LNLMSATMFSTQATEFESKSTQEFKEIIEGVATIVGVANFGDYFPILKPFDLQGIKRKAD

GYFGRLLKLIEGYLNERLESRKSNPNAPRKNDFLETWDILEANEYKLSVDHLTHLMLD

LFVGGSETNTTSLEWTMSELVNNPDKMAKLKQELKSVVGERKLVDESEMPRLPYLQA

VIKESLRIHPPGPLLLPRKAETDQEVNGYLIPKGTQILFNVWAMGRDPSIWKDPESFEP

ERFLNQNIDFKGQDFELIPFGSGRRICPGMPLANRILHMATATMVHNFDWKLEQGTDE

ADAKGELFGLAVRRAVPLRIIPLQP amino acid sequence of CYP76AH15:
                                                         SEQ ID NO: 11
METMTLLLPLFFIALTYFLSWRRRRNLPPGPFPLPIIGNLLQIGSKPHQSFAQLSKKYGP

LMSVQLGSVYTVIASSPEMAKEILQKHGQVFSGRTIAQAAQACGHDQISIGFLPVATT

WRDMRKICKEQMFSHHSLESSKELRHEKLQKLLDYAQKCCEAGRAVDIREAAFITTLN

LMSATLFSTQATEFDSEATKEFKEVIEGVAVIVGEPNFADYFPILKPFDLQGIKRRANSY

FGRLLKLMERYLNERLESRRLNPDAPKKNDFLETLVDIIQADEYKLTTDHVTHLMLDLF

VGGSETSATSLEWIMSELVSNPSKLAKVKAELKSVVGEKKVVSESEMARLPYLQAVIK

EVLRLHPPGPLLLPRKAGSDQVVNGYLIPKGTQLLFNVWAMGRDPSIWKNPESFEPE

RFLNQNIDYKGQDFELIPFGSGRRICPGMPLADRIMHMTTATLVHNFDWKLEDGAGD

ADHKGDDPFGLAIRRATPLRIIPLKP cDNA sequence encoding CfCYP76AH15
                                                         SEQ ID NO: 12
ATGGAAACCATGACTCTTCCTCCCTCTTTTCTTCATCGCTCTGACATATTTCCTC

TCCTGGAGGCGCCGGAGAAACCTTCCTCCGGGGCCTTTTCCTCTTCCAATCATCG

GAAACTTGCTGCAAATCGGCTCCAAACCCCACCAGTCATTCGCCCAACTCTCAAA

GAAATATGGCCTCTCATGTCCGTCCAACTCGGGAGTGTATACACCGTGATAGCC

TCCTCCCCGGAAATGGCGAAAGAGATACTGCAAAAACACGGCCAAGTGTTTTCCG

GGAGAACCATCGCACAGGCGGCGCAAGCGTGCGGCCACGACCAGATCTCCATC

GGGTTTCTGCCGGTGGCAACCACGTGGCGTGATATGCGTAAAATATGCAAAGAAC
```

-continued
AGATGTTCTCGCATCACAGCCTGGAATCCAGCAAGGAGCTGAGGCACGAGAAGC
TGCAGAAGCTGCTGGACTACGCCCAGAAATGCTGCGAAGCCGGCCGTGCCGTTG
ATATTCGTGAGGCCGCCTTCATTACAACGCTCAACCTCATGTCTGCCACGTTGTTC
TCGACTCAAGCTACTGAGTTCGACTCCGAAGCTACAAAAGAGTTTAAGGAGGTCA
TCGAGGGGTGGCCGTCATTGTGGGTGAGCCTAATTTCGCTGACTACTTCCCCAT
CTTGAAGCCTTTCGATCTTCAGGGGATCAAGCGTAGAGCTAATAGCTACTTTGGAA
GACTGCTCAAGTTAATGGAGAGATATCTGAATGAGAGGCTGGAATCAAGAAGGTT
GAACCCAGATGCCCCCAAGAAGAATGACTTTTTGGAAACCCTGGTGGATATCATC
CAGGCTGATGAATACAAGCTCACGACCGACCACGTCACGCACCTCATGCTTGACT
TATTTGTTGGAGGATCGGAAACAAGCGCGACCTCACTGGAATGGATAATGTCGGA
GTTAGTGAGCAATCCGAGTAAATTGGCGAAGGTGAAAGCGGAGCTCAAGAGCGTT
GTAGGAGAAAAGAAAGTGGTGAGCGAATCAGAAATGGCGAGGCTGCCATACTTG
CAAGCAGTGATCAAAGAAGTGCTCCGACTTCACCCTCCCGGCCCTCTTCTGCTTC
CTCGCAAGGCAGGGAGTGATCAAGTTGTGAATGGATACCTGATCCCAAAGGGAAC
TCAATTACTCTTCAATGTATGGGCAATGGGCAGAGACCCCAGTATCTGGAAGAAT
CCTGAATCTTTCGAGCCCGAGCGCTTCCTCAATCAAAACATAGACTACAAAGGCC
AAGATTTCGAGCTCATTCCATTCGGGTCCGGGAGAAGAATTTGCCCCGGTATGCC
GCTGGCGGATCGGATTATGCACATGACGACGGCCACTCTGGTTCACAACTTCGAT
TGGAAACTGGAAGACGGAGCAGGTGATGCGGATCACAAGGGAGACGACCCCTTC
GGCTTGGCCATCCGCCGTGCAACTCCTCTCAGGATCATTCCACTTAAGCCATGA cDNA encoding CfCYP76AH17:

SEQ ID NO: 13

ATGGAAAGCATGAATGCTCTTGTCGTCGGTCTCTTGTTGATCGCTTTGACAATTTT
GTTTTCGTTGAGGCGGCGGAGAAACCTTGCTCCGGGGCCTTATCCTTTTCCGATC
ATCGGAAACATGCTTCAACTGGGCACGAAACCACACCAATCATTCGCCCAGCTGT
CGAAGAAATATGGGCCGCTCATGTCCATCCACCTGGGAAGTTTATACACAGTGAT
CGTTTCGTCGCCGGAAATGGCGAAAGAGATCCTGCAAAAGCACGGCCAAGTGTTT
TCAGGGAGAACCATCGCTCAGGCGGTGCATGCATGCGACCACGACAAGATCTCC
ATGGGGTTTCTGCCGGTGTCGAACACGTGGCGCGATATGCGTAAAATATGCAAAG
AGCAGATGTTCTCGCATCACAGCTTGGAAGGCAGCCAGGGTCTCCGCCAGCAGA
AGCTGCTGCAGCTGCTCGACTACGCCCAGAAGTGCTGCGAAACCGGCCGCGCCG
TTGACATTCGTGAGGCTTCCTTCATCACAACTCTCAACCTCATGTCGGCCACCATG
TTTTCGACTCAAGCTACCGAGTTTGAATCGAAATCTACTCAGGAGTTCAAGGAGAT
CATTGAAGGCGTGGCCACGATTGTGGGCGTGGCTAATTTCGGAGACTACTTCCCA
ATCTTGAAGCCTTTCGATCTGCAGGGGATCAAGAGAAAAGCTGATGGCTACTTCG
GCAGATTGCTGAAATTAATCGAGGGCTATCTCAATGAAAGATTGGAATCCAGAAAA
TCGAACCCAAATGCCCCCAGAAAGAATGACTTTTTGGAAACAGTGGTCGATATCCT
CGAGGCAAATGAGTACAAGTTGTCAGTCGACCACCTCACGCATCTCATGCTGGAT
TTGTTTGTTGGAGGATCGGAAACAAACACGACCTCACTGGAGTGGACAATGTCGG
AGTTAGTGAACAACCCCGACAAAATGGCCAAGCTGAAACAGGAGCTGAAGAGCGT
TGTAGGAGAGAGGGAAACTGGTGGATGAGTCGGAGATGCCGAGGCTGCCATATCT
GCAAGCTGTCATCAAAGAATCGCTCCGAATTCACCCACCGGGCCCTCTTCTTCTC

-continued

```
CCTCGCAAAGCAGAGACCGATCAAGAGGTGAATGGATATCTCATCCCAAAAGGGA

CTCAGATTCTCTTCAATGTGTGGGCAATGGGCAGGGATCCTAGCATCTGGAAGGA

TCCTGAATCTTTTGAGCCCGAGCGCTTCCTCAATCAAAACATAGACTTCAAAGGCC

AAGATTTCGAGCTCATTCCATTCGGGTCGGGCCGAAGAATCTGCCCCGGCATGCC

GCTGGCCAATCGGATTCTCCACATGGCCACCGCGACTATGGTTCATAACTTCGAT

TGGAAACTGGAACAAGGAACAGATGAAGCTGATGCCAAAGGAGAGTTGTTTGGAT

TGGCCGTGCGCAGGGCAGTTCCCCTCAGGATCATTCCACTTCAGCCTTAA
```

| | |
|---|---|
| SEQ ID NO:1 | Amino acid sequence of CYP76AH8 from *Coleus forskohlii* |
| SEQ ID NO:2 | Amino acid sequence of CYP76AH11 from *Coleus forskohlii* |
| SEQ ID NO:3 | Amino acid sequence of CYP71D381 from *Coleus forskohlii*- |
| SEQ ID NO:4 | Amino acid sequence of CYP76AH9 from *Coleus forskohlii* CYP76AH9 may also be referred to as CYP76AH2. |
| SEQ ID NO:5 | DNA sequence encoding CYP76AH8 from *Coleus forskohlii*. DNA sequence codon optimised for expression in yeast |
| SEQ ID NO:6 | DNA sequence encoding CYP76AH11 from *Coleus forskohlii*. DNA sequence codon optimised for expression in yeast |
| SEQ ID NO:7 | Amino acid sequence of TPS2 from *Coleus forskohlii*- |
| SEQ ID NO:8 | Amino acid sequence of TPS3 from *Coleus forskohlii* |
| SEQ ID NO:9 | Amino acid sequence of TPS4 from *Coleus forskohlii*. |
| SEQ ID NO:10 | Amino acid sequence of CYP76AH17 from *Coleus forskohlii* |
| SEQ ID NO:11 | Amino acid sequence of CYP76AH15 from *Coleus forskohlii* |
| SEQ ID NO:12 | cDNA sequence encoding CYP76AH15 from *Coleus forskohlii* |
| SEQ ID NO:13 | cDNA sequence encoding CYP76AH17 from *Coleus forskohlii* |

EXAMPLES

The invention is further illustrated by the following examples, which however are not intended as being limiting for the invention.

Example 1

Figure 1B:
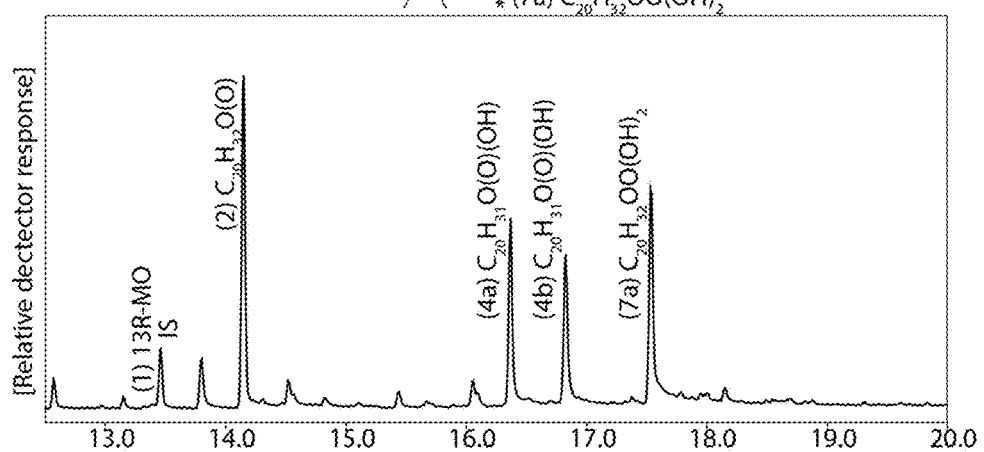
FIG. 1B shows GC-MS analysis of extracts from assays with *Nicotiana benthamiana* plants producing (1) 13R-MO and expressing CYP76AH8 of SEQ ID NO:1. GC-MS trace with relative detector response and retention time in minutes. (1) 13R-MO [only traces detected] (2) keto-13R-MO (8,13-epoxy-labd-14-ene-11-one), (4a) keto-hydroxy-13R-MO and (4b) keto-hydroxy-13R-MO and (5) keto-dihydroxy-13R-MO are detected. IS, internal standard are shown.

The entire pathway to the high-value drug forskolin is active in a single cell type in the root of *Coleus forskohlii*. To identify the genes encoding the enzymes involved in decorating 13R-manoyl oxide (13R-MO) through oxidative functionalization of the backbone, a transcriptome prepared from aforementioned cell type was used. Candidates of the large family of cytochrome P450 enzymes (P450) were identified and build into an exhaustive inventory of cloned full-length sequences (Cf450s). CfP450s were tested in a transient *Agrobacterium/Nicotiana benthamiana* heterologous expression system, which produced 13R-MO. In particular, some *Nicotiana benthamiana* plants expressed TPS2 of SEQ ID NO:7 and TPS3 of SEQ ID NO:8 and thus were able to produce 13R-MO in addition to one or more CfP450s to be tested. All CfP450s were tested and in gas-chromatography mass-spectrometry analyses of extracts from plants expressing CfCYP76AH9 (SEQ ID NO:4), CYP71D381 of SEQ ID NO:3 and/or CYP76AH8 of SEQ ID NO:1, conversion of 13R-MO was observed, next to accumulation of novel, oxidised products. Specifically with CYP76AH8, conversion of the substrate to keto-dihydroxy 13R-MO was detected, while one ketonated and two further hydroxylated products were found, consistent with the most simple 13R-MO ketone intermediate also detected in the native *C. forskohlii*. This keto-group is also found in all forskolin derivatives detected in the plant extract, indicating that this represents the first biosynthetic intermediate and the first required step towards forskolin. GC-MS analysis of extracts from assays with *Nicotiana benthamiana* plants producing 13R-MO and expressing CYP76AH8 shows production of (2) keto-13R-MO by *Coleus forskohlii* CYP76AH8, as well as production of (4a) keto-hydroxy-13R-MO and (4b) keto-hydroxy-13R-MO and (7a) keto-dihydroxy-13R-MO (see FIG. 1). The identity of the compounds was confirmed by mass spectrometry. Only traces of 13R-MO are detected. A potential intermediate, hydroxyl-13R-MO, IS, internal standard and minor hydroxylation side products are also detected (see FIG. 1).

Figure 11A:
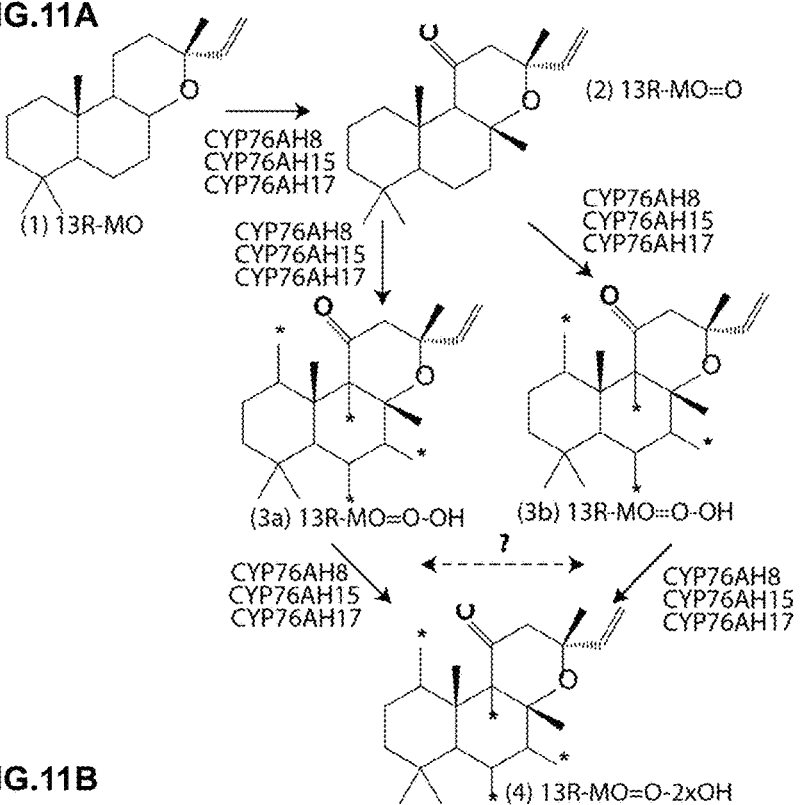
FIG. 11A shows a scheme of the full oxidation of (1) 13R-MO to (2) keto-13R-MO (8,13-epoxy-labd-14-ene-11-one), (3a) keto-hydroxy-13R-MO and (3b) keto-hydroxy-13R-MO and (4) keto-dihydroxy-13R-MO by *Coleus forskohlii* CYP76AH8, CYP76AH15 or CYP76AH17. * indicates possible position of —OH group(s).
Figure 11B:
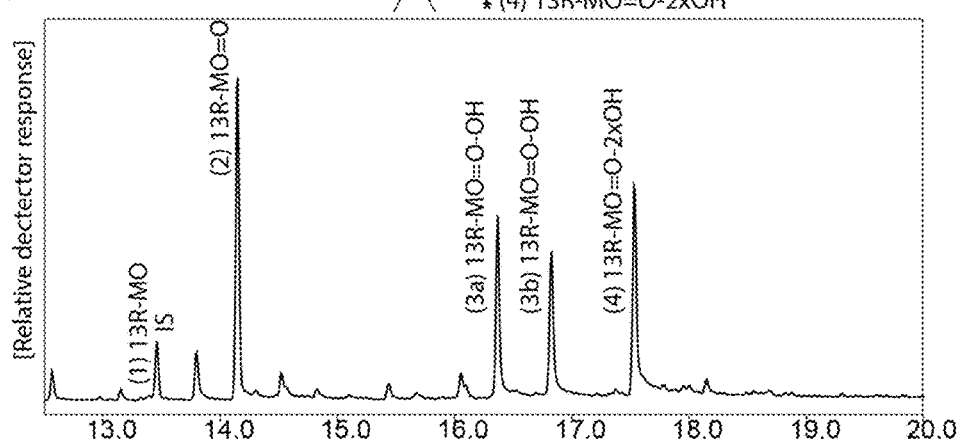
FIG. 11B shows GC-MS analysis of extracts from assays with *Nicotiana benthamiana* plants producing (1) 13R-MO and expressing CYP76AH8 of SEQ ID NO:1. GC-MS trace with relative detector response and retention time in minutes. (1) 13R-MO [only traces detected] (2) keto-13R-MO (8,13-epoxy-labd-14-ene-11-one), (3a) keto-hydroxy-13R-MO and (3b) keto-hydroxy-13R-MO and (5) keto-dihydroxy-13R-MO are detected. IS, internal standard are shown.

A similar result was observed in *Nicotiana benthamiana* plants expressing either CYP76AH15 of SEQ ID NO:11 or CYP76AH17 of SEQ ID NO:10 together with TPS2 of SEQ ID NO:7 and TPS3 of SEQ ID NO:8. Thus, such plants also produced (2) keto-13R-MO, (3a) keto-hydroxy-13R-MO and (3b) keto-hydroxy-13R-MO and (4) keto-dihydroxy-13R-MO as determined by GC-MS (see FIG. 11). Thus, it appears that CfCYP76AH8, CfCYP76AH15 and CfCYP76AH17 have similar activity.

Figure 2A:
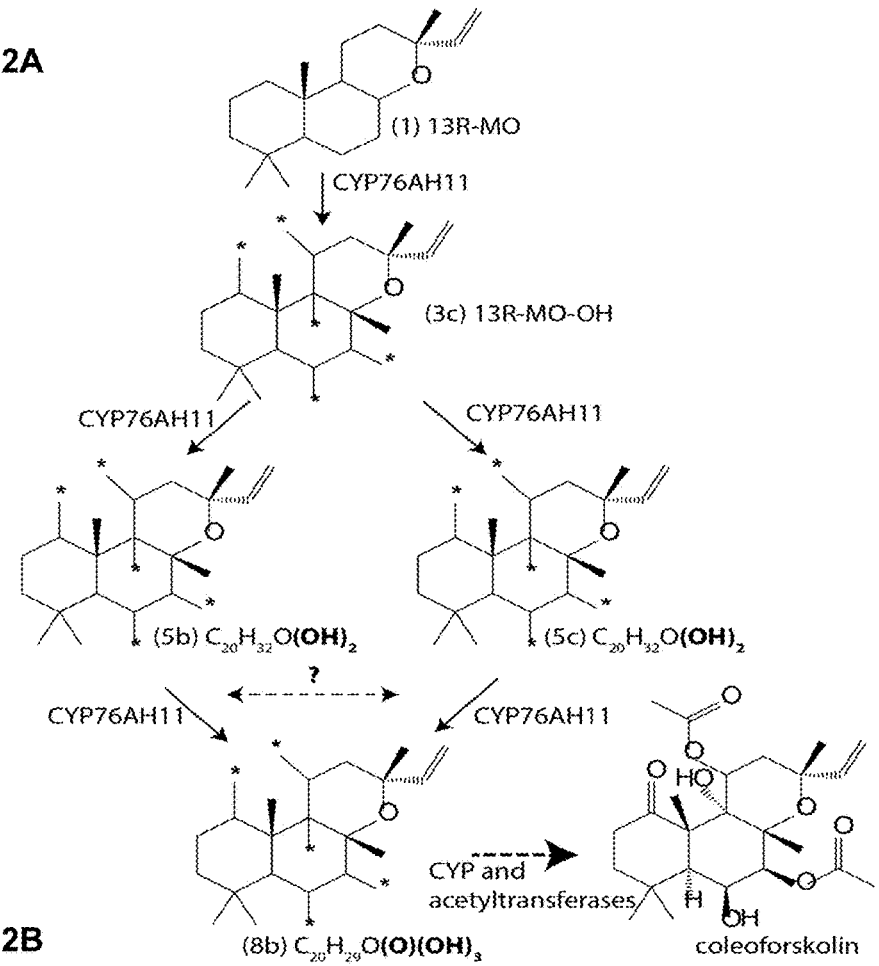
FIG. 2A shows a scheme of the full oxidation of (1) 13R-MO to (3c) hydroxy-13R-MO, (5b) dihydroxy-13R-MO and (5c) dihydroxy-13R-MO and (8b) trihydroxy-13R-MO by *Coleus forskohlii* CYP76AH11. * indicates possible position of —OH group(s).
Figure 2B:
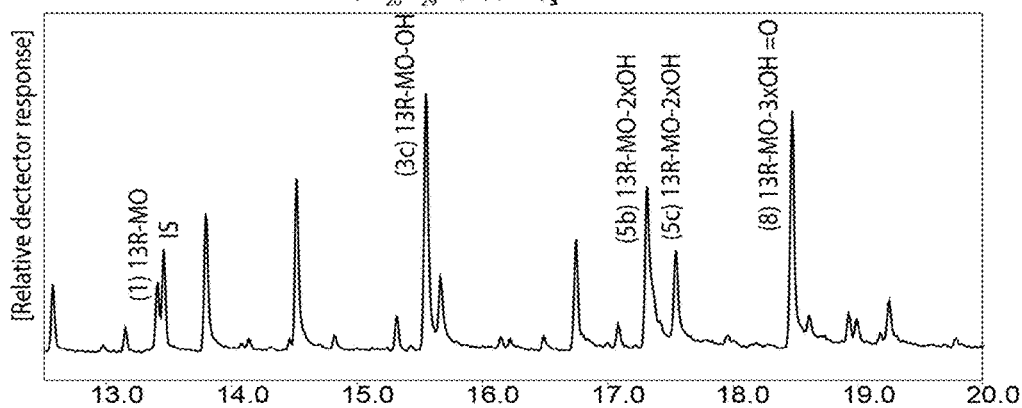
FIG. 2B shows GC-MS analysis of extracts from assays with *Nicotiana benthamiana* plants producing 13R-MO and expressing CYP76AH11 of SEQ ID NO:2. 1) 13R-MO to (3c) hydroxy-13R-MO, (5b) dihydroxy-13R-MO and (5c) dihydroxy-13R-MO and (8b) trihydroxy-13R-MO are detected. A GC-MS trace with relative detector response and retention time in minutes. * indicates possible position of —OH group(s).

A *N. benthamiana* system producing 13R-MO and expressing CYP76AH11 of SEQ ID NO:2 was also generated. With this efficient and specific oxidation of the 13R-MO into further hydroxylated derivative was achieved. Similar to CYP76AH8, this conversion is near quantitative. The GC-MS analysis showed production of 3c) hydroxy-13R-MO, (5b) dihydroxy-13R-MO and (5c) dihydroxy-13R-MO and (8b) trihydroxy-13R-MO (see FIG. 2). The identity of the compounds was confirmed by mass spectrometry.

A *N. benthamiana* system producing 13R-MO and expressing both CYP76AH8 of SEQ ID NO:1 and CYP76AH11 of SEQ ID NO:2 was also generated. With this efficient and specific oxidation of the 13R-MO ketone intermediate into a single further hydroxylated derivative was achieved. The characteristic mass and the retention time support four different positions with a novel hydroxyl group and the required keto-group in correct regiospecificity. GC-MS analysis of extracts from assays with *Nicotiana benthamiana* plants producing 13R-MO and expressing CYP76AH8 of SEQ ID NO:1 and CYP76AH11 of SEQ ID NO:2 indicates oxidation of (1) 13R-MO via (2) keto-13R-MO to (4d) hydroxyl-keto-13R-MO, (7a) keto-dihydroxy-13R-MO and (8a) keto-trihydroxy-13R-MO by the pair of

*Coleus forskohlii* CYP76AH8 and CYP76AH11 (see FIG. 3). (6a) hydroxyl-di-keto-13R-MO is also produced. The identity of the compounds was confirmed by mass spectrometry.

The specific identity of the compounds (2), (5c), (7a) and (8A) was further determined by NMR as described below in Example 2.

Compound (2) was identified as 8,13-epoxy-labd-14-ene-11-one.

Compound (5c) was identified as 7-11-dihydroxy-13R-manoyl oxide

Compound (7a) was identified as 1-9-deoxydeacethylforskolin

Compound (8a) was identified as 1-deoxydeacethylforskolin

Figure 4A:
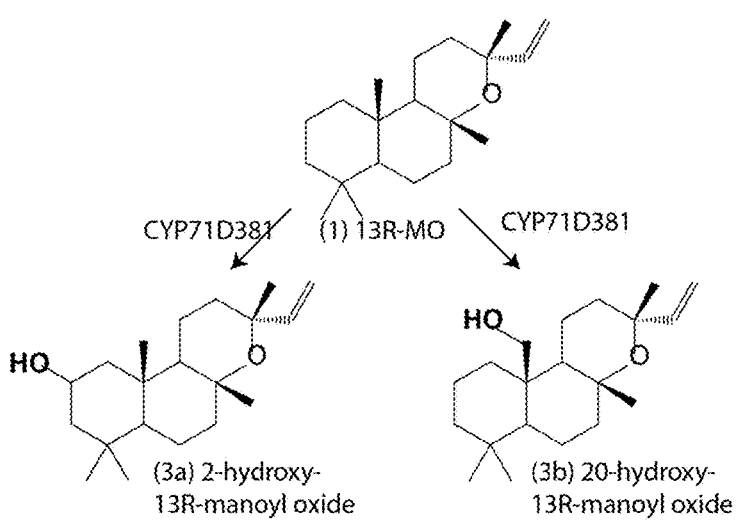
FIG. 4A shows selected observed oxidation reactions of 13R-MO. CYP71D381 effectively catalyse two hydroxylation reactions going from compound (1) to either (3a) 2-hydroxy-13R-manoyl oxide or (3b) 20-hydroxy-13R-manoyl oxide.
Figure 4B:
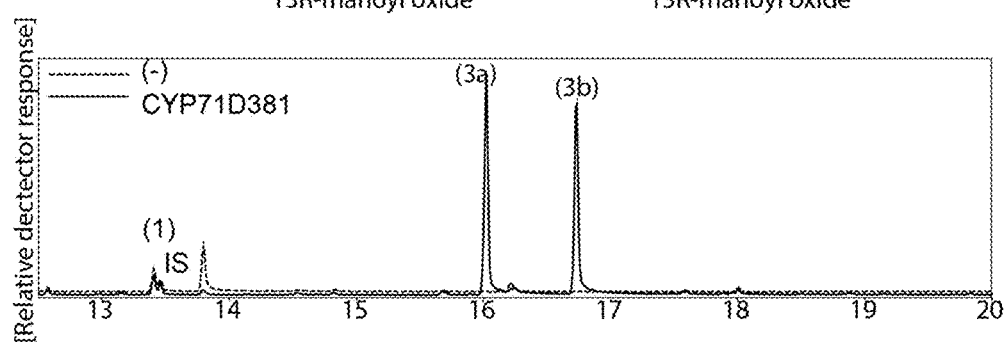
FIG. 4B shows GC-MS analysis of extracts from assays with *Nicotiana benthamiana* plants producing 13R-MO and expressing CYP71D381. (1) 13R-MO, (3a) 2-hydroxy-13R-MO and (3b)20-hydroxy-13R-MO are detected. A GC-MS trace with relative detector response and retention time in minutes.

A *N. benthamiana* system producing 13R-MO and expressing CYP71D3811 of SEQ ID NO:3 was also generated. GC-MS analysis of extracts from said *Nicotiana benthamiana* plant indicates production of (1) 13R-MO, (3a) hydroxy-13R-MO and (3b) hydroxy-13R-MO (see FIG. 4). The identity of the compounds was confirmed by mass spectrometry. The identity of the compounds as (3a) 2-hydroxy-13R-manoyl oxide and (3b) 20-hydroxy-13R-manoyl oxide was further determined by NMR as described in Example 2 below.

Figure 5A:
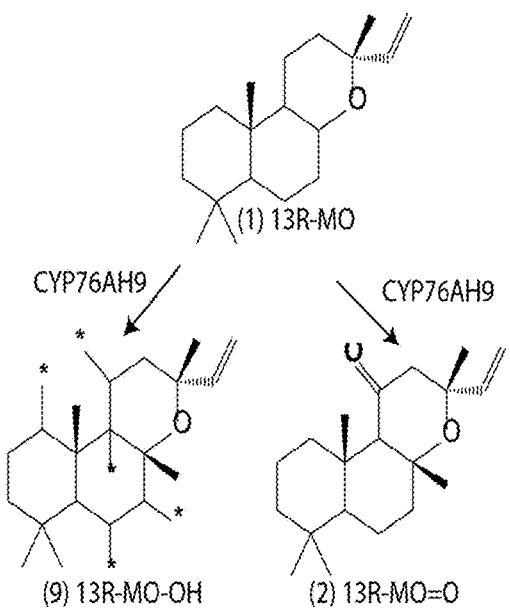
FIG. 5A shows selected observed oxidation reactions of 13R-MO. CYP76AH9 catalyse two hydroxylation reactions going from compound (1) to either (2) keto-13R-MO (8,13-epoxy-labd-14-ene-11-one) or (9) hydroxy-13R-MO. * indicates possible position of —OH group(s).
Figure 5B:
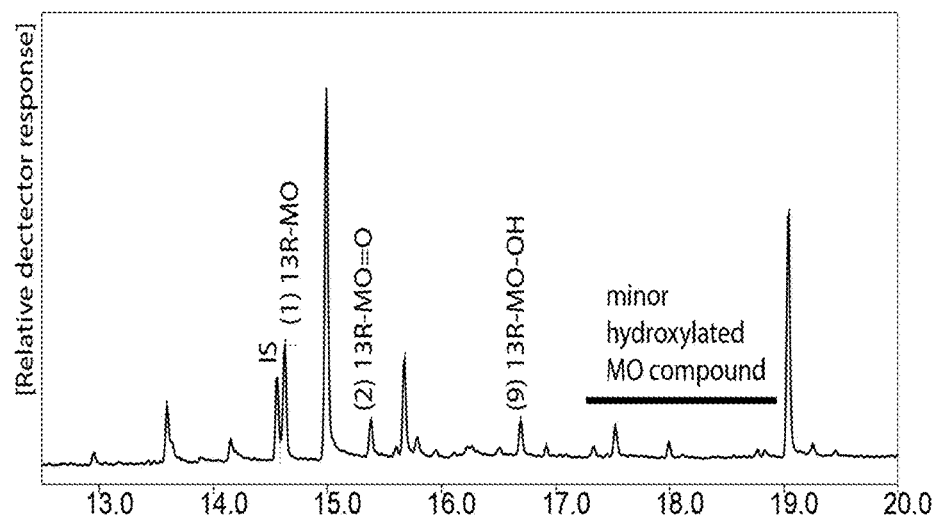
FIG. 5B shows GC-MS analysis of extracts from assays with *Nicotiana benthamiana* plants producing 13R-MO and expressing CYP76AH9. (1) 13R-MO, (2) keto-13R-MO (8,13-epoxy-labd-14-ene-11-one) and (9) hydroxy-13R-MO are detected. A GC-MS trace with relative detector response and retention time in minutes

A *N. benthamiana* system producing 13R-MO and expressing CYP76AH9 of SEQ ID NO:4 was also generated. GC-MS analysis of extracts from said *Nicotiana benthamiana* plant indicates production of (1) 13R-MO, (2) keto-13R-MO and (9) hydroxy-13R-MO (see FIG. 5). The identity of the compounds was confirmed by mass spectrometry.

Figure 9:
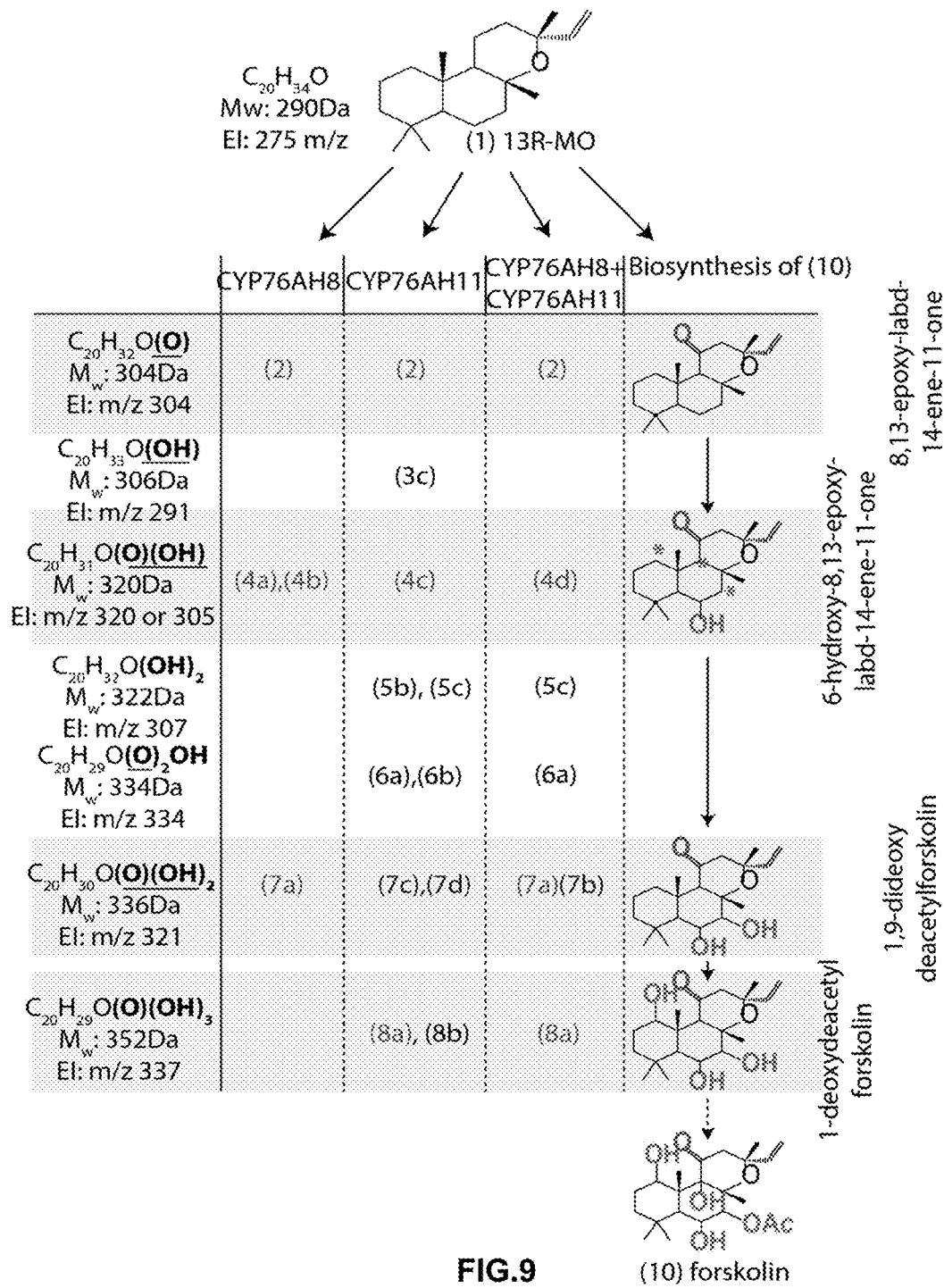
FIG. 9 shows an overview of the biosynthesis of forskolin. Each column shows the compounds produced by CYP76AH8, CYP76AH11 and by the combined action of CYP76AH8 and CYP76AH11. The right hand column shows the structure of the compounds as well as one route to forskolin. The numbers in the table refers to the compound numbers used in FIGS. 1 to 3. The chemical names and structures of the compounds are provided in FIGS. 1 to 3. More specifically, (2) is (8,13-epoxy-labd-14-ene-11-one), (5c) is 7-11-dihydroxy-13R-manoyl oxide, (7a) is 1-9-deoxydeacethylforskolin and (8a) is 1-deoxydeacethylforskolin.

Forskolin is complex functionalised derivative of 13R-MO requiring region- and stereospecific oxidation of five carbon positions: one double-oxidation leading to a ketone and four single oxidation reactions yielding hydroxyl groups. The results presented herein shows identification of cytochrome P450 mono-oxygenases, which efficiently catalyse independent regiospecific hydroxylations (CYP71D381), one hydroxylation and formation of the ketone (CYP76AH8), and the subsequent regiospecific oxidation of the ketone to a hydroxyl-ketone (CYP76AH8/CYP76AH11). FIG. 9 shows one biosynthetic pathway to forskolin involving use of CYP76AH8 and CYP76AH11. In addition a fourth P450 was found to catalyse specific hydroxylations on the 13R-MO backbone (CYP76AH9) at an efficiency indicating that the enzyme might be more active in catalysing hydroxylation of partly oxidised 13R-MO. This establishes the correct sequence of several the reactions from 13R-MO to forskolin with the respective P450s and also further hydroxylation reactions with an order in the route to be determined.

A summary of the observed oxidation reactions of 13R-MO en route to forskolin are shown in FIG. 7. CYP76AH8 and CYP76AH11 effectively catalyse the first three reactions, CYP71D381 and CYP76AH9 catalyse hydroxylation reactions.

Example 2

Biosynthesis and Isolation of MO Derivatives for Structural Determination by NMR NMR structural characterization of CfCYP product was achieved by extraction from up to 40 *N. benthamiana* plants. The *N. benthamiana* were modified so that it produced 13R-MO and furthermore cDNAs encoding the relevant CfCYP(s) catalyzing oxygenations on the MO backbone were introduced. The relevant CYPs and combinations thereof are described above in Example 1. For example, in one experiment cDNAs encoding CYP76AH8 of SEQ ID NO:1 and CYP76AH11 of SEQ ID NO:2 were introduced and in another experiment cDNA encoding CYP71D3811 of SEQ ID NO:3 was introduced. For infiltration, 0.5 L of agrobacteria cultures for each individual biosynthetic gene was grown overnight using 10 mL starter cultures. The agrobacteria were harvested by centrifugation at 4000×g for 20 min and resuspended in 100 mL water. The $OD_{600}$ of the independent samples were normalized and adjusted to a final concentration of $OD_{600}$ of 0.5 before combining for vacuum infiltration of whole *N. benthamiana* plants at −80 mmHg for 30 seconds. Post infiltration growth and extraction was performed similar to small scale extraction using 500 mL n-hexane as extraction solvent. After removal of the solvent by rotor evaporation (Buchi, Schwitzerland) set to 35° C. and 220 mbar, the residue was subjected twice to solid phase extraction on a Dual Layer Florisil/$Na_2SO_4$ 6 mL PP SPE TUBE (Superleco Analytical), eluting the compounds with 1% ethyl-acetate in n-hexane for removal of fatty acids and other polar components co-extracted with the oxygenated MO. The samples were concentrated by evaporation of the solvent under a stream of nitrogen before chromatography. Final purification was performed using a preparative gas chromatography coupled to a mass spectrometer (7890B GC, 5977A MSD, Agilent technologies) in line with a preparative fraction collector (PFG, Gerstel Inc.) using a preparative scale HP5 column (30 m×250 μm×0.25 μm, Restek Corporation), running with a linear flow of 45 cm/sec using hydrogen as carrier gas and a 1:99 split between the detector and the fraction collection. The oven program was set to 60° C. for 1 min, ramp with 20° C./min to 320° C. which was held for 3 min. The ion source and quadropole temperature were set to 230° C. and 150° C., respectively. Scan mode from m/z 35 to m/z 500 was used for detection. Peaks of interest were identified by their characteristic mass fragmentation pattern and selected for collection of the compounds in 1 μL sample traps (Gerstel) at room temperature, while the temperature for the PFC transfer line and PFC switching device was set to 280° C. Quantities suitable for NMR structural identification were typically collected from 100 injections with a volume of 5 μL. Purified compounds were directly recovered from the traps with deuterated chloroform ($CDCl_2$), concentrated in an argon stream before transferring into 1.7 mm NMR tubes.

NMR Analysis for Structural Identification of Hydroxylated MO Derivatives

NMR-spectra were acquired using a 600 MHz Bruker Avance III HD equipped with a cryogenically cooled 1.7-mm cryogenically cooled $_1H/_{13}C/_{15}N$ TCI probe head (Bruker). Samples dissolved in $CDCl_2$ (Sigma-Aldrich, 99.8 atom % D) were analyzed at 300 K. Proton spectra, at 600.03 MHz, were acquired using 30°-pulses, a spectral width of 12 kHz, collecting 16 scans with a length of 65536 data points with a relaxation delay of 1.0 sec. FID's were zero-filled to twice the size and exponentially multiplied with a line broadening factor of 0.3 Hz before Fourier transform. HSQC, COSY, HMBC and NOESY spectra were acquired in a similar manner.

The NMR analysis confirmed the specific identity of compounds:
(2) 8,13-epoxy-labd-14-ene-11-one
(3a) 2-hydroxy-13R-manoyl oxide
(3b) 19-hydroxy-13R-manoyl oxide (5c) 7-11-dihydroxy-13R-manoyl oxide
(7a) 1-9-deoxydeacethylforskolin
(8a) 1-deoxydeacethylforskolin The 13c NMR spectrometric reference for compound 2 is provided below:

| # C | Compound (2) | Gabetta et al. 1989 |
|---|---|---|
| 20 | 15.63 | 15.5 |
| 2 | 18.49 | 18.4 |
| 6 | 19.80 | 19.7 |
| 19 | 21.76 | 21.6 |
| 18 | 28.10 | 27.9 |
| 17 | 31.41 | 31.2 |
| 4 | 33.40 | 33.2 |
| 16 | 33.65 | 33.5 |
| 10 | 37.29 | 37.1 |
| 7 | 39.59 | 39.4 |
| 1 | 42.05 | 41.9 |
| 3 | 43.42 | 43.3 |
| 12 | 50.38 | 50.2 |
| 5 | 55.97 | 55.8 |
| 9 | 66.90 | 66.7 |
| 13 | 75.11 | 74.4 |
| 8 | 77.49 | 77.2 |
| 15 | 112.30 | 111.9 |
| 14 | 146.87 | 146 |
| 11 | 207.74 | 207.1 |

Gabetta et al., 1989, PhytochemistryV, o I. 28, No. 3, pp. 859-86.

Example 3 Biosynthesis of Oxidized Manoyl Oxide Derivatives Using CYP76AH8 and CYP76AH11

*C. forskohlii* cDNAs/genes were introduced into yeast cells (*S. cerevisiae*) using standard yeast transformation methods followed by genomic integration.

Heterologous genes were controlled by endogenous constitutively active regulatory elements (promoters).

DNA sequences codon optimized for expression in *S. cerevisiae* encoding either CYP76AH8 (SEQ ID NO:5) or CYP76AH11 (SEQ ID NO:6) were introduced to yeast cells engineered to produce 13R-MO.

Selection of transformed yeast cells was performed through the selection marker introduced with the transgenes and by genotyping (using FOR techniques).

The selected yeast strains expressing the *C. forskohlii* genes were cultivated in Synthetic Complete URA dropout medium (SC-URA), at 28° C. for 72 hours.

Extraction of diterpenoids from the yeast culture was performed with ethanol: one volume of yeast culture (cells together with medium) was mixed with one volume of ethanol and heated at 80° C. for 15 min. Diterpenoids products from CYP76AH8 and CYP76AH11 were extracted from the ethanol-yeast culture mixture by one volume of hexane. Diterpenoids metabolites were analyzed by GC-MS.

Settings for GC-MS:

The oven program was set to 120° C. for 2 min, ramp with 30° C./min to 180° C., ramp with 10° C./min to 300° C., ramp with 30° C./min to 320° C., which was held for 2 min. The ion source and quadropole temperature were set to 300° C. and 150° C., respectively. MS detection was set in scan mode from m/z 50 to m/z 400 was used for detection.

Figure 10:
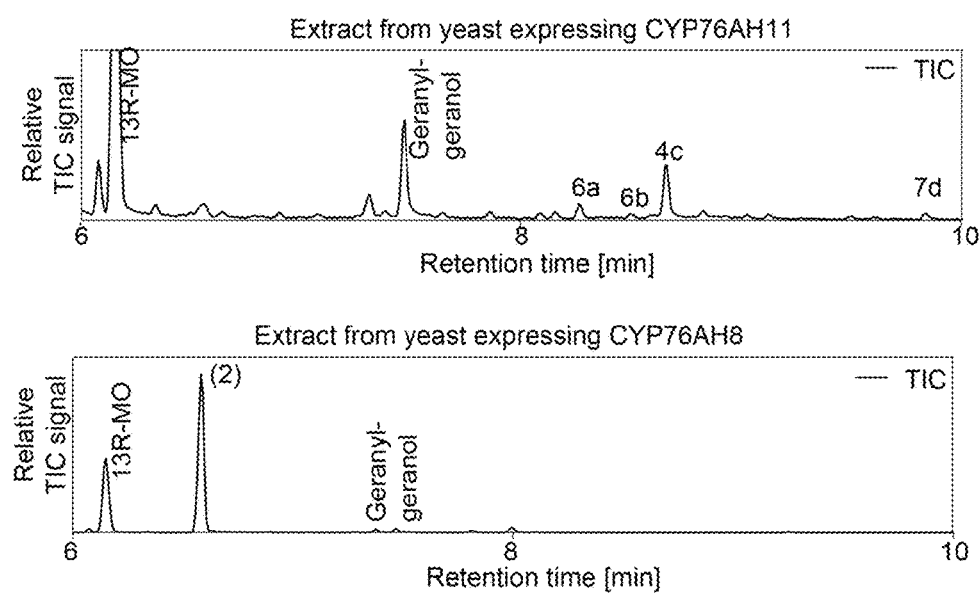
FIG. 10 shows GC-MS analysis of extracts from assays with *S. cerevisiae* producing 13R-MO and expressing either CYP76AH11 (upper panel) or CYP76AH8 (lower panel). In the upper panel compounds 6a, 6b and 4c are detected and in the lower panel compound 8 is detected. Chemical formula of the compounds are provided in FIG. 9.

The results of the GC-MS analysis are shown in FIG. 10. As apparent from FIG. 10, then yeast cells capable of producing 13R-MO and further expressing CYP76AH11 are capable of producing compounds 4c, 6a and 6b. The structure and chemical formula of compound 4c and the chemical formula of compounds 6a and 6b are shown in FIG. 9. Yeast cells capable of producing 13R-MO and further expressing CYP76AH8 are capable of producing compound 8. The structure and chemical formula of compound 8 are shown in FIG. 9.

The invention claimed is:

1. A host organism, comprising a heterologous nucleic acid encoding an enzyme capable of catalysing hydroxylation of 13R-manoyl oxide (13R-MO) and/or an oxidised 13R-MO derivative at the 11-position, wherein the oxidised 13R-MO carries a —H at the 11-position; and/or catalysing oxidation of a hydroxyl group to form an oxo-group at the 11-position of 11-hydroxyl-13R-MO and/or an oxidised 11-hydroxyl-13R-MO, wherein the enzyme comprises:
  (a) CYP76AH8 having at least 90% identity to the amino acid sequence set forth in SEQ ID NO:1;
  (b) CYP76AH17 having at least 90% identity to the amino acid sequence set forth in SEQ ID NO:10;
  (c) CYP76AH15 having at least 90% identity to the amino acid sequence set forth in SEQ ID NO:11; and/or
  (d) CYP76AH11 having at least 90% identity to the amino acid sequence set forth in SEQ ID NO:2.

2. The host organism of claim 1, further comprising:
  (a) a heterologous nucleic acid encoding an enzyme capable of catalysing hydroxylation of 13R-MO and/or oxidised 13R-MO at the 1-position, wherein the oxidised 13R-MO carries a —H at the 1-position;
  (b) a heterologous nucleic acid encoding an enzyme capable of catalysing hydroxylation of 13R-MO and/or oxidised 13R-MO at the 6-position, wherein the oxidised 13R-MO carries a —H at the 6-position;
  (c) a heterologous nucleic acid encoding an enzyme capable of catalysing hydroxylation of 13R-MO and/or oxidised 13R-MO at the 7-position, wherein the oxidised 13R-MO carries a —H at the 7-position; or
  (d) a heterologous nucleic acid encoding an enzyme capable of catalysing hydroxylation of 13R-MO and/or oxidised 13R-MO at the 9-position, wherein the oxidised 13R-MO carries a —H at the 9-position.

3. The host organism of claim 2, further comprising at least one heterologous nucleic acid encoding a polypeptide capable of catalysing hydroxylation of 11-keto-13R-manoyl oxide (13R-MO) and/or an oxidised 11-keto-13R-MO derivative at one or more of the positions 1, 6, 7 and/or 9, wherein the polypeptide is CYP76AH11 having at least 95% identity to the amino acid sequence set forth in SEQ ID NO:2.

4. The host organism of claim 2, further comprising at least one heterologous nucleic acid encoding a polypeptide capable of catalysing hydroxylation of 13R-manoyl oxide (13R-MO) and/or an oxidised 13R-MO at one or more of the positions 1, 6, 7 and/or 9, wherein the polypeptide is CYP71D381 having at least 95% identity to the amino acid sequence set forth in SEQ ID NO:3 or CYP76AH9 having at least 95% identity to the amino acid sequence set forth in SEQ ID NO:4.

5. The host organism of claim 1, wherein the host organism is a microorganism.

6. The host organism of claim 1, wherein the microorganism is yeast.

7. The host organism of claim 1, wherein the host organism is a plant.

8. The host organism of claim 1, wherein the host organism further comprises a heterologous nucleic acid encoding TPS2 having at least 95% identity to the amino acid sequence set forth in SEQ ID NO:7.

9. The host organism of claim 1, wherein the host organism further comprises a heterologous nucleic acid encoding TPS3 having at least 95% identity to the amino acid sequence set forth in SEQ ID NO:8 or TPS4 having at least 95% identity to the amino acid sequence set forth in SEQ ID NO:9.

* * * * *

SEQUENCE LISTING

```
<160> NUMBER OF SEQ ID NOS: 13

<210> SEQ ID NO 1
<211> LENGTH: 492
<212> TYPE: PRT
<213> ORGANISM: Coleus forskohlii

<400> SEQUENCE: 1

Met Glu Thr Ile Thr Leu Leu Leu Ala Leu Phe Phe Ile Ala Leu Thr
1               5                   10                  15

Tyr Phe Ile Ser Ser Arg Arg Arg Asn Leu Pro Pro Gly Pro Phe
            20                  25                  30

Pro Leu Pro Ile Ile Gly Asn Met Leu Gln Leu Gly Ser Lys Pro His
        35                  40                  45

Gln Ser Phe Ala Gln Leu Ser Lys Lys Tyr Gly Pro Leu Met Ser Ile
    50                  55                  60

His Leu Gly Ser Leu Tyr Thr Val Ile Val Ser Ser Pro Glu Met Ala
65                  70                  75                  80

Lys Glu Ile Leu Gln Lys His Gly Gln Val Phe Ser Gly Arg Thr Ile
                85                  90                  95

Ala Gln Ala Val His Ala Cys Asp His Asp Lys Ile Ser Met Gly Phe
            100                 105                 110

Leu Pro Val Ala Asn Thr Trp Arg Asp Met Arg Lys Ile Cys Lys Glu
        115                 120                 125
```

```
Gln Met Phe Ser His His Ser Leu Glu Ala Ser Glu Glu Leu Arg His
    130                 135                 140

Gln Lys Leu Gln Gln Leu Leu Asp Tyr Ala Gln Lys Cys Cys Glu Ala
145                 150                 155                 160

Gly Arg Ala Val Asp Ile Arg Glu Ala Ser Phe Ile Thr Thr Leu Asn
                165                 170                 175

Leu Met Ser Ala Thr Met Phe Ser Thr Gln Ala Thr Glu Phe Asp Ser
            180                 185                 190

Glu Ala Thr Lys Glu Phe Lys Glu Ile Ile Glu Gly Val Ala Thr Ile
        195                 200                 205

Val Gly Val Ala Asn Phe Ala Asp Tyr Phe Pro Ile Leu Lys Pro Phe
    210                 215                 220

Asp Leu Gln Gly Ile Lys Arg Arg Ala Asp Gly Tyr Phe Gly Arg Leu
225                 230                 235                 240

Leu Lys Leu Ile Glu Gly Tyr Leu Asn Glu Arg Leu Glu Ser Arg Arg
                245                 250                 255

Leu Asn Pro Asp Ala Pro Arg Lys Lys Asp Phe Leu Glu Thr Leu Val
            260                 265                 270

Asp Ile Ile Glu Ala Asn Glu Tyr Lys Leu Thr Thr Glu His Leu Thr
        275                 280                 285

His Leu Met Leu Asp Leu Phe Val Gly Gly Ser Glu Thr Asn Thr Thr
    290                 295                 300

Ser Leu Glu Trp Ile Met Ser Glu Leu Val Ile Asn Pro Asp Lys Met
305                 310                 315                 320

Ala Lys Val Lys Glu Glu Leu Lys Ser Val Val Gly Asp Glu Lys Leu
                325                 330                 335

Val Asn Glu Ser Asp Met Pro Arg Leu Pro Tyr Leu Gln Ala Val Ile
            340                 345                 350

Lys Glu Val Leu Arg Ile His Pro Pro Gly Pro Leu Leu Leu Pro Arg
        355                 360                 365

Lys Ala Glu Ser Asp Gln Val Val Asn Gly Tyr Leu Ile Pro Lys Gly
    370                 375                 380

Thr Gln Ile Leu Phe Asn Ala Trp Ala Met Gly Arg Asp Pro Thr Ile
385                 390                 395                 400

Trp Lys Asp Pro Glu Ser Phe Glu Pro Glu Arg Phe Leu Asn Gln Ser
                405                 410                 415

Ile Asp Phe Lys Gly Gln Asp Phe Glu Leu Ile Pro Phe Gly Ser Gly
            420                 425                 430

Arg Arg Ile Cys Pro Gly Met Pro Leu Ala Asn Arg Ile Leu His Met
        435                 440                 445

Thr Thr Ala Thr Leu Val His Asn Phe Asp Trp Lys Leu Glu Glu Gly
    450                 455                 460

Thr Ala Asp Ala Asp His Lys Gly Glu Leu Phe Gly Leu Ala Val Arg
465                 470                 475                 480

Arg Ala Thr Pro Leu Arg Ile Ile Pro Leu Lys Pro
                485                 490

<210> SEQ ID NO 2
<211> LENGTH: 495
<212> TYPE: PRT
<213> ORGANISM: Coleus forskohlii

<400> SEQUENCE: 2

Met Glu Leu Val Gln Val Ile Ala Val Val Ala Val Val Val Val Leu
```

```
1               5                    10                   15
Trp Ser Gln Leu Lys Arg Lys Gly Arg Lys Leu Pro Pro Gly Pro Ser
            20                  25                  30

Pro Leu Pro Ile Val Gly Asn Ile Phe Gln Leu Ser Gly Lys Asn Ile
            35                  40                  45

Asn Glu Ser Phe Ala Lys Leu Ser Lys Ile Tyr Gly Pro Val Met Ser
        50                  55                  60

Leu Arg Leu Gly Ser Leu Leu Thr Val Ile Ile Ser Ser Pro Glu Met
65                  70                  75                  80

Ala Lys Glu Val Leu Thr Ser Lys Asp Phe Ala Asn Arg Pro Leu Thr
                85                  90                  95

Glu Ala Ala His Ala His Gly His Ser Lys Phe Ser Val Gly Phe Val
            100                 105                 110

Pro Val Ser Asp Pro Lys Trp Lys Gln Met Arg Arg Val Cys Gln Glu
            115                 120                 125

Glu Met Phe Ala Ser Arg Ile Leu Glu Asn Ser Gln Gln Arg Arg His
        130                 135                 140

Gln Lys Leu Gln Glu Leu Ile Asp His Val Gln Glu Ser Arg Asp Ala
145                 150                 155                 160

Gly Arg Ala Val Thr Ile Arg Asp Pro Val Phe Ala Thr Thr Leu Asn
                165                 170                 175

Ile Met Ser Leu Thr Leu Phe Ser Ala Asp Ala Thr Glu Phe Ser Ser
            180                 185                 190

Ser Ala Thr Ala Glu Leu Arg Asp Ile Met Ala Gly Val Val Ser Val
            195                 200                 205

Leu Gly Ala Ala Asn Leu Ala Asp Phe Phe Pro Ile Leu Lys Tyr Phe
210                 215                 220

Asp Pro Gln Gly Met Arg Arg Lys Ala Asp Leu His Tyr Gly Arg Leu
225                 230                 235                 240

Ile Asp His Ile Lys Ser Arg Met Asp Lys Arg Ser Glu Leu Lys Lys
                245                 250                 255

Ala Asn Pro Asn His Pro Lys His Asp Asp Phe Leu Glu Lys Ile Ile
            260                 265                 270

Asp Ile Thr Ile Gln Arg Asn Tyr Asp Leu Thr Ile Asn Glu Ile Thr
            275                 280                 285

His Leu Leu Val Asp Leu Tyr Leu Ala Gly Ser Glu Ser Thr Val Met
            290                 295                 300

Thr Ile Glu Trp Thr Met Ala Glu Leu Met Leu Arg Pro Glu Ser Leu
305                 310                 315                 320

Ala Lys Leu Lys Ala Glu Leu Arg Ser Val Met Gly Glu Arg Lys Met
                325                 330                 335

Ile Gln Glu Ser Asp Asp Ile Ser Arg Leu Pro Tyr Leu Asn Gly Ala
            340                 345                 350

Ile Lys Glu Ala Leu Arg Leu His Pro Pro Gly Pro Leu Leu Phe Ala
            355                 360                 365

Arg Lys Ser Glu Ile Asp Val Glu Leu Ser Gly Tyr Phe Ile Pro Lys
            370                 375                 380

Gly Thr Gln Ile Leu Val Asn Glu Trp Gly Met Gly Arg Asp Pro Ser
385                 390                 395                 400

Val Trp Pro Asn Pro Glu Cys Phe Gln Pro Glu Arg Phe Leu Asp Lys
                405                 410                 415

Asn Ile Asp Tyr Lys Gly Gln Asp Pro Gln Leu Ile Pro Phe Gly Ala
            420                 425                 430
```

```
Gly Arg Arg Ile Cys Pro Gly Ile Pro Ile Ala His Arg Val Val His
            435                 440                 445

Ser Val Val Ala Ala Leu Val His Asn Phe Asp Trp Glu Phe Ala Pro
    450                 455                 460

Gly Gly Ser Gln Cys Asn Asn Glu Phe Phe Thr Gly Ala Ala Leu Val
465                 470                 475                 480

Arg Glu Val Pro Leu Lys Leu Ile Pro Leu Asn Pro Pro Ser Ile
            485                 490                 495

<210> SEQ ID NO 3
<211> LENGTH: 496
<212> TYPE: PRT
<213> ORGANISM: Coleus forskohlii

<400> SEQUENCE: 3

Met Glu Phe Asp Phe Pro Ser Ala Leu Ile Phe Pro Ala Val Ser Leu
1               5                   10                  15

Leu Leu Leu Leu Trp Leu Thr Lys Thr Arg Lys Pro Lys Ser Asp Leu
            20                  25                  30

Asp Arg Ile Pro Gly Pro Arg Arg Leu Pro Leu Ile Gly Asn Leu His
            35                  40                  45

His Leu Ile Ser Leu Thr Pro Pro Arg Leu Phe Arg Glu Met Ala
    50                  55                  60

Ala Lys Tyr Gly Pro Leu Met Arg Leu Gln Leu Gly Gly Val Pro Phe
65                  70                  75                  80

Leu Ile Val Ser Ser Val Asp Val Ala Lys His Val Val Lys Thr Asn
                85                  90                  95

Asp Val Pro Phe Ala Asn Arg Pro Pro Met His Ala Ala Arg Ala Ile
            100                 105                 110

Thr Tyr Asn Tyr Thr Asp Ile Gly Phe Ala Pro Tyr Gly Glu Tyr Trp
            115                 120                 125

Arg Asn Leu Arg Lys Ile Cys Thr Leu Glu Leu Leu Ser Ala Arg Arg
        130                 135                 140

Val Arg Ser Phe Arg His Ile Arg Glu Glu Asn Ala Gly Val Ala
145                 150                 155                 160

Lys Trp Ile Ala Ser Lys Glu Gly Ser Pro Ala Asn Leu Ser Glu Arg
                165                 170                 175

Val Tyr Leu Ser Ser Phe Asp Ile Thr Ser Arg Ala Ser Ile Gly Lys
            180                 185                 190

Ala Thr Glu Glu Lys Gln Thr Leu Thr Ser Ser Ile Lys Asp Ala Met
        195                 200                 205

Lys Leu Gly Gly Phe Asn Val Ala Asp Leu Tyr Pro Ser Ser Lys Leu
    210                 215                 220

Leu Leu Leu Ile Thr Gly Leu Asn Phe Arg Ile Gln Arg Val Phe Arg
225                 230                 235                 240

Lys Thr Asp Arg Ile Leu Asp Asp Leu Leu Ser Gln His Arg Ser Thr
                245                 250                 255

Ser Ala Thr Thr Glu Arg Pro Glu Asp Leu Val Asp Val Leu Leu Lys
            260                 265                 270

Tyr Gln Lys Glu Glu Thr Glu Val His Leu Asn Asn Asp Lys Ile Lys
        275                 280                 285

Ala Val Ile Met Asp Met Phe Leu Ala Gly Gly Glu Thr Ser Ala Thr
    290                 295                 300

Ala Val Asp Trp Ala Met Ala Glu Met Ile Arg Asn Pro Thr Thr Leu
```

```
              305                 310                 315                 320
Lys Lys Ala Gln Glu Glu Val Arg Arg Val Phe Asp Gly Lys Gly Tyr
                325                 330                 335

Val Asp Glu Glu Glu Phe His Glu Leu Lys Tyr Leu Lys Leu Val Ile
                340                 345                 350

Lys Glu Met Leu Arg Met His Pro Pro Leu Pro Phe Leu Val Pro Arg
                355                 360                 365

Met Asn Ser Glu Arg Cys Glu Ile Asn Gly Tyr Glu Ile Pro Ala Asn
                370                 375                 380

Thr Arg Leu Leu Ile Asn Ala Trp Ala Ile Gly Arg Pro Lys Tyr Trp
385                 390                 395                 400

Asn Asp Ala Glu Lys Phe Ile Pro Glu Arg Phe Glu Asn Ser Ser Ile
                405                 410                 415

Asp Phe Lys Gly Asn Asn Leu Glu Tyr Ile Pro Phe Gly Ala Gly Arg
                420                 425                 430

Arg Met Cys Pro Gly Met Thr Phe Gly Leu Ala Ser Val Glu Phe Thr
                435                 440                 445

Leu Ala Met Leu Leu Tyr His Phe Asp Trp Lys Met Pro Gln Gly Ile
                450                 455                 460

Lys Leu Asp Met Thr Glu Ser Phe Gly Ala Ser Leu Lys Arg Lys His
465                 470                 475                 480

Asp Leu Leu Met Ile Pro Thr Leu Lys Arg Pro Leu Arg Leu Ala Pro
                485                 490                 495

<210> SEQ ID NO 4
<211> LENGTH: 500
<212> TYPE: PRT
<213> ORGANISM: Coleus forskohlii

<400> SEQUENCE: 4

Met Asp Phe Phe Thr Leu Leu Ala Ala Leu Phe Leu Ile Thr Leu Thr
1               5                   10                  15

Phe Phe Leu Phe Phe Lys Ser Glu Ser Lys Arg Arg Gly Gly Ala Asn
                20                  25                  30

Leu Pro Pro Gly Pro Tyr Pro Leu Pro Ile Val Gly Asn Ile Phe Gln
                35                  40                  45

Leu Gly Lys Lys Pro His Gln Ser Leu Ala Gln Leu Ala Lys Ile His
            50                  55                  60

Gly Pro Leu Met Ser Leu His Phe Gly Ser Val Tyr Thr Val Ile Val
65              70                  75                  80

Thr Ser Pro Glu Met Ala Lys Glu Ile Phe Val Lys Asn Asp Gln Ala
                85                  90                  95

Phe Leu Asn Arg Thr Val Val Glu Ala Val His Ala His Asp His Asp
                100                 105                 110

Lys Ile Ser Met Ala Phe Met Asp Val Gly Thr Glu Trp Arg Thr Leu
            115                 120                 125

Arg Arg Ile Cys Lys Glu Gln Met Phe Ser Thr Gln Ser Leu Glu Thr
        130                 135                 140

Ser Gln Gly Leu Arg Gln Glu Lys Leu Gln Gln Leu His Asp Phe Val
145                 150                 155                 160

Gln Arg Cys Cys Asp Ser Gly Arg Val Val Asp Ile Arg Glu Ala Ser
                165                 170                 175

Phe Val Thr Thr Leu Asn Leu Met Ser Ala Thr Leu Phe Ser Ile Gln
                180                 185                 190
```

```
Ala Thr Glu Phe Asp Ser Asn Ala Thr Glu Phe Arg Glu Ile Met
            195                 200                 205
Glu Gly Val Ala Ser Ile Val Gly Asp Pro Asn Phe Ala Asp Tyr Phe
    210                 215                 220
Pro Ile Leu Lys Arg Phe Asp Pro Gln Gly Val Lys Arg Lys Ala Glu
225                 230                 235                 240
Leu Tyr Phe Gly Lys Met Leu Val Leu Val Glu Asp Leu Leu Gln Lys
                245                 250                 255
Arg Gln Glu Glu Arg Arg Arg Ser Pro Ser Tyr Ala Lys Lys Asp Asp
            260                 265                 270
Leu Leu Glu Arg Leu Val Asp Val Leu Asn Glu Lys Asn Glu Tyr Lys
        275                 280                 285
Leu Thr Thr Lys His Ile Thr His Leu Leu Leu Asp Leu Phe Val Gly
    290                 295                 300
Gly Ser Glu Thr Thr Thr Thr Ser Val Glu Trp Ile Met Ser Glu Leu
305                 310                 315                 320
Leu Ile Asn Pro Glu Lys Leu Ala Lys Leu Lys Glu Glu Leu Lys Thr
                325                 330                 335
Val Val Gly Glu Lys Lys Gln Val Gln Glu Ser Asp Ile Pro Gln Leu
            340                 345                 350
Pro Tyr Phe Glu Ala Val Leu Lys Glu Val Phe Arg Leu His Pro Pro
        355                 360                 365
Gly Pro Leu Leu Leu Pro Arg Lys Ala Glu Cys Asp Val Gln Val Gly
    370                 375                 380
Ser Tyr Thr Ile Pro Lys Glu Thr Gln Ile Leu Val Asn Ala Trp Ala
385                 390                 395                 400
Ile Gly Arg Asp Pro Ala Ile Trp Pro Asn Pro Glu Ala Phe Glu Pro
                405                 410                 415
Glu Arg Phe Leu Ser Gln Lys Met Asp Tyr Lys Gly Gln Asp Phe Glu
            420                 425                 430
Leu Ile Pro Phe Gly Ser Gly Arg Arg Ile Cys Pro Gly Leu Ser Phe
        435                 440                 445
Ala Asn Arg Met Leu Pro Met Thr Val Ala Thr Leu Ile His Asn Phe
    450                 455                 460
Asp Trp Lys Leu Glu Val Glu Ala Asn Ala Glu Asp Val His Lys Gly
465                 470                 475                 480
Glu Met Phe Gly Ile Ala Val Arg Arg Ala Val Pro Leu Arg Ala Tyr
                485                 490                 495
Pro Ile Gln Pro
            500

<210> SEQ ID NO 5
<211> LENGTH: 1479
<212> TYPE: DNA
<213> ORGANISM: Artificial sequence
<220> FEATURE:
<223> OTHER INFORMATION: DNA sequence codon optimised for expression in
      yeast

<400> SEQUENCE: 5
atggaaacca tcaccttgtt gttggccttg tttttcattg ctttgaccta cttcatctcc      60
tccagaagaa gaagaaattt gccaccaggt ccatttccat tgccaattat tggtaacatg     120
ttgcaattgg ttccaagcc acatcaatct tttgctcaat gtccaaaaaa gtacggtcca      180
ttgatgtcca ttcatttggg ttccttgtac accgttatag tctcttcacc agaaatggcc     240
```

```
aaagaaatct tgcaaaaaca cggtcaagtt ttctccggta gaactattgc tcaagctgtt      300
catgcttgtg atcacgataa gatttctatg ggttttttgc cagttgccaa cacttggaga      360
gatatgagaa agatctgcaa agaacaaatg ttctcccacc attctttgga agctagtgaa      420
gaattgagac accaaaagtt gcaacaatta ttagactacg ctcaaaagtg ttgcgaagct      480
ggtagagctg ttgatattag agaagcctct ttcattacca ccttgaactt gatgtctgct      540
actatgtttt ctacccaagc taccgaattt gattccgaag ctacaaaaga attcaaagaa      600
attatcgaag gtgtcgccac tatagttggt gttgctaatt ttgctgatta cttcccaatc      660
ttgaagccat ttgacttgca aggtattaag agaagagctg atggttactt cggtagatta      720
ttgaagttga tcgaaggtta cttgaacgaa agattggaat ctagaagatt gaacccagat      780
gctccaagaa agaaggattt cttggaaacc ttggttgata tcatcgaagc caacgaatac      840
aagttgacta ctgaacattt gacccacttg atgttggatt tgtttgttgg tggttctgaa      900
actaacacca catccttgga atggatcatg tctgaattgg ttatcaaccc agataagatg      960
gccaaggtca aagaagaatt gaagtctgtt gttggtgacg aaaagttggt taacgaatct     1020
gatatgccaa gattgccata cttgcaagcc gttatcaaag aagttttgag aattcatcca     1080
cctggtcctt tgttgttgcc aagaaaagct gaatctgatc aagttgttaa cggttatttg     1140
atcccaaagg gtactcaaat tttgttcaat gcttgggcta tgggtagaga tccaactatt     1200
tggaaagatc cagaatcctt cgaaccagaa agattcttga atcaatccat cgacttcaag     1260
ggtcaagact tcgaattgat tccatttggt tctggtagaa gaatctgtcc aggtatgcca     1320
ttggctaata gaatcttgca tatgactacc gccacttttgg ttcataattt cgattggaaa     1380
ttggaagaag gtactgctga cgctgatcat aagggtgaat tatttggttt ggctgttaga     1440
agagctaccc cattgagaat cattccattg aaaccataa                            1479

<210> SEQ ID NO 6
<211> LENGTH: 1488
<212> TYPE: DNA
<213> ORGANISM: Artificial sequence
<220> FEATURE:
<223> OTHER INFORMATION: DNA sequence codon optimised for expression in
      yeast

<400> SEQUENCE: 6
atggaattgg tccaagttat cgctgttgtt gcagttgttg ttgttttgtg gtcccaattg       60
aaaagaaagg gtagaaaatt gccaccaggt ccatctccat tgccaatagt tggtaatatc      120
ttccaattgt ccggtaagaa catcaacgaa tctttcgcta gttgtccaa atctacggt       180 ccagttatgt ctttgagatt gggttctttg ttgaccgtca ttatctcttc accagaaatg      240 gccaagaag tcttgacttc taaggatttt gctaacagac cattgactga agctgctcat      300
gctcatggtc attctaaatt ttctgttggt ttcgttccag tctctgatcc aaaatggaaa      360
caaatgagaa gagtctgcca agaagaaatg ttcgcctcta gaattttgga aaactcccaa      420
caaagaagac accaaaagtt gcaagaattg atcgaccacg ttcaagaatc tagagatgct      480
ggtagagctg ttactattag agatccagtt ttcgctacca ccttgaacat tatgtccttg      540
actttgtttt ctgccgatgc tactgaattc tcttcttctg ctactgctga attgagagat      600
attatggctg tgttgtttc tgtttttggt gctgctaatt tggctgattt cttcccaatc      660
ttgaaatact tcgatccaca aggtatgaga agaaaggctg acttgcatta cggtagattg      720
attgaccata tcaagtccag aatggacaag agatctgaat tgaagaaggc taatccaaac      780
```

```
catccaaagc acgatgattt cttggaaaag atcatcgaca tcaccattca agaaactac    840
gacttgacca ttaacgaaat cacccatttg ttggtcgact tgtatttggc tggttctgaa    900
tctactgtta tgaccattga atggaccatg gccgaattga tgttaagacc agaatcattg    960
gctaaattga aggcagaatt gagatccgtt atgggtgaaa gaaagatgat ccaagaatcc   1020
gacgacattt ctagattgcc atacttaaac ggtgctatca agaagccttt aagattgcat   1080
ccacctggtc ctttgttgtt tgctagaaag tctgaaatcg atgttgaatt gtctggttac   1140
ttcatcccaa agggtactca aatcttggtt aatgaatggg gtatgggtag agatccttct   1200
gtttggccta atccagaatg ttttcaacca gaaagatttt tggataagaa cattgactac   1260
aagggtcaag acccacaatt gattccattt ggtgcaggta agaatttg tccaggtatt   1320
ccaattgccc atagagttgt tcattcagtt gttgctgctt tggttcataa cttcgattgg   1380
gaatttgctc ctggtggttc tcaatgtaac aacgaatttt tcactggtgc tgccttggtt   1440
agagaagttc cattgaagtt gattcctttg aacccaccat ccatctga              1488
```

<210> SEQ ID NO 7
<211> LENGTH: 773
<212> TYPE: PRT
<213> ORGANISM: Coleus forskohlii

<400> SEQUENCE: 7

```
Met Lys Met Leu Met Ile Lys Ser Gln Phe Arg Val His Ser Ile Val
1               5                   10                  15

Ser Ala Trp Ala Asn Asn Ser Asn Lys Arg Gln Ser Leu Gly His Gln
            20                  25                  30

Ile Arg Arg Lys Gln Arg Ser Gln Val Thr Glu Cys Arg Val Ala Ser
        35                  40                  45

Leu Asp Ala Leu Asn Gly Ile Gln Lys Val Gly Pro Ala Thr Ile Gly
    50                  55                  60

Thr Pro Glu Glu Glu Asn Lys Lys Ile Glu Asp Ser Ile Glu Tyr Val
65                  70                  75                  80

Lys Glu Leu Leu Lys Thr Met Gly Asp Gly Arg Ile Ser Val Ser Pro
                85                  90                  95

Tyr Asp Thr Ala Ile Val Ala Leu Ile Lys Asp Leu Glu Gly Gly Asp
            100                 105                 110

Gly Pro Glu Phe Pro Ser Cys Leu Glu Trp Ile Ala Gln Asn Gln Leu
        115                 120                 125

Ala Asp Gly Ser Trp Gly Asp His Phe Phe Cys Ile Tyr Asp Arg Val
    130                 135                 140

Val Asn Thr Ala Ala Cys Val Val Ala Leu Lys Ser Trp Asn Val His
145                 150                 155                 160

Ala Asp Lys Ile Glu Lys Gly Ala Val Tyr Leu Lys Glu Asn Val His
                165                 170                 175

Lys Leu Lys Asp Gly Lys Ile Glu His Met Pro Ala Gly Phe Glu Phe
            180                 185                 190

Val Val Pro Ala Thr Leu Glu Arg Ala Lys Ala Leu Gly Ile Lys Gly
        195                 200                 205

Leu Pro Tyr Asp Asp Pro Phe Ile Arg Glu Ile Tyr Ser Ala Lys Gln
    210                 215                 220

Thr Arg Leu Thr Lys Ile Pro Lys Gly Met Ile Tyr Glu Ser Pro Thr
225                 230                 235                 240

Ser Leu Leu Tyr Ser Leu Asp Gly Leu Glu Gly Leu Glu Trp Asp Lys
                245                 250                 255
```

```
Ile Leu Lys Leu Gln Ser Ala Asp Gly Ser Phe Ile Thr Ser Val Ser
            260                 265                 270

Ser Thr Ala Phe Val Phe Met His Thr Asn Asp Leu Lys Cys His Ala
            275                 280                 285

Phe Ile Lys Asn Ala Leu Thr Asn Cys Asn Gly Gly Val Pro His Thr
            290                 295                 300

Tyr Pro Val Asp Ile Phe Ala Arg Leu Trp Ala Val Asp Arg Leu Gln
305                 310                 315                 320

Arg Leu Gly Ile Ser Arg Phe Phe Glu Pro Glu Ile Lys Tyr Leu Met
                325                 330                 335

Asp His Ile Asn Asn Val Trp Arg Glu Lys Gly Val Phe Ser Ser Arg
            340                 345                 350

His Ser Gln Phe Ala Asp Ile Asp Asp Thr Ser Met Gly Ile Arg Leu
            355                 360                 365

Leu Lys Met His Gly Tyr Asn Val Asn Pro Asn Ala Leu Glu His Phe
            370                 375                 380

Lys Gln Lys Asp Gly Lys Phe Thr Cys Tyr Ala Asp Gln His Ile Glu
385                 390                 395                 400

Ser Pro Ser Pro Met Tyr Asn Leu Tyr Arg Ala Ala Gln Leu Arg Phe
                405                 410                 415

Pro Gly Glu Glu Ile Leu Gln Gln Ala Leu Gln Phe Ala Tyr Asn Phe
            420                 425                 430

Leu His Glu Asn Leu Ala Ser Asn His Phe Gln Glu Lys Trp Val Ile
            435                 440                 445

Ser Asp His Leu Ile Asp Glu Val Arg Ile Gly Leu Lys Met Pro Trp
450                 455                 460

Tyr Ala Thr Leu Pro Arg Val Glu Ala Ser Tyr Tyr Leu Gln His Tyr
465                 470                 475                 480

Gly Gly Ser Ser Asp Val Trp Ile Gly Lys Thr Leu Tyr Arg Met Pro
                485                 490                 495

Glu Ile Ser Asn Asp Thr Tyr Lys Ile Leu Ala Gln Leu Asp Phe Asn
            500                 505                 510

Lys Cys Gln Ala Gln His Gln Leu Glu Trp Met Ser Met Lys Glu Trp
            515                 520                 525

Tyr Gln Ser Asn Val Lys Glu Phe Gly Ile Ser Lys Lys Glu Leu
530                 535                 540

Leu Leu Ala Tyr Phe Leu Ala Ala Thr Met Phe Glu Pro Glu Arg
545                 550                 555                 560

Thr Gln Glu Arg Ile Met Trp Ala Lys Thr Gln Val Val Ser Arg Met
                565                 570                 575

Ile Thr Ser Phe Leu Asn Lys Glu Asn Thr Met Ser Phe Asp Leu Lys
            580                 585                 590

Ile Ala Leu Leu Thr Gln Pro Gln His Gln Ile Asn Gly Ser Glu Met
            595                 600                 605

Lys Asn Gly Leu Ala Gln Thr Leu Pro Ala Ala Phe Arg Gln Leu Leu
            610                 615                 620

Lys Glu Phe Asp Lys Tyr Thr Arg His Gln Leu Arg Asn Thr Trp Asn
625                 630                 635                 640

Lys Trp Leu Met Lys Leu Lys Gln Gly Asp Asp Asn Gly Ala Asp
                645                 650                 655

Ala Glu Leu Leu Ala Asn Thr Leu Asn Ile Cys Ala Gly His Asn Glu
            660                 665                 670
```

```
Asp Ile Leu Ser His Tyr Glu Tyr Thr Ala Leu Ser Ser Leu Thr Asn
            675                 680                 685

Lys Ile Cys Gln Arg Leu Ser Gln Ile Gln Asp Lys Lys Met Leu Glu
        690                 695                 700

Ile Glu Glu Gly Ser Ile Lys Asp Lys Glu Met Glu Leu Glu Ile Gln
705                 710                 715                 720

Thr Leu Val Lys Leu Val Leu Gln Glu Thr Ser Gly Gly Ile Asp Arg
            725                 730                 735

Asn Ile Lys Gln Thr Phe Leu Ser Val Phe Lys Thr Phe Tyr Tyr Arg
            740                 745                 750

Ala Tyr His Asp Ala Lys Thr Ile Asp Ala His Ile Phe Gln Val Leu
755                 760                 765

Phe Glu Pro Val Val
    770

<210> SEQ ID NO 8
<211> LENGTH: 598
<212> TYPE: PRT
<213> ORGANISM: Coleus forskohlii

<400> SEQUENCE: 8

Met Ser Ser Leu Ala Gly Asn Leu Arg Val Ile Pro Phe Ser Gly Asn
1               5                   10                  15

Arg Val Gln Thr Arg Thr Gly Ile Leu Pro Val His Gln Thr Pro Met
            20                  25                  30

Ile Thr Ser Lys Ser Ser Ala Ala Val Lys Cys Ser Leu Thr Thr Pro
        35                  40                  45

Thr Asp Leu Met Gly Lys Ile Lys Glu Val Phe Asn Arg Glu Val Asp
50                  55                  60

Thr Ser Pro Ala Ala Met Thr Thr His Ser Thr Asp Ile Pro Ser Asn
65                  70                  75                  80

Leu Cys Ile Ile Asp Thr Leu Gln Arg Leu Gly Ile Asp Gln Tyr Phe
                85                  90                  95

Gln Ser Glu Ile Asp Ala Val Leu His Asp Thr Tyr Arg Leu Trp Gln
            100                 105                 110

Leu Lys Lys Lys Asp Ile Phe Ser Asp Ile Thr Thr His Ala Met Ala
        115                 120                 125

Phe Arg Leu Leu Arg Val Lys Gly Tyr Glu Val Ala Ser Asp Glu Leu
130                 135                 140

Ala Pro Tyr Ala Asp Gln Glu Arg Ile Asn Leu Gln Thr Ile Asp Val
145                 150                 155                 160

Pro Thr Val Val Glu Leu Tyr Arg Ala Ala Gln Glu Arg Leu Thr Glu
                165                 170                 175

Glu Asp Ser Thr Leu Glu Lys Leu Tyr Val Trp Thr Ser Ala Phe Leu
            180                 185                 190

Lys Gln Gln Leu Leu Thr Asp Ala Ile Pro Asp Lys Lys Leu His Lys
        195                 200                 205

Gln Val Glu Tyr Tyr Leu Lys Asn Tyr His Gly Ile Leu Asp Arg Met
210                 215                 220

Gly Val Arg Arg Asn Leu Asp Leu Tyr Asp Ile Ser Tyr Lys Ser
225                 230                 235                 240

Leu Lys Ala Ala His Arg Phe Tyr Asn Leu Ser Asn Glu Asp Ile Leu
                245                 250                 255

Ala Phe Ala Arg Gln Asp Phe Asn Ile Ser Gln Ala Gln His Gln Lys
            260                 265                 270
```

Glu Leu Gln Gln Leu Gln Arg Trp Tyr Ala Asp Cys Arg Leu Asp Thr
    275                 280                 285

Leu Lys Phe Gly Arg Asp Val Arg Ile Gly Asn Phe Leu Thr Ser
290                 295                 300

Ala Met Ile Gly Asp Pro Glu Leu Ser Asp Leu Arg Leu Ala Phe Ala
305                 310                 315                 320

Lys His Ile Val Leu Val Thr Arg Ile Asp Asp Phe Asp His Gly
            325                 330                 335

Gly Pro Lys Glu Glu Ser Tyr Glu Ile Leu Glu Leu Val Lys Glu Trp
            340                 345                 350

Lys Glu Lys Pro Ala Gly Glu Tyr Val Ser Glu Val Glu Ile Leu
            355                 360                 365

Phe Thr Ala Val Tyr Asn Thr Val Asn Glu Leu Ala Glu Met Ala His
370                 375                 380

Ile Glu Gln Gly Arg Ser Val Lys Asp Leu Leu Val Lys Leu Trp Val
385                 390                 395                 400

Glu Ile Leu Ser Val Phe Arg Ile Glu Leu Asp Thr Trp Thr Asn Asp
                405                 410                 415

Thr Ala Leu Thr Leu Glu Glu Tyr Leu Ser Gln Ser Trp Val Ser Ile
            420                 425                 430

Gly Cys Arg Ile Cys Ile Leu Ile Ser Met Gln Phe Gln Gly Val Lys
            435                 440                 445

Leu Ser Asp Glu Met Leu Gln Ser Glu Glu Cys Thr Asp Leu Cys Arg
450                 455                 460

Tyr Val Ser Met Val Asp Arg Leu Leu Asn Asp Val Gln Thr Phe Glu
465                 470                 475                 480

Lys Glu Arg Lys Glu Asn Thr Gly Asn Ser Val Ser Leu Leu Gln Ala
                485                 490                 495

Ala His Lys Asp Glu Arg Val Ile Asn Glu Glu Ala Cys Ile Lys
            500                 505                 510

Val Lys Glu Leu Ala Glu Tyr Asn Arg Arg Lys Leu Met Gln Ile Val
            515                 520                 525

Tyr Lys Thr Gly Thr Ile Phe Pro Arg Lys Cys Lys Asp Leu Phe Leu
            530                 535                 540

Lys Ala Cys Arg Ile Gly Cys Tyr Leu Tyr Ser Ser Gly Asp Glu Phe
545                 550                 555                 560

Thr Ser Pro Gln Gln Met Met Glu Asp Met Lys Ser Leu Val Tyr Glu
                565                 570                 575

Pro Leu Pro Ile Ser Pro Pro Glu Ala Asn Asn Ala Ser Gly Glu Lys
            580                 585                 590

Met Ser Cys Val Ser Asn
            595

<210> SEQ ID NO 9
<211> LENGTH: 587
<212> TYPE: PRT
<213> ORGANISM: Coleus forskohlii

<400> SEQUENCE: 9

Met Ser Ile Thr Ile Asn Leu Arg Val Ile Ala Phe Pro Gly His Gly
1               5                   10                  15

Val Gln Ser Arg Gln Gly Ile Phe Ala Val Met Glu Phe Pro Arg Asn
            20                  25                  30

Lys Asn Thr Phe Lys Ser Ser Phe Ala Val Lys Cys Ser Leu Ser Thr

```
                35                  40                  45
Pro Thr Asp Leu Met Gly Lys Ile Lys Glu Lys Leu Ser Glu Lys Val
50                  55                  60
Asp Asn Ser Val Ala Ala Met Ala Thr Asp Ser Ala Asp Met Pro Thr
65                  70                  75                  80
Asn Leu Cys Ile Val Asp Ser Leu Gln Arg Leu Gly Val Glu Lys Tyr
                85                  90                  95
Phe Gln Ser Glu Ile Asp Thr Val Leu Asp Asp Ala Tyr Arg Leu Trp
                100                 105                 110
Gln Leu Lys Gln Lys Asp Ile Phe Ser Asp Ile Thr Thr His Ala Met
                115                 120                 125
Ala Phe Arg Leu Leu Arg Val Lys Gly Tyr Asp Val Ser Ser Glu Glu
                130                 135                 140
Leu Ala Pro Tyr Ala Asp Gln Glu Gly Met Asn Leu Gln Thr Ile Asp
145                 150                 155                 160
Leu Ala Ala Val Ile Glu Leu Tyr Arg Ala Ala Gln Glu Arg Val Ala
                165                 170                 175
Glu Glu Asp Ser Thr Leu Glu Lys Leu Tyr Val Trp Thr Ser Thr Phe
                180                 185                 190
Leu Lys Gln Gln Leu Leu Ala Gly Ala Ile Pro Asp Gln Lys Leu His
                195                 200                 205
Lys Gln Val Glu Tyr Tyr Leu Lys Asn Tyr His Gly Ile Leu Asp Arg
                210                 215                 220
Met Gly Val Arg Lys Gly Leu Asp Leu Tyr Asp Ala Gly Tyr Tyr Lys
225                 230                 235                 240
Ala Leu Lys Ala Ala Asp Arg Leu Val Asp Leu Cys Asn Glu Asp Leu
                245                 250                 255
Leu Ala Phe Ala Arg Gln Asp Phe Asn Ile Asn Gln Ala Gln His Arg
                260                 265                 270
Lys Glu Leu Glu Gln Leu Gln Arg Trp Tyr Ala Asp Cys Arg Leu Asp
                275                 280                 285
Lys Leu Glu Phe Gly Arg Asp Val Val Arg Val Ser Asn Phe Leu Thr
                290                 295                 300
Ser Ala Ile Leu Gly Asp Pro Glu Leu Ser Glu Val Arg Leu Val Phe
305                 310                 315                 320
Ala Lys His Ile Val Leu Val Thr Arg Ile Asp Asp Phe Phe Asp His
                325                 330                 335
Gly Gly Pro Arg Glu Glu Ser His Lys Ile Leu Glu Leu Ile Lys Glu
                340                 345                 350
Trp Lys Glu Lys Pro Ala Gly Glu Tyr Val Ser Lys Glu Val Glu Ile
                355                 360                 365
Leu Tyr Thr Ala Val Tyr Asn Thr Val Asn Glu Leu Ala Glu Arg Ala
                370                 375                 380
Asn Val Glu Gln Gly Arg Asn Val Glu Pro Phe Leu Arg Thr Leu Trp
385                 390                 395                 400
Val Gln Ile Leu Ser Ile Phe Lys Ile Glu Leu Asp Thr Trp Ser Asp
                405                 410                 415
Asp Thr Ala Leu Thr Leu Asp Asp Tyr Leu Asn Asn Ser Trp Val Ser
                420                 425                 430
Ile Gly Cys Arg Ile Cys Ile Leu Met Ser Met Gln Phe Ile Gly Met
                435                 440                 445
Lys Leu Pro Glu Glu Met Leu Leu Ser Glu Glu Cys Val Asp Leu Cys
                450                 455                 460
```

```
Arg His Val Ser Met Val Asp Arg Leu Leu Asn Asp Val Gln Thr Phe
465                 470                 475                 480

Glu Lys Glu Arg Lys Glu Asn Thr Gly Asn Ala Val Ser Leu Leu Leu
            485                 490                 495

Ala Ala His Lys Gly Glu Arg Ala Phe Ser Glu Glu Ala Ile Ala
            500                 505                 510

Lys Ala Lys Tyr Leu Ala Asp Cys Asn Arg Arg Ser Leu Met Gln Ile
            515                 520                 525

Val Tyr Lys Thr Gly Thr Ile Phe Pro Arg Lys Cys Lys Asp Met Phe
            530                 535                 540

Leu Lys Val Cys Arg Ile Gly Cys Tyr Leu Tyr Ala Ser Gly Asp Glu
545                 550                 555                 560

Phe Thr Ser Pro Gln Gln Met Met Glu Asp Met Lys Ser Leu Val Tyr
                565                 570                 575

Glu Pro Leu Gln Ile His Pro Pro Ala Asn
            580                 585

<210> SEQ ID NO 10
<211> LENGTH: 493
<212> TYPE: PRT
<213> ORGANISM: Coleus forskohlii

<400> SEQUENCE: 10

Met Glu Ser Met Asn Ala Leu Val Val Gly Leu Leu Leu Ile Ala Leu
1               5                   10                  15

Thr Ile Leu Phe Ser Leu Arg Arg Arg Asn Leu Ala Pro Gly Pro
            20                  25                  30

Tyr Pro Phe Pro Ile Ile Gly Asn Met Leu Gln Leu Gly Thr Lys Pro
                35                  40                  45

His Gln Ser Phe Ala Gln Leu Ser Lys Lys Tyr Gly Pro Leu Met Ser
            50                  55                  60

Ile His Leu Gly Ser Leu Tyr Thr Val Ile Val Ser Ser Pro Glu Met
65                  70                  75                  80

Ala Lys Glu Ile Leu Gln Lys His Gly Gln Val Phe Ser Gly Arg Thr
                85                  90                  95

Ile Ala Gln Ala Val His Ala Cys Asp His Asp Lys Ile Ser Met Gly
            100                 105                 110

Phe Leu Pro Val Ser Asn Thr Trp Arg Asp Met Arg Lys Ile Cys Lys
            115                 120                 125

Glu Gln Met Phe Ser His His Ser Leu Glu Gly Ser Gln Gly Leu Arg
130                 135                 140

Gln Gln Lys Leu Leu Gln Leu Leu Asp Tyr Ala Gln Lys Cys Cys Glu
145                 150                 155                 160

Thr Gly Arg Ala Val Asp Ile Arg Glu Ala Ser Phe Ile Thr Thr Leu
                165                 170                 175

Asn Leu Met Ser Ala Thr Met Phe Ser Thr Gln Ala Thr Glu Phe Glu
            180                 185                 190

Ser Lys Ser Thr Gln Glu Phe Lys Glu Ile Ile Glu Gly Val Ala Thr
            195                 200                 205

Ile Val Gly Val Ala Asn Phe Gly Asp Tyr Phe Pro Ile Leu Lys Pro
            210                 215                 220

Phe Asp Leu Gln Gly Ile Lys Arg Lys Ala Asp Gly Tyr Phe Gly Arg
225                 230                 235                 240

Leu Leu Lys Leu Ile Glu Gly Tyr Leu Asn Glu Arg Leu Glu Ser Arg
```

```
                245                 250                 255
Lys Ser Asn Pro Asn Ala Pro Arg Lys Asn Asp Phe Leu Glu Thr Val
            260                 265                 270

Val Asp Ile Leu Glu Ala Asn Glu Tyr Lys Leu Ser Val Asp His Leu
        275                 280                 285

Thr His Leu Met Leu Asp Phe Val Gly Gly Ser Glu Thr Asn Thr
    290                 295                 300

Thr Ser Leu Glu Trp Thr Met Ser Glu Leu Val Asn Asn Pro Asp Lys
305                 310                 315                 320

Met Ala Lys Leu Lys Gln Glu Leu Lys Ser Val Val Gly Glu Arg Lys
                325                 330                 335

Leu Val Asp Glu Ser Glu Met Pro Arg Leu Pro Tyr Leu Gln Ala Val
            340                 345                 350

Ile Lys Glu Ser Leu Arg Ile His Pro Pro Gly Pro Leu Leu Leu Pro
        355                 360                 365

Arg Lys Ala Glu Thr Asp Gln Glu Val Asn Gly Tyr Leu Ile Pro Lys
    370                 375                 380

Gly Thr Gln Ile Leu Phe Asn Val Trp Ala Met Gly Arg Asp Pro Ser
385                 390                 395                 400

Ile Trp Lys Asp Pro Glu Ser Phe Glu Pro Glu Arg Phe Leu Asn Gln
                405                 410                 415

Asn Ile Asp Phe Lys Gly Gln Asp Phe Glu Leu Ile Pro Phe Gly Ser
            420                 425                 430

Gly Arg Arg Ile Cys Pro Gly Met Pro Leu Ala Asn Arg Ile Leu His
        435                 440                 445

Met Ala Thr Ala Thr Met Val His Asn Phe Asp Trp Lys Leu Glu Gln
    450                 455                 460

Gly Thr Asp Glu Ala Asp Ala Lys Gly Glu Leu Phe Gly Leu Ala Val
465                 470                 475                 480

Arg Arg Ala Val Pro Leu Arg Ile Ile Pro Leu Gln Pro
                485                 490

<210> SEQ ID NO 11
<211> LENGTH: 493
<212> TYPE: PRT
<213> ORGANISM: Coleus forskohlii

<400> SEQUENCE: 11

Met Glu Thr Met Thr Leu Leu Leu Pro Leu Phe Phe Ile Ala Leu Thr
1               5                   10                  15

Tyr Phe Leu Ser Trp Arg Arg Arg Asn Leu Pro Pro Gly Pro Phe
            20                  25                  30

Pro Leu Pro Ile Ile Gly Asn Leu Leu Gln Ile Gly Ser Lys Pro His
        35                  40                  45

Gln Ser Phe Ala Gln Leu Ser Lys Lys Tyr Gly Pro Leu Met Ser Val
    50                  55                  60

Gln Leu Gly Ser Val Tyr Thr Val Ile Ala Ser Ser Pro Glu Met Ala
65                  70                  75                  80

Lys Glu Ile Leu Gln Lys His Gly Gln Val Phe Ser Gly Arg Thr Ile
                85                  90                  95

Ala Gln Ala Ala Gln Ala Cys Gly His Asp Gln Ile Ser Ile Gly Phe
            100                 105                 110

Leu Pro Val Ala Thr Thr Trp Arg Asp Met Arg Lys Ile Cys Lys Glu
        115                 120                 125
```

```
Gln Met Phe Ser His His Ser Leu Glu Ser Ser Lys Glu Leu Arg His
    130                 135                 140

Glu Lys Leu Gln Lys Leu Leu Asp Tyr Ala Gln Lys Cys Cys Glu Ala
145                 150                 155                 160

Gly Arg Ala Val Asp Ile Arg Glu Ala Ala Phe Ile Thr Thr Leu Asn
                165                 170                 175

Leu Met Ser Ala Thr Leu Phe Ser Thr Gln Ala Thr Glu Phe Asp Ser
            180                 185                 190

Glu Ala Thr Lys Glu Phe Lys Glu Val Ile Glu Val Ala Val Ile
        195                 200                 205

Val Gly Glu Pro Asn Phe Ala Asp Tyr Phe Pro Ile Leu Lys Pro Phe
210                 215                 220

Asp Leu Gln Gly Ile Lys Arg Arg Ala Asn Ser Tyr Phe Gly Arg Leu
225                 230                 235                 240

Leu Lys Leu Met Glu Arg Tyr Leu Asn Glu Arg Leu Glu Ser Arg Arg
                245                 250                 255

Leu Asn Pro Asp Ala Pro Lys Lys Asn Asp Phe Leu Glu Thr Leu Val
            260                 265                 270

Asp Ile Ile Gln Ala Asp Glu Tyr Lys Leu Thr Thr Asp His Val Thr
        275                 280                 285

His Leu Met Leu Asp Leu Phe Val Gly Gly Ser Glu Thr Ser Ala Thr
    290                 295                 300

Ser Leu Glu Trp Ile Met Ser Glu Leu Val Ser Asn Pro Ser Lys Leu
305                 310                 315                 320

Ala Lys Val Lys Ala Glu Leu Lys Ser Val Val Gly Glu Lys Lys Val
                325                 330                 335

Val Ser Glu Ser Glu Met Ala Arg Leu Pro Tyr Leu Gln Ala Val Ile
            340                 345                 350

Lys Glu Val Leu Arg Leu His Pro Pro Gly Pro Leu Leu Leu Pro Arg
        355                 360                 365

Lys Ala Gly Ser Asp Gln Val Val Asn Gly Tyr Leu Ile Pro Lys Gly
    370                 375                 380

Thr Gln Leu Leu Phe Asn Val Trp Ala Met Gly Arg Asp Pro Ser Ile
385                 390                 395                 400

Trp Lys Asn Pro Glu Ser Phe Glu Pro Glu Arg Phe Leu Asn Gln Asn
                405                 410                 415

Ile Asp Tyr Lys Gly Gln Asp Phe Glu Leu Ile Pro Phe Gly Ser Gly
            420                 425                 430

Arg Arg Ile Cys Pro Gly Met Pro Leu Ala Asp Arg Ile Met His Met
        435                 440                 445

Thr Thr Ala Thr Leu Val His Asn Phe Asp Trp Lys Leu Glu Asp Gly
    450                 455                 460

Ala Gly Asp Ala Asp His Lys Gly Asp Asp Pro Phe Gly Leu Ala Ile
465                 470                 475                 480

Arg Arg Ala Thr Pro Leu Arg Ile Ile Pro Leu Lys Pro
                485                 490

<210> SEQ ID NO 12
<211> LENGTH: 1482
<212> TYPE: DNA
<213> ORGANISM: Coleus forskohlii

<400> SEQUENCE: 12
atggaaacca tgactcttct cctccctctt ttcttcatcg ctctgacata tttcctctcc    60
```

```
tggaggcgcc ggagaaacct tcctccgggg ccttttcctc ttccaatcat cggaaacttg      120
ctgcaaatcg gctccaaacc ccaccagtca ttcgcccaac tctcaaagaa atatgggcct      180
ctcatgtccg tccaactcgg gagtgtatac accgtgatag cctcctcccc ggaaatggcg      240
aaagagatac tgcaaaaaca cggccaagtg ttttccggga gaaccatcgc acaggcggcg      300
caagcgtgcg ccacgaccag atctccatc ggtttctgc cggtggcaac cacgtggcgt       360
gatatgcgta aaatatgcaa agaacagatg ttctcgcatc acagcctgga atccagcaag      420
gagctgaggc acgagaagct gcagaagctg ctggactacg cccagaaatg ctgcgaagcc      480
ggccgtgccg ttgatattcg tgaggccgcc ttcattacaa cgctcaacct catgtctgcc      540
acgttgttct cgactcaagc tactgagttc gactccgaag ctacaaaaga gtttaaggag      600
gtcatcgagg gggtggccgt cattgtgggt gagcctaatt cgctgactaa cttccccatc      660
ttgaagcctt tcgatcttca ggggatcaag cgtagagcta atagctactt tggaagactg      720
ctcaagttaa tggagagata tctgaatgag aggctggaat caagaaggtt gaacccagat      780
gcccccaaga agaatgactt tttggaaacc ctggtggata tcatccaggc tgatgaatac      840
aagctcacga ccgaccacgt cacgcacctc atgcttgact tatttgttgg aggatcggaa      900
acaagcgcga cctcactgga atggataatg tcggagttag tgagcaatcc gagtaaattg      960
gcgaaggtga aagcggagct caagagcgtt gtaggagaaa agaaagtggt gagcgaatca     1020
gaaatggcga ggctgccata cttgcaagca gtgatcaaga agtgctccg acttcaccct      1080 cccggccctc ttctgcttcc tcgcaaggca gggagtgatc aagttgtgaa tggatacctg     1140
atcccaaagg gaactcaatt actcttcaat gtatgggcaa tggcagaga ccccagtatc      1200 tggaagaatc ctgaatctt cgagcccgag cgcttcctca atcaaaacat agactacaaa      1260
ggccaagatt tcgagctcat tccattcggg tccgggagaa gaatttgccc cggtatgccg     1320
ctggcggatc ggattatgca catgacgacg gccactctgg ttcacaactt cgattggaaa     1380
ctggaagacg gagcaggtga tgcggatcac aaggagacg accccttcgg cttggccatc     1440
cgccgtgcaa ctcctctcag gatcattcca cttaagccat ga                        1482
```

<210> SEQ ID NO 13
<211> LENGTH: 1482
<212> TYPE: DNA
<213> ORGANISM: Coleus forskohlii

<400> SEQUENCE: 13

```
atggaaagca tgaatgctct tgtcgtcggt ctcttgttga tcgctttgac aattttgttt       60
tcgttgaggc ggcggagaaa ccttgctccg gggccttatc cttttccgat catcggaaac      120
atgcttcaac tgggcacgaa accacaccaa tcattcgccc agctgtcgaa gaaatatggg      180
ccgctcatgt ccatccacct gggaagttta tacacagtga tcgtttcgtc gccggaaatg      240
gcgaaagaga tcctgcaaaa gcacggccaa gtgttttcag ggagaaccat cgctcaggcg      300
gtgcatgcat gcgaccacga caagatctcc atgggggttc tgccggtgtc gaacacgtgg      360
cgcgatatgc gtaaaatatg caaagagcag atgttctcgc atcacagctt ggaaggcagc      420
cagggtctcc gccagcagaa gctgctgcag ctgctcgact acgcccagaa gtgctgcgaa      480
accggccgcg ccgttgacat tcgtgaggct tccttcatca caactctcaa cctcatgtcg      540
gccaccatgt tttcgactca agctaccgag tttgaatcga aatctactca ggagttcaag      600
gagatcattg aaggcgtggc cacgattgtg ggcgtggcta atttcggaga ctacttccca      660
atcttgaagc ctttcgatct gcaggggatc aagagaaaag ctgatggcta cttcggcaga      720
```

```
ttgctgaaat taatcgaggg ctatctcaat gaaagattgg aatccagaaa atcgaaccca    780
aatgccccca gaaagaatga cttttggaa  acagtggtcg atatcctcga ggcaaatgag    840
tacaagttgt cagtcgacca cctcacgcat ctcatgctgg atttgtttgt tggaggatcg    900
gaaacaaaca cgacctcact ggagtggaca atgtcggagt tagtgaacaa ccccgacaaa    960
atggccaagc tgaaacagga gctgaagagc gttgtaggag agaggaaact ggtggatgag   1020
tcggagatgc cgaggctgcc atatctgcaa gctgtcatca aagaatcgct ccgaattcac   1080
ccaccgggcc ctcttcttct ccctcgcaaa gcagagaccg atcaagaggt gaatggatat   1140
ctcatcccaa aagggactca gattctcttc aatgtgtggg caatgggcag ggatcctagc   1200
atctggaagg atcctgaatc tttgagccc  gagcgcttcc tcaatcaaaa catagacttc   1260
aaaggccaag atttcgagct cattccattc gggtcgggcc gaagaatctg ccccggcatg   1320
ccgctggcca atcggattct ccacatggcc accgcgacta tggttcataa cttcgattgg   1380
aaactggaac aaggaacaga tgaagctgat gccaaaggag agttgtttgg attggccgtg   1440
cgcagggcag ttcccctcag gatcattcca cttcagcctt aa                      1482
```